US012345701B2

(12) United States Patent
Bronevetsky et al.

(10) Patent No.: US 12,345,701 B2
(45) Date of Patent: Jul. 1, 2025

(54) METHODS FOR ASSAYING BIOLOGICAL CELLS IN A MICROFLUIDIC DEVICE

(71) Applicant: BRUKER CELLULAR ANALYSIS, INC., Emeryville, CA (US)

(72) Inventors: Yelena Bronevetsky, Emeryville, CA (US); Annamaria Mocciaro, Emeryville, CA (US); Guido K. Stadler, Emeryville, CA (US); Peter J. Beemiller, Emeryville, CA (US); Natalie C. Marks, Emeryville, CA (US); Duane Smith, Emeryville, CA (US); Vincent Haw Tien Pai, Emeryville, CA (US); Jason M. McEwen, Emeryville, CA (US); Amanda L. Goodsell, Emeryville, CA (US); John A. Tenney, Emeryville, CA (US); Thomas M. Vetterli, Emeryville, CA (US); Hansohl E. Kim, Emeryville, CA (US)

(73) Assignee: BRUKER CELLULAR ANALYSIC, INC., Emeryville, CA (US)

( * ) Notice: Subject to any disclaimer, the term of this patent is extended or adjusted under 35 U.S.C. 154(b) by 1024 days.

(21) Appl. No.: 17/241,865

(22) Filed: Apr. 27, 2021

(65) Prior Publication Data
US 2021/0349075 A1 Nov. 11, 2021

Related U.S. Application Data

(63) Continuation of application No. PCT/US2019/059495, filed on Nov. 2, 2019.

(60) Provisional application No. 62/754,107, filed on Nov. 1, 2018, provisional application No. 62/754,147, filed on Nov. 1, 2018, provisional application No. 62/881,129, filed on Jul. 31, 2019.

(51) Int. Cl.
G01N 33/50 (2006.01)
B01L 3/00 (2006.01)

(52) U.S. Cl.
CPC ...... *G01N 33/505* (2013.01); *B01L 3/502761* (2013.01); *G01N 33/5014* (2013.01); *B01L 2200/0647* (2013.01)

(58) Field of Classification Search
CPC .............. G01N 33/505; G01N 33/5014; B01L 3/502761; B01L 2200/0647
See application file for complete search history.

(56) References Cited

U.S. PATENT DOCUMENTS

| 6,294,063 | B1 | 9/2001 | Becker et al. |
|---|---|---|---|
| 6,942,776 | B2 | 9/2005 | Medoro |
| 7,090,759 | B1 | 8/2006 | Seul |
| 8,581,167 | B2 | 11/2013 | Lean et al. |
| 9,144,806 | B2 | 9/2015 | Chen et al. |
| 2003/0008364 | A1 | 1/2003 | Wang et al. |
| 2004/0072278 | A1 | 4/2004 | Chou et al. |
| 2004/0191789 | A1 | 9/2004 | Manaresi et al. |
| 2004/0197905 | A1 | 10/2004 | Hafeman |
| 2005/0112548 | A1 | 5/2005 | Segawa et al. |
| 2005/0129581 | A1 | 6/2005 | McBride et al. |
| 2005/0175981 | A1 | 8/2005 | Voldman et al. |
| 2006/0091015 | A1 | 5/2006 | Lau |
| 2006/0154361 | A1 | 7/2006 | Wikswo et al. |
| 2007/0095669 | A1 | 5/2007 | Lau et al. |
| 2007/0183934 | A1 | 8/2007 | Diercks et al. |
| 2008/0223721 | A1 | 9/2008 | Cohen et al. |
| 2008/0302732 | A1 | 12/2008 | Soh et al. |
| 2009/0023608 | A1 | 1/2009 | Hung et al. |
| 2009/0170186 | A1 | 7/2009 | Wu et al. |
| 2010/0003666 | A1 | 1/2010 | Lee et al. |
| 2010/0101960 | A1 | 4/2010 | Ohta et al. |
| 2010/0109687 | A1 | 5/2010 | Drimusz et al. |
| 2010/0240542 | A1 | 9/2010 | Soper et al. |
| 2010/0273681 | A1 | 10/2010 | Cerrina et al. |
| 2011/0053151 | A1 | 3/2011 | Hansen et al. |
| 2011/0117634 | A1 | 5/2011 | Halamish et al. |
| 2011/0143964 | A1 | 6/2011 | Zhou et al. |
| 2011/0262906 | A1 | 10/2011 | Dimov et al. |

(Continued)

FOREIGN PATENT DOCUMENTS

| CN | 101275114 A | 10/2008 |
|---|---|---|
| CN | 105492621 A | 4/2016 |

(Continued)

OTHER PUBLICATIONS

Pietilä (Stem Cell Research & Therapy 2012 vol. 3:53). (Year: 2012).*
CN108603878A, Beaumont et al.—Machine Translation, Sep. 28, 2018, 71 pages.
Chiou et al., "Massively parallel manipulation of single cells and microparticles using optical images," Nature, vol. 436 (Jul. 21, 2005), pp. 370-372.
Chiou, Pei-Yu, Massively Parallel Optical Manipulation of Cells, Micro- and Nano-Particles on Optoelectronic devices, Dissertation, University of California at Berkeley, 2005 (147 pages).

(Continued)

*Primary Examiner* — Changhwa J Cheu
(74) *Attorney, Agent, or Firm* — Kenneth E. Horton; Barnes & Thornburg LLP

(57) ABSTRACT

Methods are provided for the assay of secreted biomolecules using automated detection and characterization of micro-objects in a microfluidic device. The biomolecules can be secreted by cells, particularly immunological cells, such as T cells. The biomolecules being assayed can include cytokines, growth factors, and the like. Methods are also provided for assaying the cytotoxicity of a cell with respect to another, target cell. Also provided are kits and non-transitory computer-readable media in which programs are stored for causing a system comprising a computer to perform automated methods for detecting secreted biomolecules and/or cytotoxicity in a microfluidic device.

23 Claims, 46 Drawing Sheets

Specification includes a Sequence Listing.

(56) References Cited

U.S. PATENT DOCUMENTS

| | | |
|---|---|---|
| 2012/0009671 A1 | 1/2012 | Hansen et al. |
| 2012/0015347 A1 | 1/2012 | Singhal et al. |
| 2012/0118740 A1 | 5/2012 | Garcia et al. |
| 2012/0156675 A1 | 6/2012 | Lueerssen et al. |
| 2012/0325665 A1 | 12/2012 | Chiou et al. |
| 2013/0115606 A1 | 5/2013 | Hansen et al. |
| 2013/0118905 A1 | 5/2013 | Morimoto et al. |
| 2013/0121983 A1* | 5/2013 | Jones ............ C12Y 204/02036 435/15 |
| 2013/0130232 A1 | 5/2013 | Weibel et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0252258 A1 | 9/2013 | Bocchi et al. |
| 2013/0261021 A1 | 10/2013 | Bocchi et al. |
| 2014/0116881 A1 | 5/2014 | Chapman et al. |
| 2014/0124370 A1 | 5/2014 | Short et al. |
| 2015/0018226 A1 | 1/2015 | Hansen et al. |
| 2015/0119288 A1 | 4/2015 | Soper et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2016/0171686 A1 | 6/2016 | Du et al. |
| 2016/0184821 A1 | 6/2016 | Hobbs et al. |
| 2016/0193604 A1 | 7/2016 | McFarland et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe, Jr. et al. |
| 2017/0224734 A1 | 8/2017 | Chapman et al. |
| 2018/0298318 A1 | 10/2018 | Kurz et al. |
| 2019/0008924 A1* | 1/2019 | Cohen .................... A61P 37/06 |
| 2019/0071502 A1* | 3/2019 | Weidanz ................ C07K 16/30 |
| 2019/0240665 A1 | 8/2019 | Lionberger et al. |
| 2019/0275516 A1 | 9/2019 | Lowe, Jr. et al. |
| 2019/0374944 A1 | 12/2019 | Lundquist et al. |
| 2019/0384963 A1 | 12/2019 | Kim et al. |
| 2020/0371126 A1 | 11/2020 | Thaker et al. |
| 2021/0272654 A1 | 9/2021 | Thaker et al. |

FOREIGN PATENT DOCUMENTS

| | | |
|---|---|---|
| CN | 108603878 A | 9/2018 |
| JP | 2007537729 A | 12/2007 |
| KR | 20100008222 A | 1/2010 |
| KR | 10-2018-0091062 A | 8/2018 |
| WO | 2002088702 A2 | 11/2002 |
| WO | 2004089810 A2 | 10/2004 |
| WO | 2005100541 A2 | 10/2005 |
| WO | 2007008609 A2 | 1/2007 |
| WO | 2007024701 A2 | 3/2007 |
| WO | 2008119066 A1 | 10/2008 |
| WO | 2009130694 A2 | 10/2009 |
| WO | 2010040851 A2 | 4/2010 |
| WO | 2010115167 A2 | 10/2010 |
| WO | 2010147078 A1 | 12/2010 |
| WO | 2011149032 A1 | 12/2011 |
| WO | 2011160430 A1 | 12/2011 |
| WO | 2012037030 A2 | 3/2012 |
| WO | 2012072823 A1 | 6/2012 |
| WO | 2013019491 A1 | 2/2013 |
| WO | WO-2014153651 A1 * | 10/2014 ........ B01L 3/502715 |
| WO | 2017100347 A1 | 6/2017 |
| WO | 2018102748 A1 | 6/2018 |
| WO | 2019018801 A1 | 1/2019 |
| WO | 2019232473 A2 | 12/2019 |
| WO | 2020092975 A2 | 5/2020 |

OTHER PUBLICATIONS

Chung et al., Imaging Single-Cell Signaling Dynamics with a Deterministic High-Density Single-Cell Trap Array, Anal. Chem. 83(18):7044-7052 (2011).

CN101275114A, Luo—Machine Translation, Oct. 1, 2008, 8 pages.

Hsu, HY et al., "Sorting of Differentiated Neurons Using Phototransistor-Based Optoelectronic Tweezers for Cell Replacement Therapy of Neurodegenerative Diseases", Transducers 2009, Denver, CO USA Jun. 2009, download dated Nov. 23, 2009 from IEEE Xplore, 4 pages.

Hung et al., Continuous Perfusion Microfluidic Cell Culture Array for High-Throughput Cell-Based Assays, Biotech and Bioengineering 89(1): 1-8 (2004). Dec. 3, 2004.

Iliescu et al., Continuous Field-Flow Separation of Particle Populations in a Dielectrophoretic Chip with Three Dimensional Electrodes, Applied Physics Letters 90:234104 (2007).

KIPO computer-generated English language translation of KR 20100008222A_Kyun, 2010.

Nevill et al., Integrated microfluidic cell culture and lysis on a chip, Lab on a Chip 7:1689-95 (2007).

Pavesi, A. et al. "A 3D microfluidic model for preclinical evaluation of TCR-engineered T cells against solid tumors." JCI Insight. 2017, vol. 2, No. 12, pp. 1-18.

Somaweera H. et al., Generation of a Chemical Gradient Across an Array of 256 Cell Cultures in a Single Chip. Analyst, Oct. 7, 2013, vol. 138, No. 19, pp. 5566-5571.

Valley et al., Optoelectronic Tweezers as a Tool for Parallel Single-Cell Manipulation and Simulation, IEEE Transactions on Biomedical Circuits and Systems, vol. 3, No. 6 (Dec. 2009), pp. 424-431.

WO2010147078, University of Tokyo, Machine Translation, Dec. 23, 2010, 12 pages.

Xu, Guoling et al,. Recent Trends in Dielectrophoresis, Informacije MIDEM, 2010, vol. 40, Issue No. 4, pp. 253-262.

Yi et al., "Microfluidics technology for manipulation and analysis of biological cells," Analytica Chimica Acta 560 (2006), pp. 1-23.

* cited by examiner

Enlarged area from FIG. 15A

T cells and TCL 1 Tumor cells

T cells and Beads

T cells plus SLC45 Tumor cells

Assay Results TxRed

Assay result brightfield assay Result TxRed assay results brightfield

Quantification of assay results

METHODS FOR ASSAYING BIOLOGICAL CELLS IN A MICROFLUIDIC DEVICE

CROSS REFERENCE TO RELATED APPLICATIONS

This application claims the benefit of U.S. Provisional Application No. 62/754,107, filed on Nov. 1, 2018, entitled "METHODS FOR DETECTION OF SECRETED BIOMOLECULE OF INTEREST IN A MICROFLUIDIC ENVIRONMENT USING AUTOMATED DETECTION AND CHARACTERIZATION OF MICRO-OBJECTS"; U.S. Provisional Application No. 62/754,147, filed on Nov. 1, 2018, entitled "METHODS OF CO-ASSAY OF ANTIGEN-SPECIFIC T LYMPHOCYTE CYTOTOXICITY AND SECRETED BIOMOLECULE THEREFROM IN A MICROFLUIDIC ENVIRONMENT, AND KITS THEREFOR"; and U.S. Provisional Application No. 62/881,129, filed on Jul. 31, 2019, entitled "METHODS FOR DETECTION OF SECRETED BIOMOLECULES OF INTEREST IN A MICROFLUIDIC ENVIRONMENT USING AUTOMATED DETECTION AND CHARACTERIZATION OF MICRO-OBJECTS", each of which disclosures is herein incorporated by reference in its entirety for all purposes.

REFERENCE TO SEQUENCE LISTING

A sequence listing entitled "88596-344665 Apr. 30, 2025 ST25" is an ASCII text file and is incorporated herein by reference in its entirety. The text file was created on Apr. 30, 2025, and is 4,096 bytes in size.

FIELD

The present disclosure generally relates to methods for assaying biological cells, particularly in a microfluidic environment. The methods can include detection of secreted biomolecules of interest and may include steps for automatically detecting and characterizing micro-objects in an image. For example, the methods can include steps for automatically detecting in a first image (e.g., a bright field image) micro-objects, such as cells or beads, that are located within a microfluidic device, and using the detected positions of the micro-objects to measure characteristics of the micro-objects in corresponding images (e.g., fluorescent images, infrared, ultraviolet). Alternatively, or in addition, the methods can include a determination of whether a first biological cell, such as a T lymphocyte, has a cytotoxic activity with respect to another biological cell (e.g., a target cell).

INTRODUCTION AND SUMMARY

In the biological and pharmaceutical sciences, assays on groups of one or more biological cells are performed to study the properties of the cell(s) and identify cells for further study and/or therapeutic use. The amount of data that can be generated from a single assay, as well as the resolution of the assay (e.g., detecting the properties of one cell, a small group of cells, or a large population of cells) determines the utility of the assay. Until recently, assays of single cells, or even small groups of cells, were difficult to perform successfully due to the small amount of signal generated. Moreover, even when an instrument is capable of single cell analysis, such as a fluorescence activated cell sorter (FACS) instrument or a droplet-based microfluidic platform, the analysis can require large size starting samples (e.g., many millions of cells) and options for multiplexing assays and/or recovery of cells post-assay can be limited or non-existent. Accordingly, there remains a need for robust assays that enable analysis of cellular samples of small size and allow for single cell analysis, flexibility, and/or multiplexing.

The presently disclosed assays provide for the detection of one or more molecules of interest secreted (or otherwise presented) by a biological cell. Alternatively, or in addition, the disclosed assays provide for a measure of the cytotoxic activity of a test biological cell against a target biological cell. The assays can be performed in a chamber of a microfluidic device and, optionally, can incorporate automated image processing and manipulation and/or selection of cells. The biological cells being assayed can be, for example, immunological cells (e.g., T lymphocytes, including CD8+ or CD4+ T cells, B lymphocytes, including memory B cells or plasma cells, natural killer (NK) cells, macrophages, or the like), cancer cells, stem or progenitor cells, gametes (e.g., sperm or oocytes), embryos (e.g., zygotes), or the like. The molecule of interest secreted by the biological cell can be, for example, a cytokine (e.g., TNF alpha, TGF beta, INF gamma, IL1 beta, IL2, IL4, IL6, IL10, IL12, IL13, IL17A, IL22, GM-CSF, or any combination thereof. The target biological cell can be, for example, an antigen presenting cell. Further embodiments of the assays are disclosed below.

Embodiment 300. A method for detecting a first biological molecule of interest secreted by a biological cell in a chamber of a microfluidic device, the method comprising: disposing the biological cell within the chamber of the microfluidic device; disposing a first micro-object in or proximal to the chamber of the microfluidic device, wherein the first micro-object comprises a first binding agent that binds to the first molecule of interest; incubating the biological cell together with the first micro-object under conditions sufficient to allow the biological cell to secrete the first molecule of interest into the chamber and for the secreted first molecule of interest to diffuse over and bind to the first micro-object; and detecting binding of the first molecule of interest to the first micro-object, wherein detecting binding is performed according to the method of any one of Embodiments 200 to 262.

Embodiment 301. The method of embodiment 300, wherein the biological cell is an immunological cell.

Embodiment 302. The method of embodiment 301, wherein the immunological cell is a T cell (e.g., naïve T cell, memory T cell, central memory T cell, effector T cell, or the like).

Embodiment 303. The method of embodiment 301, wherein the immunological cell is a B cell (e.g., a memory B cell), a plasmablast, or a plasma cell.

Embodiment 304. The method of embodiment 301, wherein the immunological cell is a NK cell or a macrophage.

Embodiment 305. The method of embodiment 300, wherein the biological cell is a liver cell or a neuron.

Embodiment 306. The method of embodiment 300, wherein the biological cell is a stem cell, a progenitor cell, or a cell derived from a stem or progenitor cell.

Embodiment 307. The method of embodiment 300, wherein the biological cell a zygote or is comprised by or isolated from an embryo (e.g., a mammalian embryo).

Embodiment 308. The method of any one of embodiments 300 to 307, wherein the chamber of the microfluidic device is a sequestration pen that comprises an isolation region and a connection region, wherein the connection region fluidically connects the isolation region to a flow region (e.g., a microfluidic channel) of the microfluidic device, and wherein the isolation region is an unswept region of the microfluidic device.

Embodiment 309. The method of embodiment 308, wherein the isolation region of the sequestration pen has a single opening to the connection region.

Embodiment 310. The method of embodiment 308 or 309, wherein the connection region of the sequestration pen has a proximal opening to a flow region of the microfluidic device and a distal opening to the isolation region, wherein the proximal opening of the connection region has a width $W_{con}$ from about 20 microns to about 100 microns, and wherein a length $L_{con}$ of the connection region from the proximal opening to the distal opening is at least 1.0 times the width $W_{con}$ of the proximal opening.

Embodiment 311. The method of embodiment 310, wherein the length $L_{con}$ of the connection region from the proximal opening to the distal opening is at least 1.5 times or at least 2.0 times the width $W_{con}$ of the connection region.

Embodiment 312. The method of embodiment 310 or 311, wherein the length $L_{con}$ of the connection region from the proximal opening to the distal opening is in in the range of about 20 microns to about 500 microns; wherein the height $H_{ch}$ of the flow region (or microfluidic channel) at the proximal opening of the connection region is in the range of about 20 microns and about 100 microns; and/or wherein the width $W_{ch}$ of the flow region (or microfluidic channel) at the proximal opening of the connection region is in the range of about 50 microns to about 500 microns.

Embodiment 313. The method of any one of embodiments 300 to 312, wherein disposing the biological cell within the chamber of the microfluidic device comprises selecting the biological cell from a population of biological cells and moving the selected biological cell into the chamber (e.g., into the isolation region of a sequestration pen). Note: the selection can comprise performing the method of any one of embodiments 200 to 262; prior to selection, the population of biological cells can be flowing into a flow region (e.g., a channel proximal to the chamber) of the microfluidic device; optionally, the population of cells can be stained, prior to introduction into the microfluidic device, to highlight one or more cellular characteristics.

Embodiment 314. The method of embodiment 313, wherein the biological cell is selected, at least in part, based on one or more physical characteristics (e.g., size, as measured by diameter, area in a 2D image, or the like; ratio of nuclear size to cell size; etc.).

Embodiment 315. The method of embodiment 313 or 314, wherein the biological cell is selected, at least in part, based on expression of one or more surface markers (e.g., each of which can be a protein, proteoglycan, lipid, or other cell surface molecule).

Embodiment 316. The method of embodiment 315, wherein the one or more surface markers is/are indicative of an immunological cell type (e.g., an activated T cell).

Embodiment 317. The method of embodiment 315, wherein the one or more surface markers are CD3, CD4, CD8, CD137, or any combination thereof (e.g., CD8 and CD137).

Embodiment 318. The method of any one of embodiments 300 to 317, wherein disposing the first micro-object comprises disposing the first micro-object in the chamber of the microfluidic device (e.g., into the isolation region of a sequestration pen).

Embodiment 319. The method of any one of embodiments 300 to 318, wherein the first binding agent of the first micro-object comprises a protein.

Embodiment 320. The method of embodiment 319, wherein the protein of the first binding agent is an antibody or a receptor for the molecule of interest.

Embodiment 321. The method of any one of embodiments 300 to 320, wherein the first molecule of interest is a protein.

Embodiment 322. The method of any one of embodiments 300 to 320, wherein the first molecule of interest is a cytokine or a growth factor.

Embodiment 323. The method of any one of embodiments 300 to 320, wherein the first molecule of interest is a hormone.

Embodiment 324. The method of any one of embodiments 300 to 320, wherein the first molecule of interest is an antibody.

Embodiment 325. The method of any one of embodiments 300 to 320, wherein the first molecule of interest is a neurotransmitter.

Embodiment 326. The method of any one of embodiments 300 to 320, wherein the first molecule of interest is a small molecule (e.g., metabolite, secondary messenger, hormone), lipid, fatty acid, carbohydrate, or the like.

Embodiment 327. The method of any one of embodiments 300 to 326, wherein incubating the biological cell comprises incubating the biological cell together with the first micro-object for a period of time of at least 10 minutes (e.g., 15, 20, 25, 30, 35, 40, 45, 50, 55, 60 minutes, or longer).

Embodiment 328. The method of any one of embodiments 300 to 327, wherein detecting binding of the first molecule of interest to the first micro-object comprises introducing a first reagent into the microfluidic device, wherein the first reagent binds to the first molecule of interest at a site (e.g., epitope) such that binding of the first reagent to the first molecule of interest does not interfere with binding of the first molecule of interest to the first micro-object.

Embodiment 329. The method of any one of embodiments 300 to 327, wherein detecting binding of the first molecule of interest to the first micro-object comprises introducing a first reagent into the microfluidic device, wherein the first reagent binds to the first binding agent of the first micro-object when the first molecule of interest is also bound to the first binding agent, but not when the first binding agent is not bound to the first molecule of interest.

Embodiment 330. The method of embodiment 328 or 329, wherein the first reagent comprises a label (e.g., a fluorescent label).

Embodiment 331. The method of any one of embodiments 328 to 330, wherein introducing a first reagent into the microfluidic device comprises flowing (or perfusing) the reagent through the microfluidic device.

Embodiment 332. The method of embodiment 331, wherein the microfluidic device further comprises a microfluidic channel, wherein the chamber or sequestration pen comprises an opening to the microfluidic channel, and wherein flowing the first reagent through the microfluidic device comprises flowing the first reagent through the microfluidic channel.

Embodiment 333. The method of any one of embodiments 300 to 332, wherein the method further comprises: disposing a second micro-object in or proximal to the chamber of the microfluidic device, wherein the second micro-object comprises a second binding agent that binds to a second molecule of interest produced by the biological cell; incubating the biological cell together with the second micro-object under conditions sufficient to allow the biological cell to secrete the second molecule of interest into the chamber and for the secreted second molecule of interest to diffuse over and bind to the second micro-object; and detecting binding of the second molecule of interest to the second micro-object, wherein detecting binding is performed according to the method of any one of embodiments 200 to 262.

Embodiment 334. The method of embodiment 333, wherein: the second micro-object is detectably distinguishable from the first micro-object; the second molecule of interest is different from the first molecule of interest; the second binding agent binds to the second molecule of interest and substantially not to the first molecule of interest and the first binding agent does not substantially bind to the second molecule of interest; and detection of binding of the second molecule of interest is distinguishable from detection of binding of the first molecule of interest Embodiment 335. The method of embodiment 333 or 334, wherein detecting binding of the second molecule of interest to the second micro-object comprises introducing a second reagent into the microfluidic device, wherein the second reagent binds to the second molecule of interest at a site (e.g., epitope) such that binding of the second reagent to the second molecule of interest does not interfere with binding of the second molecule of interest to the second micro-object.

Embodiment 336. The method of embodiments 333 or 334, wherein detecting binding of the second molecule of interest to the second micro-object comprises introducing a second reagent into the microfluidic device, wherein the second reagent labels the second molecule bound to the second micro-object.

Embodiment 337. The method of any one of embodiments 333 to 336, wherein the second reagent binds to the second binding agent of the second micro-object when the second molecule of interest is also bound to the second binding agent, but not when the second binding agent is not bound to the second molecule of interest.

Embodiment 338. The method of any one of embodiments 333 to 337, wherein the second reagent comprises a label (e.g., a fluorescent label).

Embodiment 339. The method of embodiment 338, wherein the label of the second reagent is spectrally distinct from a label of the first reagent.

Embodiment 340. The method of any one of embodiments 333 to 339, wherein the second molecule of interest is a protein.

Embodiment 341. The method of embodiment 340, wherein the second molecule of interest is an antibody, cytokine, proteolytic enzyme, or hormone.

Embodiment 342. The method of any one of embodiments 333 to 339, wherein the second molecule of interest is a small molecule.

Embodiment 343. The method of embodiment 342, wherein the second molecule of interest is a neurotransmitter, hormone, metabolite, secondary messenger, hormone, lipid, fatty acid, carbohydrate, or the like.

Embodiment 344. The method of any one of embodiments 333 to 343, wherein the second binding agent of the second micro-object comprises a protein.

Embodiment 345. The method of embodiment 344, wherein the protein of the second binding agent is an antibody or a receptor for the second molecule of interest.

Embodiment 346. The method of any one of embodiments 300 to 345, wherein the microfluidic device comprises a plurality of chambers.

Embodiment 347. The method of embodiment 346, wherein each of at least a subset of the plurality of chambers of the microfluidic device is a sequestration pen that comprises an isolation region and a connection region, wherein the connection region fluidically connects the isolation region to a flow region (e.g., a microfluidic channel) of the microfluidic device, and wherein the isolation region is an unswept region of the microfluidic device.

Embodiment 348. The method of embodiment 347, wherein the sequestration pen is the sequestration pen of any one of embodiments 308 to 312.

Embodiment 349. A non-transitory computer-readable medium in which a program is stored for causing a system comprising a computer to perform a method for detecting a first biological molecule of interest secreted by a biological cell in a chamber of a microfluidic device, the method comprising: disposing the biological cell within the chamber of the microfluidic device; disposing a first micro-object in or proximal to the chamber of the microfluidic device, wherein the first micro-object comprises a first binding agent that binds to the first molecule of interest; incubating the biological cell together with the first micro-object under conditions sufficient to allow the biological cell to secrete the first molecule of interest into the chamber and for the secreted first molecule of interest to diffuse over and bind to the first micro-object; and detecting binding of the first molecule of interest to the first micro-object.

Embodiment 350. The non-transitory computer-readable medium of embodiment 349, wherein the method is the method of any one of embodiments 300 to 348.

Embodiment 400. A method of assaying for antigen-specific cytotoxicity of a T lymphocyte (T cell) in a microfluidic device, the method comprising: disposing the T cell within the microfluidic device; disposing a target cell in proximity to the T cell; and determining a viability of the target cell after a period of exposure in proximity to the T cell.

Embodiment 401. The method of embodiment 400, wherein the target cell expresses an antigen for which the T cell is specific.

Embodiment 402. The method of embodiment 400 or 401, wherein the assay is a co-assay and further comprises: disposing a first capture object in proximity to the T lymphocyte, wherein the capture micro-object is configured to capture a first secreted biomolecule released from the T cell; and detecting the first secreted biomolecule captured to the first capture object.

Embodiment 403. The method of embodiment 402, wherein the first secreted biomolecule is a protein.

Embodiment 404. The method of embodiment 402 or 403, wherein the first secreted protein released from the antigen-specific T cell is a cytokine.

Embodiment 404. The method of embodiment 404, wherein the cytokine is Tumor Necrosis Factor alpha (TNF alpha), Transforming Growth Factor beta (TGF beta), Interferon gamma (IFN gamma), Interleukin-1 beta (IL1 beta), Interleukin-2 (IL2), Interleukin-4 (IL4), Interleukin-5 (IL5), Interleukin-6 (IL6), Interleukin-10 (IL10), Interleukin-12 (IL12), Interleukin-13 (IL13), Interleukin-17A (IL17A), or Interleukin-22 (IL22).

Embodiment 405. The method of embodiment 402 or 403, wherein the first secreted protein released from the antigen-specific T cell is a granzyme or a perforin protein.

Embodiment 406. The method of any one of embodiments 400 to 404, wherein the target cell is a cancer cell.

Embodiment 407. The method of embodiment 406, wherein the target cancer cell is a cell from a cell line that expresses a cancer-associated or cancer-specific antigen.

Embodiment 408. The method of embodiment 406 or 407, wherein the target cell expresses an antigen associated with melanoma, breast cancer, or lung cancer.

Embodiment 409. The method of any one of embodiments 400 to 408, wherein the T cell is a mammalian T cell.

Embodiment 410. The method of any one of embodiments 400 to 409, wherein the T cell is antigen-specific for a tumor associated antigen.

Embodiment 411. The method of embodiment 410, wherein the tumor associated antigen is SLC45A2, TCL1, VCX3A, MART1, or NYESO1.

Embodiment 412. The method of any one of embodiments 400 to 411, wherein the T cell expresses a chimeric antigen receptor.

Embodiment 413. The method of any one of embodiments 400 to 411, wherein the T cell does not express a chimeric antigen receptor.

Embodiment 414. The method of any one of embodiments 400 to 413, wherein the microfluidic device comprises a flow region for containing a flow of a first fluidic medium and a chamber opening to the flow region.

Embodiment 415. The method of embodiment 414, wherein the microfluidic device further comprises a microfluidic channel.

Embodiment 416. The method of embodiment 414 or 415, wherein the flow region is a microfluidic channel.

Embodiment 417. The method of any one of embodiments 414 to 416, wherein the chamber comprises a sequestration pen.

Embodiment 418. The method of embodiment 417, wherein the sequestration pen comprises an isolation region for containing a second fluidic medium, the isolation region having a single opening, wherein the isolation region of the sequestration pen is an unswept region of the microfluidic device; and a connection region fluidically connecting the isolation region to the flow region.

Embodiment 419. The method of any one of embodiments 414 to 418, wherein the T cell, the target cell, and, optionally, the first capture object are each disposed in the chamber.

Embodiment 420. The method of embodiment 418 or 419, wherein the T cell, the first capture object and the target cell are each disposed in the isolation region of the sequestration pen.

Embodiment 421. The method of any one of embodiments 414 to 418, wherein disposing the T cell in the chamber comprises disposing a single T cell into the chamber.

Embodiment 422. The method of any one of embodiments 414 to 421, wherein disposing the target cell in the chamber comprises disposing a single target cell into the chamber.

Embodiment 423. The method of any one of embodiments 414 to 422, wherein disposing the T cell within the microfluidic device is performed using dielectrophoretic (DEP) forces.

Embodiment 424. The method of any one of embodiments 414 to 423, wherein disposing the first capture object in proximity to the T cell is performed using dielectrophoretic (DEP) forces.

Embodiment 425. The method of any one of embodiments 414 to 424, wherein disposing the target cell in proximity to the T cell is performed using dielectrophoretic (DEP) forces.

Embodiment 426. The method of any one of embodiments 423 to 425, wherein the DEP forces are optically actuated.

Embodiment 427. The method of any one of embodiments 400 to 426, wherein detecting the first secreted biomolecule captured to the first capture object further comprises incubating the T cell for a period of time sufficient to permit the T cell to secrete the first secreted biomolecule and for the first capture object to capture the first secreted biomolecule.

Embodiment 428. The method of any one of embodiments 400 to 427, further comprising introducing a first secreted biomolecule detection reagent into the microfluidic device.

Embodiment 429. The method of embodiment 428, wherein the first secreted biomolecule detection reagent binds to the first secreted biomolecule when it is captured by the first capture object, but does not bind to the first secreted biomolecule when it is not captured by the first capture object.

Embodiment 430. The method of any one of embodiments 400 to 429, wherein detecting the first secreted biomolecule comprises detecting a colorimetric, luminescent or fluorescent signal.

Embodiment 431. The method of any one of embodiments 400 to 430, wherein determining the viability of the target cell comprises contacting the target cell with a detectable marker configured to label a non-viable cell.

Embodiment 432. The method of embodiment 431, wherein the detectable marker configured to label a non-viable cell is configured to label apoptotic cells.

Embodiment 433. The method of embodiment 431, wherein the detectable marker configured to label a non-viable cell is configured to label calcium flux or mitochondrial membrane potential.

Embodiment 434. The method of any one of embodiments 400 to 433, wherein the determining the viability of the target cell after the period of exposure to the T cell is repeated over a plurality of periods of exposure to the T cell.

Embodiment 435. The method of any one of embodiments 400 to 434, further comprising labelling the T cell for the presence of one or more cell surface markers associated with proliferation, activation, metabolic activity, memory, exhaustion, and/or lineage.

Embodiment 436. The method of embodiment 435, wherein the label for the one or more cell surface markers is colorimetric, luminescent or fluorescent.

Embodiment 437. The method of any one of embodiments 400 to 436, further comprising a second capture object, configured to capture a second secreted biomolecule, wherein the second secreted protein is not the same as the first secreted protein.

Embodiment 438. The method of any one of embodiments 414 to 437, wherein the microfluidic device further comprises a plurality of chambers.

Embodiment 439. The method of any one of embodiments 400 to 438, further comprising: after determining the viability of the target cell, capturing nucleic acid from the T cell.

Embodiment 440. The method of embodiment 439, further comprising sequencing the nucleic acid captured from the T cell.

Embodiment 441. The method of any one of embodiments 400 to 438, further comprising: after determining the viability of the target cell, exporting the T cell from the microfluidic device.

Embodiment 442. The method of any one of embodiments 400 to 441, wherein determining the viability of the target cell comprises detecting the target cell according to any one of embodiments 1 to 51 or 93 to 128.

Embodiment 443. The method of any one of embodiments 402 to 442, wherein detecting the first secreted biomolecule captured to the first capture object comprises detecting the first capture object according to any one of embodiments 1 to 51 or 93 to 128.

Embodiment 450. A non-transitory computer-readable medium in which a program is stored for causing a system comprising a computer to perform a method of assaying for antigen-specific cytotoxicity of a T lymphocyte (T cell) in a microfluidic device, the method comprising: disposing the T cell within the microfluidic device; disposing a target cell in proximity to the T cell; and determining a viability of the target cell after a period of exposure in proximity to the T cell.

Embodiment 451. The method of the non-transitory computer-readable medium of embodiment 500, wherein the target cell expresses an antigen for which the T cell is specific.

Embodiment 452. The method of the non-transitory computer-readable medium of embodiment 450 or 451, wherein the assay is a co-assay and further comprises: disposing a first capture object in proximity to the T lymphocyte, wherein the capture micro-object is configured to capture a first secreted biomolecule released from the T cell; and detecting the first secreted biomolecule captured to the first capture object.

Embodiment 453. The method of the non-transitory computer-readable medium of embodiment 452, wherein the first secreted biomolecule is a protein.

Embodiment 454. The method of the non-transitory computer-readable medium of embodiment 452 or 453, wherein the first secreted protein released from the antigen-specific T cell is a cytokine.

Embodiment 455. The method of the non-transitory computer-readable medium of any one of embodiments 451 to 454, wherein the method is the method of any one of embodiments 405 to 443.

Embodiment 500. A kit for assaying antigen-specific cytotoxicity by a T lymphocyte (T cell) in a microfluidic device, the kit comprising: a microfluidic device comprising a flow region for containing a flow of a first fluidic medium and a chamber opening to the flow region; and a cytotoxicity detection reagent configured to detect viability of a target cell.

Embodiment 501. The kit of embodiment 500, wherein the cytotoxicity detection reagent comprises a reagent configured to label an apoptotic cell.

Embodiment 502. The kit of embodiment 500, wherein the cytotoxicity detection reagent comprises a reagent configured to detect calcium flux or mitochondrial membrane potential.

Embodiment 503. The kit of any one of embodiments 500 to 502, further comprising a first capture object configured to capture a first secreted biomolecule of a T cell.

Embodiment 504. The kit of embodiment 503, further comprising a first biomolecule detection reagent configured to detect the first secreted biomolecule, wherein the reagent is configured to produce a colorimetric, luminescent, or fluorescent signal.

Embodiment 505. The kit of any one of embodiments 500 to 504, wherein the microfluidic device further comprises a microfluidic channel.

Embodiment 506. The kit of any one of embodiments 500 to 505, wherein the chamber comprises a sequestration pen, wherein the sequestration pen comprises an isolation region for containing a second fluidic medium, the isolation region having a single opening, wherein the isolation region of the sequestration pen is an unswept region of the microfluidic device; and a connection region fluidically connecting the isolation region to the flow region.

Embodiment 507. The kit of any one of embodiments 500 to 506, wherein the flow region is a microfluidic channel.

Embodiment 508. The kit of any one of embodiments 500 to 507, wherein the microfluidic device further comprises an electrode activation substrate.

Embodiment 509. The kit of embodiment 508, wherein the electrode activation substrate is configured to generate DEP forces.

Embodiment 510. The kit of any one of embodiments 503 to 509, further comprising a second capture object, and, optionally, a second secreted biomolecule detection reagent, wherein the second secreted biomolecule is different from the first secreted biomolecule.

Embodiment 511. The kit of any one of embodiments 500 to 510, further comprising at least one reagent configured to label a cell surface marker of a T cell, wherein the cell surface marker is associated with proliferation, activation, metabolic activity, memory, exhaustion and/or lineage.

Embodiment 1. A method for automated detection of micro-objects in an illuminated image (e.g., a bright field image), the method including: generating a plurality of pixel masks from the image for a corresponding plurality of micro-object characteristics, wherein generating the plurality of pixel masks comprises processing pixel data from the image using a machine learning algorithm, and wherein each pixel mask comprises a set of pixel annotations, each pixel annotation of the set representing a probability that a corresponding pixel in the image represents the corresponding micro-object characteristic; and obtaining a micro-object count from at least one pixel mask of the plurality of pixel masks.

Embodiment 2. The method of embodiment 1, wherein the micro-object count is obtained from a combination of pixel masks of the plurality of pixel masks.

Embodiment 3. The method of embodiment 1 or 2, wherein the plurality of micro-object characteristics comprises at least three micro-object characteristics.

Embodiment 4. The method of embodiment 1 or 2, wherein the plurality of micro-object characteristics comprises at least: (i) micro-object center; (ii) micro-object edge; and (iii) non-micro-object.

Embodiment 5. The method of embodiment 4, wherein obtaining a micro-object count comprises obtaining a micro-object count from the pixel mask corresponding to the micro-object center characteristic or a combination of pixel masks that includes the pixel mask corresponding to the micro-object center characteristic.

Embodiment 6. The method of any one of embodiments 1 to 5, wherein the machine learning algorithm comprises a neural network (e.g., a convolutional neural network).

Embodiment 7. The method of embodiment 6, wherein the neural network comprises a plurality of down-sampling blocks (e.g., at least 2, 3, 4, etc. down-sampling blocks), each down-sampling block including a first down-sampling convolutional layer, a first batch normalization layer, and a first ELU layer including a gating function, and wherein each of the first down-sampling convolutional layers reduces the spatial resolution of image data that it receives.

Embodiment 8. The method of embodiment 7, wherein one or more (e.g., each) of the down-sampling blocks consists of (or consists essentially of) the first down-sampling convolutional layer, the first batch normalization layer, and the first ELU layer, wherein the first ELU layer receives image data directly from the first batch normalization layer, and wherein the first batch normalization layer receives image data directly from the first down-sampling convolutional layer.

Embodiment 9. The method of embodiment 7 or 8, wherein each down-sampling convolution layer reduces spatial resolution of the image data that it receives by a factor of 2 (e.g., by sliding a convolutional filter (or kernel) two pixels at a time).

Embodiment 10. The method of any one of embodiments 7 to 9, wherein each of the first down-sampling convolutional layers comprises a 5×5 convolutional filter.

Embodiment 11. The method of any one of embodiments 7 to 10, wherein one or more (e.g., each) down-sampling blocks of the plurality is followed by a residual network block having a branched structure.

Embodiment 12. The method of embodiment 11, wherein the branched structure of the residual network block comprises a first branch and a second branch, and wherein the first branch processes image data received from a preceding down-sampling block to a lesser extent than the second branch.

Embodiment 13. The method of embodiment 12, wherein the first branch of the residual network block comprises a second convolutional layer, a second batch normalization layer, and a second ELU layer including a gating function.

Embodiment 14. The method of embodiment 13, wherein the first branch of the residual network block consists of (or consists essentially of) the second convolutional layer, the second batch normalization layer, and the second ELU layer, wherein the second ELU layer receives image data directly from the second batch normalization layer, and wherein the second batch normalization layer receives image data directly from the second convolutional layer.

Embodiment 15. The method of embodiment 13 or 14, wherein the second convolution layer comprises a 1×1 convolutional filter.

Embodiment 16. The method of any one of embodiments 11 to 15, wherein the second branch of the residual network block comprises two or more processing units, wherein each processing unit comprises a convolutional layer and a batch normalization layer.

Embodiment 17. The method of embodiment 16, wherein the second branch of the residual network block consists of (or consists essentially of) a third convolutional layer, a third batch normalization layer, a third ELU layer including a gating function, a fourth convolutional layer, and a fourth batch normalization layer, wherein the fourth batch normalization layer receives image data directly from the fourth convolutional layer, wherein the fourth convolutional layer receives image data directly from the third ELU layer, wherein the third ELU layer receives image data directly from the third batch normalization layer, and wherein the third batch normalization layer receives image data directly from the third convolutional layer.

Embodiment 18. The method of embodiment 16 or 17, wherein the third convolution layer comprises a 3×3 convolutional filter.

Embodiment 19. The method of embodiment 17 or 18, wherein the fourth convolutional layer comprises a 3×3 convolutional filter.

Embodiment 20. The method of any one of embodiments 11 to 19, wherein image data from the first branch of the residual network block (e.g., the ELU layer of the first branch) and the second branch of the residual network block (e.g., the fourth batch normalization layer of the second branch) is recombined and transferred to a fourth ELU layer including a gating function.

Embodiment 21. The method of any one of embodiments 6 to 20, wherein the neural network comprises a first down-sampling block, a first residual network block, a second down-sampling block, a second residual network block, a third down-sampling block, and a third residual network block.

Embodiment 22. The method of embodiment 21, wherein the first down-sampling block and the first residual network block each comprise 32 channels and a spatial resolution that is one-half the spatial resolution of the image.

Embodiment 23. The method of embodiment 21 or 22, wherein the second down-sampling block and the second residual network block each comprise 64 channels and a spatial resolution that is one-quarter the resolution of the image.

Embodiment 24. The method of any one of embodiments 21 to 23, wherein the third down-sampling block and the third residual network block each comprise 128 channels and a spatial resolution that is one-eighth the resolution of the image.

Embodiment 25. The method of any one of embodiments 7 to 24, wherein the neural network comprises an up-sampling block for each down-sampling block of the plurality, each up-sampling block including a transpose convolutional layer, an up-sampling batch normalization layer, and an up-sampling ELU layer including a gating function, and wherein the transpose convolutional layer of each up-sampling block increases the spatial resolution of image data that it receives.

Embodiment 26. The method of embodiment 25, wherein each of one or more of the up-sampling blocks comprises a recombination layer in which image data from the up-sampling batch normalization layer is merged with image data from a preceding residual network block.

Embodiment 27. The method of embodiment 26, wherein each of the one or more up-sampling blocks consists of (or consists essentially of) the transpose convolutional layer, the up-sampling batch normalization layer, the recombination layer, and the up-sampling ELU layer, wherein the up-sampling ELU layer receives image data directly from the recombination layer, and wherein the up-sampling batch normalization layer receives image data directly from the reconstructive transpose layer.

Embodiment 28. The method of any one of embodiments 25 to 27, wherein each transpose convolution layer increases spatial resolution of image data that it receives by a factor of 2.

Embodiment 29. The method of embodiment 27 or 28, wherein, when the neural network has n down-sampling blocks and n residual network blocks, the network has n−1 up-sampling blocks that include a recombination layer.

Embodiment 30. The method of any one of embodiments 25 to 29, wherein the neural network comprises a first up-sampling block having a recombination layer that receives image data from a second residual network block, a second up-sampling block having a recombination layer that receives image data from a first residual network block, and a third up-sampling block that does not include a recombination layer.

Embodiment 31. The method of embodiment 30, wherein the first up-sampling block comprises 64 channels and outputs image data having a spatial resolution that is one-fourth the spatial resolution of the image.

Embodiment 32. The method of embodiment 30 or 31, wherein the second up-sampling block comprises 32 channels and outputs image data having a spatial resolution that is one-half the spatial resolution of the image.

Embodiment 33. The method of any one of embodiments 30 to 32, wherein the third up-sampling block comprises 3 channels and outputs image data having a spatial resolution that is the same as the resolution of the image.

Embodiment 34. The method of any one of embodiments 6 to 33, wherein the neural network has a structure substantially the same as shown in FIGS. 5A-D.

Embodiment 35. The method of any one of embodiments 1 to 34 further including pre-processing the image prior to generating the plurality of pixel masks.

Embodiment 36. The method of embodiment 35, wherein the micro-objects are imaged within a microfluidic device, and wherein the pre-processing comprises subtracting out a repeating pattern produced by at least one component of the microfluidic device during imaging.

Embodiment 37. The method of embodiment 36, wherein the pre-processing comprises applying a Fourier transform to the image to identify the repeating pattern.

Embodiment 38. The method of embodiment 36 or 37, wherein the at least one component of the microfluidic device is a substrate surface.

Embodiment 39. The method of any one of embodiments 36 to 38, wherein the at least one component of the microfluidic device is a substrate surface including a photo-transistor array.

Embodiment 40. The method of any one of embodiments 35 to 39, wherein pre-processing the image comprises flipping and/or rotating the image into a desired orientation.

Embodiment 41. The method of any one of embodiments 35 to 40, wherein pre-processing the image comprises leveling brightness across the image (e.g., using a polynomial best-fit correction, such as a quadratic or higher order polynomial best-fit correction).

Embodiment 42. The method of any one of embodiments 35 to 41, wherein pre-processing the image comprises correcting for distortion introduced in the image during the imaging process (e.g., using a lookup table computed by examining a corresponding image of a dot array having known spacing between the dots).

Embodiment 43. The method of any one of embodiments 35 to 42, wherein pre-processing the image comprises applying a contrast enhancement.

Embodiment 44. The method of any one of embodiments 1 to 43 further including: classifying the micro-objects identified in the micro-object count into at least one of a plurality of micro-object types.

Embodiment 45. The method of any one of embodiments 6 to 44 further including: training the neural network using a set of training images that contain micro-objects.

Embodiment 46. The method of embodiment 45, wherein the training images are used in conjunction with training data obtained from manual visual review of the training images.

Embodiment 47. The method of embodiment 45 or 46, wherein the training images are used in conjunction with training data obtained from computer validated images containing micro-objects of a same type and/or number.

Embodiment 48. The method of any one of embodiments 1 to 47, wherein the micro-objects are biological cells.

Embodiment 49. The method of embodiment 48, wherein the biological cells are immunological cells (e.g., T cells, B cells, NK cells, macrophages, or the like).

Embodiment 50. The method of embodiment 49, wherein the biological cells are cells from a cell line (e.g., CHO cells) or cancer cells.

Embodiment 51. The method of embodiment 49, wherein the biological cells are oocytes, sperm, or embryos.

Embodiment 52. A non-transitory computer-readable medium in which a program is stored for causing a system comprising a computer to perform a method for automatically detecting micro-objects in an illuminated image (e.g., a bright field image), the method including: storing, in a memory, an image which may include one or more micro-objects; generating a plurality of pixel masks from the image for a corresponding plurality of micro-object characteristics; and obtaining a micro-object count from at least one pixel mask of the plurality of pixel masks, wherein the steps of generating and obtaining are performed according to any one of embodiments 1 to 51 or 93 to 128.

Embodiment 53. The method of the non-transitory computer-readable medium of embodiment 52, wherein the micro-object count is for micro-objects that are disposed within a micro-fluidic device.

Embodiment 54. The method of the non-transitory computer-readable medium of embodiment 52 or 53, wherein the method further comprises pre-processing the image, wherein the pre-processing is performed prior to generating the plurality of pixel masks.

Embodiment 55. The method of the non-transitory computer-readable medium of embodiment 54, wherein the micro-objects were imaged within a microfluidic device, and wherein pre-processing the image comprises subtracting out a repeating pattern produced by at least one component of the microfluidic device during imaging.

Embodiment 56. The method of the non-transitory computer-readable medium of embodiment 55, wherein the pre-processing comprises applying a Fourier transform to the image to identify the repeating pattern.

Embodiment 57. The method of the non-transitory computer-readable medium of embodiment 55 or 56, wherein the at least one component of the microfluidic device is a substrate surface.

Embodiment 58. The method of the non-transitory computer-readable medium of embodiment 55 or 56, wherein the at least one component of the microfluidic device is a photo-transistor array.

Embodiment 59. The method of the non-transitory computer-readable medium of any one of embodiments 52 to 58, wherein the plurality of micro-object characteristics includes micro-object center, micro-object border, and non-micro-object.

Embodiment 60. The method of the non-transitory computer-readable medium of any one of embodiments 52 to 58, wherein the plurality of corresponding micro-object characteristics are cellular characteristics.

Embodiment 61. The method of the non-transitory computer-readable medium of embodiment 60, wherein the cellular characteristics include a cell center, a cell border, and non-cell.

Embodiment 62. The method of the non-transitory computer-readable medium of any one of embodiments 52 to 61, wherein the micro-objects being counted are biological cells.

Embodiment 63. The method of the non-transitory computer-readable medium of embodiment 62, wherein the biological cells are immunological cells (e.g., T cells, B cells, NK cells, macrophages, or the like).

Embodiment 64. The method of the non-transitory computer-readable medium of embodiment 62, wherein the biological cells are cells from a cell line (e.g., CHO cells) or cancer cells.

Embodiment 65. The method of the non-transitory computer-readable medium of embodiment 62, wherein the biological cells are oocytes, sperm, or embryos.

Embodiment 66. The method of the non-transitory computer-readable medium of any one of embodiments 52 to 65, wherein the step of generating is performed in a first module.

Embodiment 67. The method of the non-transitory computer-readable medium of any one of embodiments 52 to 66, wherein the step of obtaining is performed in a second module.

Embodiment 68. The method of the non-transitory computer-readable medium of any one of embodiments 52 to 65, wherein the steps of generating and obtaining are performed in a single module.

Embodiment 69. A method of re-positioning micro-objects in a microfluidic device including a plurality of sequestration pens, the method including: identifying a set of micro-objects disposed within the microfluidic device, wherein the set of micro-objects is identified according to the method of any one of embodiments 1 to 51 or 93 to 128; computing one or more trajectories, wherein each trajectory is a path that connects one micro-object of the set of micro-objects with one sequestration pen of the plurality of sequestration pens; selecting, for one or more micro-objects of the set of micro-objects, a trajectory from the one or more trajectories; and re-positioning at least one micro-object of the one or more micro-objects having a selected trajectory by moving the micro-object along its selected trajectory (e.g., re-positioning can be performed using DEP force, which can be activated as disclosed herein or any other technique known in the art).

Embodiment 70. The method of embodiment 69, wherein re-positioning at least one micro-object of the one or more micro-objects having a selected trajectory comprises moving a first micro-object along its selected trajectory and moving a second micro-object along its selected trajectory.

Embodiment 71. The method of embodiment 70, wherein the first and second micro-objects are moved along their selected trajectories in parallel.

Embodiment 72. The method of any one of embodiments 69 to 71, further including: computing a density value associated with the set of micro-objects; and computing the one or more trajectories based, at least in part, on the density value associated with the set of micro-objects.

Embodiment 73. The method of embodiment 72, further including: determining that the density value exceeds a threshold value; and computing, for a first micro-object of the set of micro-objects, one or more trajectories connecting the first micro-object with one or more sequestration pens of the plurality of sequestration pens.

Embodiment 74. The method of embodiment 72, further including: determining that the density value does not exceed a threshold value; and computing, for a first sequestration pen of the plurality of sequestration pens, one or more trajectories connecting the first sequestration pen with one or more micro-objects of the set of micro-objects.

Embodiment 75. The method of any one of embodiments 69 to 74, further including identifying empty sequestration pens amongst the plurality of sequestration pens, wherein the one or more computed trajectories connect one micro-object of the set of micro-objects with one empty sequestration pen of the plurality of sequestration pens.

Embodiment 76. The method of any one of embodiments 69 to 75, wherein selecting a trajectory of the one or more trajectories comprises selecting a trajectory for each micro-object that is being repositioned such that the sum of the lengths of the selected trajectories is minimized.

Embodiment 77. The method of embodiment 76, wherein minimizing the sum of the lengths of the selected trajectories comprises using at least one of the following: a greedy algorithm, a heuristics-based algorithm, a non-linear algorithm, and a constrained search.

Embodiment 78. The method of any one of embodiments 69 to 77, wherein selecting a trajectory of the one or more trajectories further comprises determining whether the trajectory exceeds a pre-determined maximum length.

Embodiment 79. The method of any one of embodiments 69 to 78, wherein re-positioning at least one micro-object of the one or more micro-objects comprises accelerating each of the at least one micro-objects from an initial velocity to a traveling velocity over a first time period.

Embodiment 80. The method of embodiment 69, wherein re-positioning at least one micro-object of the one or more micro-objects comprises decelerating each of the at least one micro-objects from the traveling velocity to a final velocity over a second time period.

Embodiment 81. A method of re-positioning micro-objects in a microfluidic device, the method including: identifying a set of micro-objects disposed within a specified spatial region of the microfluidic device, wherein the set of micro-objects are identified according to the method of any one of embodiments 1 to 51 or 93 to 128; calculating a set of vertices that divide the specified spatial region into sub-regions, each of which contains one or more micro-object(s) of the set of micro-objects; generating a first light cage for a first micro-object of the set of micro-objects based on the calculated set of vertices; and moving the first light cage relative to the specified spatial region of the microfluidic device to re-position the first micro-object (e.g., can generate a plurality of light cages for a corresponding plurality of micro-objects, then move the plurality of light cages relative to the specified spatial region of the microfluidic device).

Embodiment 82. The method of embodiment 81, wherein calculating the set of vertices comprises calculating a set of vertices that divide the specified spatial region into sub-regions, wherein at least a subset of the sub-regions contains a single micro-object of the set of micro-objects.

Embodiment 83. The method of embodiment 81 or 82, wherein calculating the set of vertices comprises: calculating a Delaunay triangulation of the set of micro-objects; generating a Voronoi diagram based on the Delaunay triangulation of the set of micro-objects; and identifying the set of vertices based on the Voronoi diagram.

Embodiment 84. The method of any one of embodiments 81 to 83, wherein generating the first light cage comprises: generating a plurality of light bars that link a subset of vertices of the set of vertices, wherein the sub-set of vertices comprises (or consists of) vertices which are most proximal to and surround the first micro-object.

Embodiment 85. The method of embodiment 84, further including shrinking the size of the first light cage to thereby separate the first micro-object from other micro-objects and/or light cages in the specified spatial region.

Embodiment 86. The method of any one of embodiments 81 to 83, wherein generating the first light cage comprises: computing, for the first micro-object of the set of micro-objects, an initial light cage; computing the intersection between the initial light cage and the set of vertices; and generating a modified first light cage based on the intersection between the initial light cage and the set of vertices.

Embodiment 87. The method of any of embodiments 81 to 86, further including: generating a second light cage for a second micro-object of the set of micro-objects based on the calculated set of vertices.

Embodiment 88. The method of embodiment 87, further including moving both the first modified light cage and the second modified light cage relative to the specified spatial region of the microfluidic device to physically separate the first micro-object and the second micro-object.

Embodiment 89. The method of embodiment 88, wherein the first micro-object and the second micro-object are initially located in adjacent sub-regions of the specified spatial region.

Embodiment 90. The method of any one of embodiments 81 to 89, wherein the micro-object of interest is a cell.

Embodiment 91. The method of embodiment 90, wherein the cell is a mammalian cell.

Embodiment 92. The method of embodiment 90 or 91, wherein the cell is selected from the group consisting of a blood cell, a hybridoma, a cancer cell, and a transformed cell.

Embodiment 93. A method for automatically detecting micro-objects in an illuminated image (e.g., a bright field image), the method including: receiving image data of a microfluidic device; pre-processing the image data to reduce anomalies in the image data; processing pixel data in the image data using a neural network to annotate the pixel data according to a plurality of micro-object characteristics and output probability values for each pixel in the pixel data; applying a threshold to determine which pixel probabilities at least meet a defined threshold; and determining a micro-object count based on number of micro-objects identifiable after threshold application.

Embodiment 94. The method of embodiment 93, wherein the neural network comprises a down-sampling block, the down-sampling block including a down-sampling convolutional layer, a down-sampling batch normalization layer, and a down-sampling activation layer.

Embodiment 95. The method of embodiment 93, wherein the neural network comprises a plurality of down-sampling blocks, each down-sampling block including a down-sampling convolutional layer, a down-sampling batch normalization layer, and a down-sampling activation layer.

Embodiment 96. The method of embodiment 94 or 95, wherein each down-sampling convolution layer reduces spatial resolution of image data by a factor of 2.

Embodiment 97. The method of embodiment 94 or 95, wherein each down-sampling convolution layer reduces spatial resolution of image data by a factor of 2, and wherein each down-sampling convolutional layer comprises a 5×5 convolutional filter.

Embodiment 98. The method of embodiment 94 or 95, wherein one or more down-sampling blocks of the plurality is followed by a residual network block having a branched structure.

Embodiment 99. The method of embodiment 98, wherein the branched structure of the residual network block comprises a first branch and a second branch, and wherein the first branch processes image data received from a preceding down-sampling block to a lesser extent that the second branch.

Embodiment 100. The method of embodiment 99, wherein the first branch of the residual network block comprises a first branch convolutional layer, a first branch batch normalization layer, and a first branch activation layer.

Embodiment 101. The method of embodiment 100, wherein the first branch activation layer receives image data directly from the first branch batch normalization layer, and wherein the first branch batch normalization layer receives image data directly from the first branch convolutional layer.

Embodiment 102. The method of embodiments 100 or 101, wherein the first branch convolution layer comprises a 1×1 convolutional filter.

Embodiment 103. The method of any one of embodiments 99 to 102, wherein the second branch of the residual network block comprises two or more processing units, wherein each processing unit comprises a residual convolutional layer and a residual batch normalization layer.

Embodiment 104. The method of embodiment 103, wherein the second branch of the residual network block comprises a first residual convolutional layer, a first residual batch normalization layer, a second branch activation layer, a second residual convolutional layer, and a second residual batch normalization layer, wherein the second residual batch normalization layer receives image data directly from the second residual convolutional layer, wherein the second residual convolutional layer receives image data directly from the second branch activation layer, wherein the second branch activation layer receives image data directly from the first residual batch normalization layer, and wherein the first residual batch normalization layer receives image data directly from the first residual convolutional layer.

Embodiment 105. The method of embodiment 104, wherein the first residual convolution layer comprises a first residual convolutional filter and the second residual convolution layer comprises a second residual convolutional filter, and wherein the first and second residual convolutional filters have different dimensions.

Embodiment 106. The method of embodiment 104, wherein the first residual convolution layer comprises a first residual convolutional filter and the second residual convolution layer comprises a second residual convolutional filter, and wherein the first and second residual convolutional filters have the same dimensions.

Embodiment 107. The method of any one of embodiments 99 to 106, wherein image data from the first branch and the second branch is recombined and transferred to a residual network activation layer.

Embodiment 108. The method of any one of embodiments 94 to 107, wherein the neural network comprises a first down-sampling block, a first residual network block, a second down-sampling block, a second residual network block, a third down-sampling block, and a third residual network block.

Embodiment 109. The method of embodiment 108, wherein the first down-sampling block and the first residual network block each comprise 32 channels and a spatial resolution that is one-half the spatial resolution of the image.

Embodiment 110. The method of embodiment 108 or 109, wherein the second down-sampling block and the second residual network block each comprise 64 channels and a spatial resolution that is one-quarter the resolution of the image.

Embodiment 111. The method of any one of embodiments 108 to 110, wherein the third down-sampling block and the third residual network block each comprise 128 channels and a spatial resolution that is one-eighth the resolution of the image.

Embodiment 112. The method of any one of embodiments 95 to 111, wherein the neural network comprises an up-sampling block for each down-sampling block of the plurality, each up-sampling block including a transpose convolutional layer, an up-sampling batch normalization layer, and an up-sampling activation layer, and wherein the transpose convolutional layer of each up-sampling block increases the spatial resolution of image data that it receives.

Embodiment 113. The method of embodiment 112, wherein one or more of the up-sampling blocks comprises a recombination layer in which image data from the up-sampling batch normalization layer is merged with image data from a preceding residual network block.

Embodiment 114. The method of embodiment 113, wherein one or more up-sampling blocks comprises the transpose convolutional layer, the up-sampling batch normalization layer, the recombination layer, and the up-sampling activation layer, wherein the up-sampling activation layer receives image data directly from the recombination layer, wherein the recombination layer receives image data directly from the up-sampling batch normalization layer, and wherein the up-sampling batch normalization layer receives image data directly from the transpose convolutional layer.

Embodiment 115. The method of any one of embodiments 112 to 114, wherein each transpose convolution layer increases spatial resolution of image data by a factor of 2.

Embodiment 116. The method of embodiment 113 or 114, wherein, when the neural network has n down-sampling blocks and n residual network blocks, the network has n−1 up-sampling blocks that include a recombination layer.

Embodiment 117. The method of any one of embodiments 113 to 116, wherein the neural network comprises a first up-sampling block having a recombination layer that receives image data from a second residual network block, a second up-sampling block having a recombination layer that receives image data from a first residual network block, and a third up-sampling block that does not include a recombination layer.

Embodiment 118. The method of embodiment 117, wherein the first up-sampling block comprises 64 channels and outputs image data having a spatial resolution that is one-fourth the spatial resolution of the image.

Embodiment 119. The method of embodiment 117 or 118, wherein the second up-sampling block comprises 32 channels and outputs image data having a spatial resolution that is one-half the spatial resolution of the image.

Embodiment 120. The method of any one of embodiments 117 to 120, wherein the third up-sampling block comprises 3 channels and outputs image data having a spatial resolution that is the same as the resolution of the image.

Embodiment 121. The method of any one of embodiments 93 to 120, further including: classifying the micro-objects into at least one of a plurality of micro-object types.

Embodiment 122. The method of any one of embodiments 93 to 121, further including: training the neural network using a set of training images that contain micro-objects.

Embodiment 123. The method of embodiment 122, wherein the training images are used in conjunction with training data obtained from manual visual review of the training images.

Embodiment 124. The method of embodiment 122 or 123, wherein the training images are used in conjunction with training data obtained from computer validated images containing micro-objects of a same type and/or number.

Embodiment 125. The method of any one of embodiments 93 to 124, wherein the micro-objects are biological cells.

Embodiment 126. The method of embodiment 125, wherein the biological cells are immunological cells.

Embodiment 127. The method of embodiment 125, wherein the biological cells are cells from a cell line or cancer cells.

Embodiment 128. The method of embodiment 125, wherein the biological cells are oocytes, sperm, or embryos.

Embodiment 129. A non-transitory computer-readable medium in which a program is stored for causing a system comprising a computer to perform a method for automatically detecting micro-objects in an illuminated image (e.g., a bright field image), the method including: receiving image data of a microfluidic device; pre-processing the image data to reduce anomalies in the image data; processing pixel data in the image data using a neural network to annotate the pixel data according to a plurality of micro-object characteristics and output probability values for each pixel in the pixel data; applying a threshold to determine which pixel probabilities at least meet a defined threshold; and determining a micro-object count based on number of micro-objects identifiable after threshold application.

Embodiment 130. The method of the non-transitory computer-readable medium of embodiment 129, wherein the neural network comprises a down-sampling block, the down-sampling block including a down-sampling convolutional layer, a down-sampling batch normalization layer, and a down-sampling activation layer.

Embodiment 131. The method of the non-transitory computer-readable medium of embodiment 129, wherein the neural network comprises a plurality of down-sampling blocks, each down-sampling block including a down-sampling convolutional layer, a down-sampling batch normalization layer, and a down-sampling activation layer.

Embodiment 132. The method of the non-transitory computer-readable medium of embodiments 130 or 131, wherein each down-sampling convolution layer reduces spatial resolution of image data by a factor of 2.

Embodiment 133. The method of the non-transitory computer-readable medium of embodiments 130 or 131, wherein each down-sampling convolution layer reduces spatial resolution of image data by a factor of 2, and wherein each down-sampling convolutional layer comprises a 5×5 convolutional filter.

Embodiment 134. The method of the non-transitory computer-readable medium of embodiments 130 or 131, wherein one or more down-sampling blocks of the plurality is followed by a residual network block having a branched structure.

Embodiment 135. The method of the non-transitory computer-readable medium of embodiment 134, wherein the branched structure of the residual network block comprises a first branch and a second branch, and wherein the first branch processes image data received from a preceding down-sampling block to a lesser extent that the second branch.

Embodiment 136. The method of the non-transitory computer-readable medium of embodiment 135, wherein the first branch of the residual network block comprises a first branch convolutional layer, a first branch batch normalization layer, and a first branch activation layer.

Embodiment 137. The method of the non-transitory computer-readable medium of embodiment 136, wherein the first branch activation layer receives image data directly from the first branch batch normalization layer, and wherein the first branch batch normalization layer receives image data directly from the first branch convolutional layer.

Embodiment 138. The method of the non-transitory computer-readable medium of embodiments 136 or 137, wherein the first branch convolution layer comprises a 1×1 convolutional filter.

Embodiment 139. The method of the non-transitory computer-readable medium of any one of embodiments 135 to 137, wherein the second branch of the residual network block comprises two or more processing units, wherein each processing unit comprises a residual convolutional layer and a residual batch normalization layer.

Embodiment 140. The method of the non-transitory computer-readable medium of embodiment 139, wherein the second branch of the residual network block comprises a first residual convolutional layer, a first residual batch normalization layer, a second branch activation layer, a second residual convolutional layer, and a second residual batch normalization layer, wherein the second residual batch normalization layer receives image data directly from the second residual convolutional layer, wherein the second residual convolutional layer receives image data directly from the second branch activation layer, wherein the second branch activation layer receives image data directly from the first residual batch normalization layer, and wherein the first residual batch normalization layer receives image data directly from the first residual convolutional layer.

Embodiment 141. The method of the non-transitory computer-readable medium of embodiment 140, wherein the first residual convolution layer comprises a first residual convolutional filter and the second residual convolution layer comprises a second residual convolutional filter, and wherein the first and second residual convolutional filters have different dimensions.

Embodiment 142. The method of the non-transitory computer-readable medium of embodiment 140 wherein the first residual convolution layer comprises a first residual convolutional filter and the second residual convolution layer comprises a second residual convolutional filter, and wherein the first and second residual convolutional filters have the same dimensions.

Embodiment 143. The method of the non-transitory computer-readable medium of any one of embodiments 135 to 142, wherein image data from the first branch and the second branch is recombined and transferred to a residual network activation layer.

Embodiment 144. The method of the non-transitory computer-readable medium of any one of embodiments 129 to 143, wherein the neural network comprises a first down-sampling block, a first residual network block, a second down-sampling block, a second residual network block, a third down-sampling block, and a third residual network block.

Embodiment 145. The method of the non-transitory computer-readable medium of embodiment 144, wherein the first down-sampling block and the first residual network block each comprise 32 channels and a spatial resolution that is one-half the spatial resolution of the image.

Embodiment 146. The method of the non-transitory computer-readable medium of embodiments 144 or 145, wherein the second down-sampling block and the second residual network block each comprise 64 channels and a spatial resolution that is one-quarter the resolution of the image.

Embodiment 147. The method of the non-transitory computer-readable medium of any one of embodiments 144 to 146, wherein the third down-sampling block and the third residual network block each comprise 128 channels and a spatial resolution that is one-eighth the resolution of the image.

Embodiment 148. The method of the non-transitory computer-readable medium of any one of embodiments 131 to 147, wherein the neural network comprises an up-sampling block for each down-sampling block of the plurality, each up-sampling block including a transpose convolutional layer, an up-sampling batch normalization layer, and an up-sampling activation layer, and wherein the transpose convolutional layer of each up-sampling block increases the spatial resolution of image data that it receives.

Embodiment 149. The method of the non-transitory computer-readable medium of embodiment 148, wherein one or more of the up-sampling blocks comprises a recombination layer in which image data from the up-sampling batch normalization layer is merged with image data from a preceding residual network block.

Embodiment 150. The method of the non-transitory computer-readable medium of embodiment 149, wherein one or more up-sampling blocks comprises the transpose convolutional layer, the up-sampling batch normalization layer, the recombination layer, and the up-sampling activation layer, wherein the up-sampling activation layer receives image data directly from the recombination layer, wherein the recombination layer receives image data directly from the up-sampling batch normalization layer, and wherein the up-sampling batch normalization layer receives image data directly from the transpose convolutional layer.

Embodiment 151. The method of the non-transitory computer-readable medium of any one of embodiments 148 to 150, wherein each transpose convolution layer increases spatial resolution of image data by a factor of 2.

Embodiment 152. The method of the non-transitory computer-readable medium of embodiment 149 or 150, wherein, when the neural network has n down-sampling blocks and n residual network blocks, the network has n−1 up-sampling blocks that include a recombination layer.

Embodiment 153. The method of the non-transitory computer-readable medium of any one of embodiments 149 to 151, wherein the neural network comprises a first up-sampling block having a recombination layer that receives image data from a second residual network block, a second up-sampling block having a recombination layer that receives image data from a first residual network block, and a third up-sampling block that does not include a recombination layer.

Embodiment 154. The method of the non-transitory computer-readable medium of embodiment 153, wherein the first up-sampling block comprises 64 channels and outputs image data having a spatial resolution that is one-fourth the spatial resolution of the image.

Embodiment 155. The method of the non-transitory computer-readable medium of embodiment 153 or 154, wherein the second up-sampling block comprises 32 channels and outputs image data having a spatial resolution that is one-half the spatial resolution of the image.

Embodiment 156. The method of the non-transitory computer-readable medium of any one of embodiments 153 to 155, wherein the third up-sampling block comprises 3 channels and outputs image data having a spatial resolution that is the same as the resolution of the image.

Embodiment 157. The method of the non-transitory computer-readable medium of any one of embodiments 129 to 156, further including: classifying the micro-objects into at least one of a plurality of micro-object types.

Embodiment 158. The method of the non-transitory computer-readable medium of any one of embodiments 129 to 157, further including: training the neural network using a set of training images that contain micro-objects.

Embodiment 159. The method of the non-transitory computer-readable medium of embodiment 158, wherein the training images are used in conjunction with training data obtained from manual visual review of the training images.

160. The method of the non-transitory computer-readable medium of embodiment 158 or 159, wherein the training images are used in conjunction with training data obtained from computer validated images containing micro-objects of a same type and/or number.

Embodiment 161. The method of the non-transitory computer-readable medium of any one of embodiments 129 to 160, wherein the micro-objects are biological cells.

Embodiment 162. The method of the non-transitory computer-readable medium of embodiment 161, wherein the biological cells are immunological cells.

Embodiment 163. The method of the non-transitory computer-readable medium of embodiment 161, wherein the biological cells are cells from a cell line or cancer cells.

Embodiment 164. The method of the non-transitory computer-readable medium of embodiment 161, wherein the biological cells are oocytes, sperm, or embryos.

Embodiment 165. A system for automatically detecting micro-objects in an image, including: an image acquisition unit, including: an imaging element configured to capture one or more images of a microfluidic device, and an image pre-processing engine configured to reduce anomalies in the image data; and a micro-object detection unit communicatively connected to the image acquisition unit, including: a neural network configured to annotate pixel data in an image according to a plurality of micro-object characteristics and output probability values for each pixel in the pixel data; a threshold engine configured to determine which pixel probabilities at least meet a defined threshold, and a detection engine configured to apply image post-processing techniques and output a micro-object count.

Embodiment 166. The system of embodiment 165, wherein the neural network comprises a down-sampling block, the down-sampling block including a down-sampling convolutional layer, a down-sampling batch normalization layer, and a down-sampling activation layer.

Embodiment 167. The system of embodiment 165, wherein the neural network comprises a plurality of down-sampling blocks, each down-sampling block including a down-sampling convolutional layer, a down-sampling batch normalization layer, and a down-sampling activation layer.

Embodiment 168. The system of embodiments 166 or 167, wherein each down-sampling convolution layer is configured to reduce spatial resolution of image data by a factor of 2.

Embodiment 169. The system of embodiments 166 or 167, wherein each down-sampling convolution layer is configured to reduce spatial resolution of image data by a factor of 2, and wherein each down-sampling convolutional layer comprises a 5×5 convolutional filter.

Embodiment 170. The system of embodiments 166 or 167, wherein one or more down-sampling blocks of the plurality is followed by a residual network block having a branched structure.

Embodiment 171. The system of embodiment 170, wherein the branched structure of the residual network block comprises a first branch and a second branch, and wherein the first branch is configured to process image data received from a preceding down-sampling block to a lesser extent that the second branch.

Embodiment 172. The system of embodiment 171, wherein the first branch of the residual network block comprises a first branch convolutional layer, a first branch batch normalization layer, and a first branch activation layer.

Embodiment 173. The system of embodiment 172, wherein the first branch activation layer is configured to receive image data directly from the first branch batch normalization layer, and wherein the first branch batch normalization layer is configured to receive image data directly from the first branch convolutional layer.

Embodiment 174. The system of embodiment 172 or 173, wherein the first branch convolution layer comprises a 1×1 convolutional filter.

Embodiment 175. The system of any one of embodiments 171 to 173, wherein the second branch of the residual network block comprises two or more processing units, wherein each processing unit comprises a residual convolutional layer and a residual batch normalization layer.

Embodiment 176. The system of embodiment 175, wherein the second branch of the residual network block comprises a first residual convolutional layer, a first residual batch normalization layer, a second branch activation layer, a second residual convolutional layer, and a second residual batch normalization layer, wherein the second residual batch normalization layer is configured to receive image data directly from the second residual convolutional layer, wherein the second residual convolutional layer is configured to receive image data directly from the second branch activation layer, wherein the second branch activation layer is configured to receive image data directly from the first residual batch normalization layer, and wherein the first residual batch normalization layer is configured to receive image data directly from the first residual convolutional layer.

Embodiment 177. The system of embodiment 176, wherein the first residual convolution layer comprises a first residual convolutional filter and the second residual convolution layer comprises a second residual convolutional filter, and wherein the first and second residual convolutional filters have different dimensions.

Embodiment 178. The system of embodiment 176, wherein the first residual convolution layer comprises a first residual convolutional filter and the second residual convolution layer comprises a second residual convolutional filter, and wherein the first and second residual convolutional filters have the same dimensions.

Embodiment 179. The system of any one of embodiments 176 to 178, wherein the residual network block further comprises a recombination later configured to recombine image data from the first branch and the second branch and transfer the output from the recombination layer to a residual network activation layer.

Embodiment 180. The system of any one of embodiments 175 to 179, wherein the neural network comprises a first down-sampling block, a first residual network block, a second down-sampling block, a second residual network block, a third down-sampling block, and a third residual network block.

Embodiment 181. The system of embodiment 180, wherein the first down-sampling block and the first residual network block each comprise 32 channels and a spatial resolution that is one-half the spatial resolution of the image.

Embodiment 182. The system of embodiments 180 or 181, wherein the second down-sampling block and the second residual network block each comprise 64 channels and a spatial resolution that is one-quarter the resolution of the image.

Embodiment 183. The system of any one of embodiments 180 to 182, wherein the third down-sampling block and the third residual network block each comprise 128 channels and a spatial resolution that is one-eighth the resolution of the image.

Embodiment 184. The system of any one of embodiments 179 to 183, wherein the neural network comprises an up-sampling block for each down-sampling block of the plurality, each up-sampling block including a transpose convolutional layer, an up-sampling batch normalization layer, and an up-sampling activation layer, and wherein the transpose convolutional layer of each up-sampling block is configured to increase the spatial resolution of image data that it receives.

Embodiment 185. The system of embodiment 184, wherein one or more of the up-sampling blocks comprises a recombination layer configured to merge image data from the up-sampling batch normalization layer with image data from a preceding residual network block.

Embodiment 186. The system of embodiment 185, wherein one or more up-sampling blocks comprises the transpose convolutional layer, the up-sampling batch normalization layer, the recombination layer, and the up-sampling activation layer, wherein the up-sampling activation layer is configured to receive image data directly from the recombination layer, wherein the recombination layer is configured to receive image data directly from the up-sampling batch normalization layer, and wherein the up-sampling batch normalization layer is configured to receive image data directly from the transpose convolutional layer.

Embodiment 187. The system of any one of embodiments 184 to 186, wherein each transpose convolution layer is configured to increase spatial resolution of image data by a factor of 2.

Embodiment 188. The system of embodiment 185 or 186, wherein, when the neural network has n down-sampling blocks and n residual network blocks, the network has n−1 up-sampling blocks that include a recombination layer.

Embodiment 189. The system of any one of embodiments 185 to 188, wherein the neural network comprises a first up-sampling block having a recombination layer that is configured to receive image data from a second residual network block, a second up-sampling block having a recombination layer that is configured to receive image data from a first residual network block, and a third up-sampling block that does not include a recombination layer.

Embodiment 190. The system of embodiment 189, wherein the first up-sampling block comprises 64 channels and outputs image data having a spatial resolution that is one-fourth the spatial resolution of the image.

Embodiment 191. The system of embodiment 189 or 190, wherein the second up-sampling block comprises 32 channels and outputs image data having a spatial resolution that is one-half the spatial resolution of the image.

Embodiment 192. The system of any one of embodiments 189 to 191, wherein the third up-sampling block comprises 3 channels and outputs image data having a spatial resolution that is the same as the resolution of the image.

Embodiment 193. The system of any one of embodiments 165 to 192, wherein the micro-objects are biological cells.

Embodiment 194. The system of embodiment 193, wherein the biological cells are immunological cells.

Embodiment 195. The system of embodiment 193, wherein the biological cells are cells from a cell line or cancer cells.

Embodiment 196. The system of embodiment 193, wherein the biological cells are oocytes, sperm, or embryos.

Embodiment 200. A method for detecting and characterizing micro-objects in an microfluidic device, the method comprising: receiving a first image and one or more second images of a region of interest in the microfluidic device; pre-processing the first image and the one or more second images to reduce anomalies in the image data; transforming each of the one or more second images to optically align the second image(s) with the first image; processing pixel data in the first image using a machine learning algorithm to detect micro-objects present in the region of interest, wherein detecting each micro-object comprises identifying a boundary of the micro-object; and detecting a signal located within each boundary of each detected micro-object in each one of the one or more second images.

Embodiment 201. The method of embodiment 200, wherein at least one of the one or more second images is a fluorescent image, and wherein the detected signal in the at least one second image is a fluorescent signal.

Embodiment 202. The method of embodiment 201, wherein each of the one or more second images is a fluorescent image, and wherein the detected signal in each of the one or more second images is a fluorescent signal.

Embodiment 203. The method of embodiment 201 or 202, wherein each fluorescent image represents fluorescent signal from a unique portion of the visible light spectrum.

Embodiment 204. The method of embodiment 203, wherein each fluorescent image represents fluorescent signal from a non-overlapping portion of the visible light spectrum.

Embodiment 205. The method of any one of embodiments 200 to 204, wherein each fluorescent detected signal is associated with a reagent that specifically binds to a biological molecule comprised by one or more of the detected micro-objects.

Embodiment 206. The method of any one of embodiments 200 to 205, wherein the pre-processing of the first image and the at least one second image reduces noise and/or optical distortion(s) introduced during generation of the first image and the at least one second image.

Embodiment 207. The method of any one of embodiments 200 to 206, wherein processing pixel data in the first image is performed according to any one of embodiments 1 to 51 or 93 to 128 (provided that the step of obtaining a micro-object count from at least one pixel mask of the plurality of pixel masks is optional).

Embodiment 208. The method of any one of embodiments 200 to 206, wherein processing pixel data in the first image to detect micro-objects present in the region of interest comprises using the machine learning algorithm to generate a plurality of pixel masks from the first image for a corresponding plurality of micro-object characteristics, wherein each pixel mask comprises a set of pixel annotations, each pixel annotation of the set representing a probability that a corresponding pixel in the image represents the corresponding micro-object characteristic.

Embodiment 209. The method of embodiment 208, wherein detecting the micro-objects comprises using a combination of pixel masks of the plurality of pixel masks.

Embodiment 210. The method of embodiment 208 or 209, wherein the plurality of micro-object characteristics comprises at least three micro-object characteristics.

Embodiment 211. The method of any one of embodiments 208 to 210, wherein the plurality of micro-object characteristics comprises at least: (i) micro-object center; (ii) micro-object edge; and (iii) non-micro-object.

Embodiment 212. The method of embodiment 211, wherein detecting the micro-objects is based upon the pixel mask corresponding to the micro-object center characteristic or a combination of pixel masks that includes the pixel mask corresponding to the micro-object center characteristic.

Embodiment 213. The method of any one of embodiments 208 to 212, wherein the machine learning algorithm comprises a neural network (e.g., a convolutional neural network).

Embodiment 214. The method of any one of embodiments 200 to 206 or 208 to 213, wherein detecting the signal comprises quantifying an amount of the signal.

Embodiment 215. The method of any one of embodiments 200 to 206 or 208 to 214, wherein there are at least two second images.

Embodiment 216. The method of any one of embodiments 200 to 206 or 208 to 214, wherein there are at least three second images.

Embodiment 217. The method of any one of embodiments 200 to 206 or 208 to 214, wherein there are at least four second images.

Embodiment 218. The method of any one of embodiments 200 to 206 or 208 to 217, where detecting each micro-object further comprises determining at least one of the cross-sectional area, the circularity, the brightness, the ratio of brightness to background, the location of the micro-object, and the distance to the a nearest neighbor micro-object.

Embodiment 219. The method of any one of embodiments 200 to 206 or 208 to 218 further comprising: grouping the detected micro-objects into sub-populations of micro-objects that share one or more of the same characteristics.

Embodiment 220. The method of embodiment 219, wherein the detected micro-objects are grouped (or "gated") into sub-populations based upon their proximity in n-dimensional space, wherein each of the n dimensions is a measurable characteristic of the micro-objects.

Embodiment 221. The method of any one of embodiments 200 to 206 or 208 to 220 further comprising: providing a visual display representing a distribution of at least one characteristic of the detected micro-objects.

Embodiment 222. The method of embodiment 221, wherein the visual display is a two-dimensional graph that represents at least two characteristics of the detected micro-objects (e.g., cross-sectional area and a first fluorescent signal, or first and second fluorescent signals).

Embodiment 223. The method of embodiment 221, wherein the visual display is a three-dimensional graph that represents at least three characteristics of the detected micro-objects (e.g., cross-sectional area and first and second fluorescent signals, or first, second, and third fluorescent signals).

Embodiment 224. The method of any one of embodiments 221 to 223, further comprising providing a user interface that allows the user to select a sub-population of the detected micro-objects and, optionally, to provide instruction(s) for repositioning the selected sub-population.

Embodiment 225. The method of any of embodiments 200 to 206 or 208 to 224, further comprising increasing or decreasing the identified boundary of the micro-object.

Embodiment 226. The method of embodiment 213, wherein the neural network comprises a plurality of down-sampling blocks (e.g., at least 2, 3, 4, etc. down-sampling blocks), each down-sampling block including a first down-sampling convolutional layer, a first batch normalization layer, and a first ELU layer including a gating function, and wherein each of the first down-sampling convolutional layers reduces the spatial resolution of image data that it receives.

Embodiment 227. The method of embodiment 226, wherein one or more (e.g., each) of the down-sampling blocks consists of (or consists essentially of) the first down-sampling convolutional layer, the first batch normalization layer, and the first ELU layer, wherein the first ELU layer receives image data directly from the first batch normalization layer, and wherein the first batch normalization layer receives image data directly from the first down-sampling convolutional layer.

Embodiment 228. The method of embodiment 226 or 227, wherein each down-sampling convolution layer reduces spatial resolution of the image data that it receives by a factor of 2 (e.g., by sliding a convolutional filter (or kernel) two pixels at a time).

Embodiment 229. The method of any one of embodiments 226 to 228, wherein each of the first down-sampling convolutional layers comprises a 5×5 convolutional filter.

Embodiment 230. The method of any one of embodiments 226 to 229, wherein one or more (e.g., each) down-sampling blocks of the plurality is followed by a residual network block having a branched structure.

Embodiment 231. The method of embodiment 230, wherein the branched structure of the residual network block comprises a first branch and a second branch, and wherein the first branch processes image data received from a preceding down-sampling block to a lesser extent than the second branch.

Embodiment 232. The method of embodiment 231, wherein the first branch of the residual network block comprises a second convolutional layer, a second batch normalization layer, and a second ELU layer including a gating function.

Embodiment 233. The method of embodiment 232, wherein the first branch of the residual network block consists of (or consists essentially of) the second convolutional layer, the second batch normalization layer, and the second ELU layer, wherein the second ELU layer receives image data directly from the second batch normalization layer, and wherein the second batch normalization layer receives image data directly from the second convolutional layer.

Embodiment 234. The method of embodiment 231 or 232, wherein the second convolution layer comprises a 1×1 convolutional filter.

Embodiment 235. The method of any one of embodiments 231 to 234, wherein the second branch of the residual network block comprises two or more processing units, wherein each processing unit comprises a convolutional layer and a batch normalization layer.

Embodiment 236. The method of embodiment 235, wherein the second branch of the residual network block consists of (or consists essentially of) a third convolutional layer, a third batch normalization layer, a third ELU layer including a gating function, a fourth convolutional layer, and a fourth batch normalization layer, wherein the fourth batch normalization layer receives image data directly from the fourth convolutional layer, wherein the fourth convolutional layer receives image data directly from the third ELU layer, wherein the third ELU layer receives image data directly from the third batch normalization layer, and wherein the third batch normalization layer receives image data directly from the third convolutional layer.

Embodiment 237. The method of embodiment 236, wherein the third convolution layer comprises a 3×3 convolutional filter.

Embodiment 238. The method of embodiment 236 or 237, wherein the fourth convolutional layer comprises a 3×3 convolutional filter.

Embodiment 239. The method of any one of embodiments 231 to 238, wherein image data from the first branch of the residual network block (e.g., the ELU layer of the first branch) and the second branch of the residual network block (e.g., the fourth batch normalization layer of the second branch) is recombined and transferred to a fourth ELU layer including a gating function.

Embodiment 240. The method of any one of embodiments 213 and 226 to 239, wherein the neural network comprises a first down-sampling block, a first residual network block, a second down-sampling block, a second residual network block, a third down-sampling block, and a third residual network block.

Embodiment 241. The method of embodiment 240, wherein the first down-sampling block and the first residual network block each comprise 32 channels and a spatial resolution that is one-half the spatial resolution of the image.

Embodiment 242. The method of embodiment 240 or 241, wherein the second down-sampling block and the second residual network block each comprise 64 channels and a spatial resolution that is one-quarter the resolution of the image.

Embodiment 243. The method of any one of embodiments 240 to 242, wherein the third down-sampling block and the third residual network block each comprise 128 channels and a spatial resolution that is one-eighth the resolution of the image.

Embodiment 244. The method of any one of embodiments 213 or 226 to 243, wherein the neural network comprises an up-sampling block for each down-sampling block of the plurality, each up-sampling block including a transpose convolutional layer, an up-sampling batch normalization layer, and an up-sampling ELU layer including a gating function, and wherein the transpose convolutional layer of each up-sampling block increases the spatial resolution of image data that it receives.

Embodiment 245. The method of embodiment 244, wherein each of one or more of the up-sampling blocks comprises a recombination layer in which image data from the up-sampling batch normalization layer is merged with image data from a preceding residual network block.

Embodiment 246. The method of embodiment 245, wherein each of the one or more up-sampling blocks consists of (or consists essentially of) the transpose convolutional layer, the up-sampling batch normalization layer, the recombination layer, and the up-sampling ELU layer, wherein the up-sampling ELU layer receives image data directly from the recombination layer, and wherein the up-sampling batch normalization layer receives image data directly from the reconstructive transpose layer.

Embodiment 247. The method of any one of embodiments 244 to 246, wherein each transpose convolution layer increases spatial resolution of image data that it receives by a factor of 2.

Embodiment 248. The method of any one of embodiments 230 to 247, wherein, when the neural network has n down-sampling blocks and n residual network blocks, the network has n−1 up-sampling blocks that include a recombination layer.

Embodiment 249. The method of any one of embodiments 213 or 226 to 248, wherein the neural network comprises a first up-sampling block having a recombination layer that receives image data from a second residual network block, a second up-sampling block having a recombination layer that receives image data from a first residual network block, and a third up-sampling block that does not include a recombination layer.

Embodiment 250. The method of embodiment 249, wherein the first up-sampling block comprises 64 channels and outputs image data having a spatial resolution that is one-fourth the spatial resolution of the image.

Embodiment 251. The method of embodiment 249 or 250, wherein the second up-sampling block comprises 32 channels and outputs image data having a spatial resolution that is one-half the spatial resolution of the image.

Embodiment 252. The method of any one of embodiments 249 to 251, wherein the third up-sampling block comprises 3 channels and outputs image data having a spatial resolution that is the same as the resolution of the image.

Embodiment 253. The method of embodiment 213, wherein the neural network has a structure substantially the same as shown in FIGS. 9A-D.

Embodiment 254. The method of any one of embodiments 213 or 226 to 253 further including pre-processing the first image prior to generating the plurality of pixel masks.

Embodiment 255. The method of embodiment 254, wherein the micro-objects are imaged within a microfluidic device, and wherein the pre-processing comprises subtracting out a repeating pattern produced by at least one component of the microfluidic device during imaging.

Embodiment 256. The method of embodiment 255, wherein the pre-processing comprises applying a Fourier transform to the image to identify the repeating pattern.

Embodiment 257. The method of embodiment 255 or 256, wherein the at least one component of the microfluidic device is a substrate surface.

Embodiment 258. The method of any one of embodiments 255 to 257, wherein the at least one component of the microfluidic device is a substrate surface including a phototransistor array.

Embodiment 259. The method of any one of embodiments 200 to 258, wherein the micro-objects are biological cells.

Embodiment 260. The method of embodiment 259, wherein the biological cells are immunological cells (e.g., T cells, B cells, NK cells, macrophages, or the like).

Embodiment 261. The method of embodiment 259, wherein the biological cells are cells from a cell line (e.g., CHO cells) or cancer cells.

Embodiment 262. The method of embodiment 259, wherein the biological cells are oocytes, sperm, or embryos.

Embodiment 263. A non-transitory computer-readable medium in which a program is stored for causing a system comprising a computer to perform a method for automatically detecting and characterizing micro-objects in a microfluidic device, the method comprising: receiving a first image and one or more second images of a region of interest in the microfluidic device; pre-processing the first image and each of the one or more second images to reduce anomalies in the image data; transforming each of the one or more second images to optically align the second image with the first image; processing pixel data in the first image using a machine learning algorithm to detect micro-objects present in the region of interest, wherein detecting each micro-object comprises identifying a boundary of the micro-object; and detecting a signal located within each boundary of each detected micro-object in each one of the one or more second images.

Embodiment 264. The non-transitory computer-readable medium of embodiment 263, wherein the program causes the system to perform the method of any one of embodiments 200 to 262.

Embodiment 265. The method of the non-transitory computer-readable medium of embodiment 263 or 264, further comprising increasing or decreasing the identified boundary of the micro-object.

Embodiment 266. The non-transitory computer-readable medium of any one of embodiments 263 to 265 further comprising the elements of the non-transitory computer-readable medium of any one of embodiments 52 to 68 or 129 to 164.

Embodiment 267. A system for automatically detecting micro-objects in a microfluidic device, comprising:

an image acquisition unit, comprising: an imaging element configured to capture a first image and one or more second images of a region of interest in the microfluidic device; an image pre-processing engine configured to reduce anomalies in the image data; and an alignment engine configured to transform the second image to optically align the second image with the first image, and a micro-object detection and characterization unit communicatively connected to the image acquisition unit, comprising: an image processing engine configured to process pixel data in the first image using a machine learning algorithm to detect micro-objects present in the region of interest, wherein detecting the micro-objects comprising identifying a boundary of each detected micro-object; and a detection engine configured to detect a signal located within each boundary of each detected micro-object in each of the one or more second images.

Embodiment 268. The system of embodiment 267 further comprising: a user interface, wherein the user interface is configured to allow the user to select a sub-population of the detected micro-objects and, optionally, to provide instruction(s) for repositioning the selected sub-population.

Embodiment 269. The system of embodiment 267 or 268, wherein the repositioning is an automated process with the system.

Embodiment 270. The system of any one of embodiments 267 to 269, wherein the micro-object detection unit is configured to perform the method of any one of embodiments 200 to 262.

Embodiment 271. The system of any one of embodiments 267 to 270, further comprising any of the elements of embodiments 165 to 196.

Embodiment 272. A computing device for characterizing and selecting micro-objects in a microfluidic device, the computing device comprising a display screen, the computing device being configured to display on the screen a menu for selecting a first parameter, selected from a provided parameter list, for characterizing a set of detected micro-objects, and the computing device being configured to display on the screen a plot of the detected micro-object set based on the selected first parameter, wherein the provided parameter list is a limited list of parameters offered within the menu, each of the parameters in the list being selectable to characterize the set of detected micro-objects based on the associated parameter, and wherein the display screen enables selection of a sub-population of the set of detected micro-objects based on at least one selected threshold value for the selected first parameter, and enables display of the detected micro-object set by visually differentiating the sub-population meeting the at least one selected threshold from the remaining micro-objects of the detected set.

Embodiment 273. The computing device of embodiment 272, wherein the provided parameter list provides parameters selected from the group consisting of Circularity, CentroidXPixels, CentroidYPixels, CentroidXMicrons, CentroidYMicrons, CentroidXMicronsPenRelative, CentroidYMicronsPenRelative, NearestNeighborMicrons, DiameterMicrons, VolumeFemtoliters, BackgroundAreaMicrons, MeanBrightness, MinBrightness, MaxBrightness, MedianBrightness, BackgroundMedianBrightness, DeltaMedianBrightness, DeltaMaxBrightness, LogMeanBrightness, LogMaxBrightness, LogMedianBrightness, LogDeltaMaxBrightness, LogDeltaMedianBrightnessCV, BackgroundCV, LogDeltaBrightnessMaxToBackgroundRatio, LogDeltaBrightnessSum, FluidChannelNumber, FieldOfView, CellCount, CellsPerPe, and the change with respect to time of any of the foregoing parameters.

Embodiment 274. The computing device of embodiment 272 or 273, wherein the display screen is a graphic user interface.

Embodiment 275. The computing device of any one of embodiments 272 to 274, wherein the threshold comprises an upper threshold value.

Embodiment 276. The computing device of any one of embodiments 272 to 274, wherein the threshold comprises a lower threshold value.

Embodiment 277. The computing device of any one of embodiments 272 to 274, wherein the threshold comprises a lower threshold value and an upper threshold value.

Embodiment 278. The computing device of any one of embodiments 272 to 277, wherein the display screen enables a slidable selector for threshold value selection.

Embodiment 279. The computing device of any one of embodiments 272 to 278, wherein the display screen enables a point selector for threshold value selection.

Embodiment 280. The computing device of any one of embodiments 272 to 279, wherein the display screen enables a user entered value for threshold value selection Embodiment 281. The computing device of any one of embodiments 272 to 280, wherein the visual differentiation is represented by different colors between the sub-population meeting the threshold from the remaining micro-objects of the detected set.

Embodiment 282. The computing device of any one of embodiments 272 to 281, wherein the menu displayed on the screen is further configured for selecting a second parameter, selected from the provided parameter list, for characterizing the set of detected micro-objects also characterized by the first parameter.

Embodiment 283. The computing device of any one of embodiments 272 to 282, wherein the menu displayed on the screen is further configured for selecting a second parameter, selected from the provided parameter list, for characterizing the sub-population of detected micro-objects meeting the at least one threshold value for the first parameter.

Embodiment 284. The computing device of any one of embodiments 272 to 283, wherein the display screen further enables display of the sub-population of detected micro-objects meeting the at least one threshold value for the first parameter and characterized by the second parameter.

Embodiment 285. The computing device of any one of embodiments 272 to 284, wherein the display screen further enables selection of a subset of the sub-population of detected micro-objects based on at least one selected threshold value for the selected second parameter.

Embodiment 286. The computing device of any one of embodiments 272 to 285, wherein the computing device is further configured to accept screen instructions for repositioning one of the set of detected micro-objects, sub-population of the set of detected micro-objects, a first subset of the sub-population, or a second subset of the first subset.

Embodiment 287. The computing device of any one of embodiments 272 to 286, wherein the computing device is further configured to display on the screen an imaging menu for selecting an imaging parameter, selected from a provided imaging parameter list, for imaging at least a portion of the microfluidic device.

Embodiment 288. The computing device of embodiment 287, wherein the computing device is further configured to display on the screen an imaging menu for selecting a plurality of imaging parameters, selected from a provided imaging parameter list, for imaging at least a portion of the microfluidic device.

Embodiment 289. The computing device of embodiment 287 or 288, wherein the computing device is further configured to display on the screen an algorithm selector for selecting an algorithm, selected from a provided algorithm list, for analyzing images acquired through each selected imaging parameter, and detecting the set of micro-objects.

Embodiment 290. The computing device of any one of embodiments 287 to 289, the computing device being configured to display on the screen at least one of image of each individual detected micro-object, wherein the number of images displayed for each detected micro-object is equal to the number of imaging parameters selected.

Embodiment 291. The computing device of any one of embodiments 287 to 290, the imaging parameter comprising a fluorescent cube type.

Embodiment 292. The computing device of embodiment 291, the fluorescent cube type configured to detect FITC, DAPI, CY5, or Texas Red fluorophores, or the like.

293. The computing device of any one of embodiments 287 to 292, the imaging parameter comprising sub-parameters selected from the group consisting of illumination percentage, exposure time (ms), z-axis offset (microns), and combinations thereof.

Embodiment 294. The computing device of any one of embodiments 287 to 293, wherein the displayed imaging menu is further configured to provide a time lapse selector, wherein the time lapse selector enables selection of time lapse values for imaging at least a portion of the microfluidic device over a selected time period.

Embodiment 295. The computing device of embodiment 294, wherein the time lapse values can be selected from a group consisting of time interval, time delay, total number of cycles, and combinations thereof.

Additional aspects of the disclosed assays will be evident from the detailed description that follows, as well as the claims appended hereto and the drawings.

DETAILED DESCRIPTION

Figure 1A:
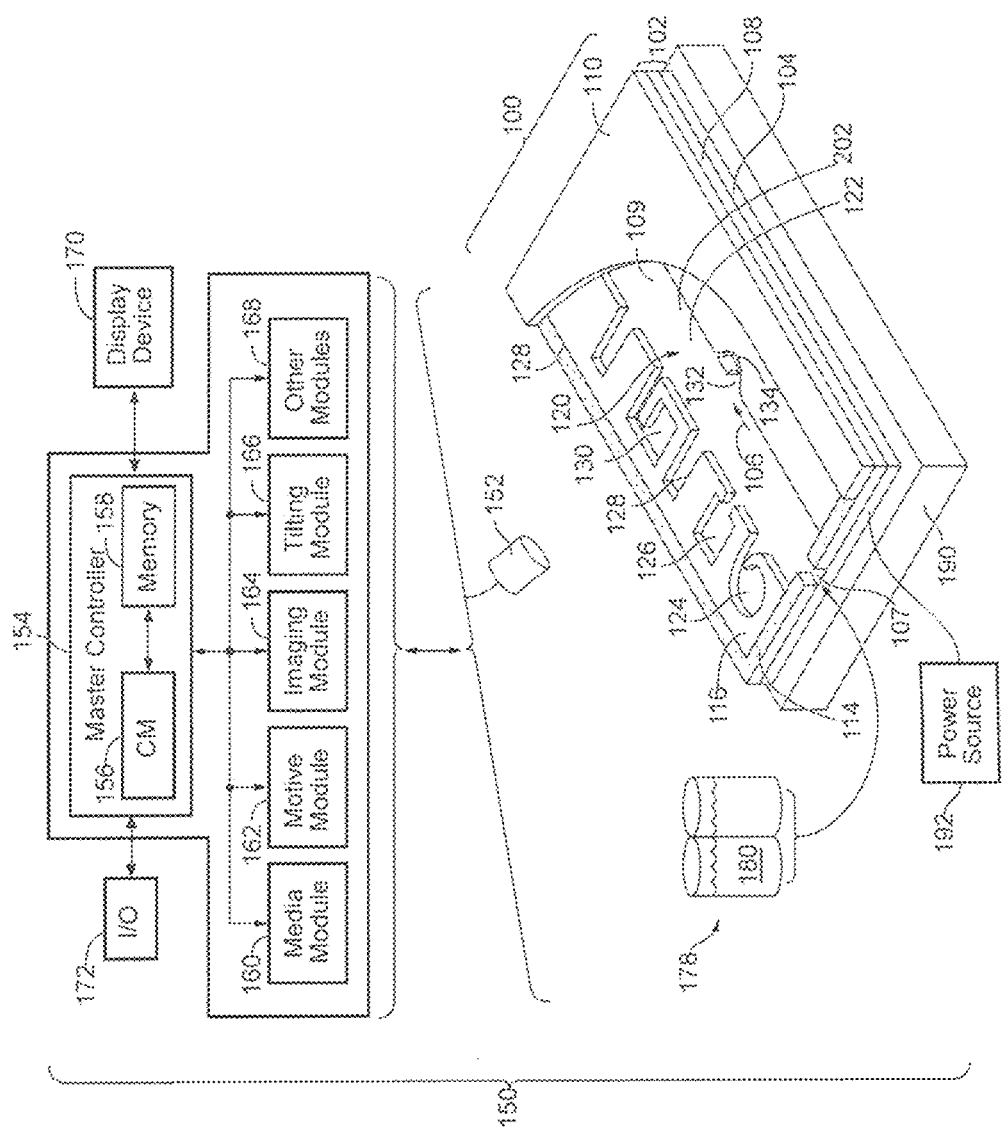
FIG. 1A illustrates an example of a system for use with a microfluidic device and associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein: μm means micrometer, $μm^3$ means cubic micrometer, pL means picoliter, nL means nanoliter, and μL (or uL) means microliter.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 microliters. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 microliters. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 microliters, e.g., less than about 750, 500, 250, 200, 150, 100, 75, 50, 25, 20, 15, 10, 9, 8, 7, 6, 5, 4, 3, 2, 1 nL or less.

A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic device or a nanofluidic device may be referred to herein as a "microfluidic chip" or a "chip"; or "nanofluidic chip" or "chip".

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is about 100,000 microns to about 500,000 microns, including any value therebetween. In some embodiments, the horizontal dimension is about 100 microns to about 1000 microns (e.g., about 150 to about 500 microns) and the vertical dimension is about 25 microns to about 200 microns, (e.g., from about 40 to about 150 microns). It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, the connection region and the isolation region of a microfluidic sequestration pen.

As used herein, the term "constriction" refers generally to a narrowing of a width of a circuit element (or an interface between two circuit elements) in a microfluidic device. The constriction can be located, for example, at the interface between the isolation region and the connection region of a microfluidic sequestration pen of the instant disclosure.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components, and, optionally a surface, that provides the conditions necessary to keep the cells viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein, "capture moiety" is a chemical or biological species, functionality, or motif that provides a recognition site for a micro-object. A selected class of micro-objects may recognize the in situ-generated capture moiety and may bind or have an affinity for the in situ-generated capture moiety. Non-limiting examples include antigens, antibodies, and cell surface binding motifs.

As used herein, "antibody" refers to an immunoglobulin (Ig) and includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, the term "non-illuminated", particularly with reference to images, can refer to illuminated images, such as fluorescent images, that are not illuminated in the same region of the spectrum that light is being imaged. The term non-illuminated can also refer to imaging in a spectrum outside the spectrum of visible light, including, for example, infrared and ultraviolet light.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Detection of secreted biomolecules in a microfluidic environment using automated detection and characterization of micro-objects. A method for detecting a biological molecule of interest secreted by a biological cell in a chamber of a microfluidic device is described herein, where the method includes: disposing the biological cell within the chamber of the microfluidic device; disposing a micro-object in or proximal to the chamber of the microfluidic device, wherein the micro-object comprises a binding agent that binds to the molecule of interest; incubating the biological cell together with the micro-object under conditions sufficient to allow the biological cell to secrete the molecule of interest into the chamber, and for the secreted molecule of interest to diffuse over and bind to the micro-object; and detecting binding of the molecule of interest to the micro-object, wherein detecting binding is performed according to any of the methods described herein for the detection and characterization of micro-objects.

The ability to detect and characterize, in a robust and automated fashion, a specific biomolecule derived from one secreting biological cell permits interrogation of biological pathways that has not been possible previously.

A wide variety of secreted biomolecule assays may be performed using these methods. The biological cell producing the biomolecule of interest (which may be referred to, for simplicity, interchangeably as the molecule of interest) may be an immunological cell, which may include a T cell (e.g., naïve T cell, memory T cell, central memory T cell, effector T cell, or the like); a B cell (e.g., a memory B cell), a plasmablast, or a plasma cell; a NK cell or a macrophage. Alternatively, the biological cell may be a liver cell, a neuron, a pancreatic cell or any cell that secretes a biomolecule of interest. In some embodiments, the biological cell may be a tumor cell.

The molecule of interest may be a protein. In some embodiments, the molecule of interest may be a cytokine or a growth factor. In other embodiments, the molecule of interest may be a hormone (e.g., a proteinaceous hormone). Alternatively, the molecule of interest may be an antibody. In other embodiments, the molecule of interest may be a small molecule, which may be a peptide or an organic molecule. The molecule of interest may be a neurotransmitter. metabolite, secondary messenger, hormone (i.e. a peptidic or organic molecule hormone), lipid, fatty acid, carbohydrate, or the like.

The methods to detect the molecule of interest utilize capture of the molecule of interest to a micro-object configured to capture the molecule of interest. The micro-object may be a bead or other solid particle which may be modified to bear a binding agent capable of binding the molecule of interest. In various embodiments of the method, the binding agent may include a protein. The protein may be an antibody. Alternatively, the protein of the binding agent may be a receptor for the molecule of interest. The binding agent is not so limited to these classes of binding agents, but may be any suitable moiety that can bind a molecule of interest specifically. Other binding agents may include chelation complexes or synthetic binding motifs designed to capture a small molecule or peptide.

The ability to assay for the production of secreted biomolecule from a biological cell within a microfluidic device permits the isolation of the biological cell within a volume of media still permitting observation of binding, despite the low absolute quantities of the molecule of interest. The biological cell is disposed within a chamber of the microfluidic device that limits the volume of surrounding media. In some embodiments, the chamber may have a volume less than about 2 microliters, while in other embodiments the chamber may be a circuit element of the microfluidic device having a volume of about 100 pL to about 2 nL. The micro-object configured to capture the molecule may be disposed within the chamber. In other embodiments, the micro-object configured to capture the molecule of interest may be disposed proximal to the chamber in which the biological cell is disposed.

In various embodiments of the method, the chamber of the microfluidic device may be a sequestration pen that includes an isolation region and a connection region. The sequestration pen may have a volume of about 100 pL to about 1 nL. The isolation region of the sequestration pen may be an unswept region of the microfluidic device, as described herein, and has a single opening to the connection region, and the connection region of the sequestration pen may fluidically connect the isolation region to a flow region of the microfluidic device. The connection region of the sequestration pen may have a proximal opening to a flow region of the microfluidic device and a distal opening to the isolation region. In some embodiments, the connection region has only the single proximal opening and the single distal opening (i.e. has no other openings). In some embodiments, the proximal opening of the connection region has a width $W_{con}$ from about 20 microns to about 100 microns and a length $L_{con}$ of the connection region from the proximal opening to the distal opening is at least 1.0 times the width $W_{con}$ of the proximal opening. In other embodiments, the length $L_{con}$ of the connection region from the proximal opening to the distal opening may be at least 1.5 times or at least 2.0 times the width $W_{con}$ of the connection region. The length $L_{con}$ of the connection region from the proximal opening to the distal opening may be between about 20 microns to about 500 microns. In various embodiments, the isolation regions of the sequestration pens may have a volume of $1 \times 10^6$ cubic microns, $2 \times 10^6$ cubic microns, or $6 \times 10^6$ cubic microns. In some embodiments, the microfluidic device may include a plurality of chambers. At least some of the plurality of chambers of the microfluidic device may each be a sequestration pen having an isolation region and a connection region as described herein. In some embodiments, all of the plurality of chambers may be sequestration pens.

In various embodiments of the method, disposing the micro-object includes disposing the micro-object in the isolation region of the sequestration pen. Disposing the biological cell may include disposing the biological cell in the isolation region of the sequestration pen. The biological cell may be disposed in proximity or adjacent to the micro-object. It may be advantageous to limit the distance that the secreted biomolecule of interest needs to diffuse, to reach the micro-object having the binding agent configured to bind the biomolecule of interest.

After the biological cell and the micro-object are disposed within the microfluidic environment, incubation may be performed for at least 10 minutes (e.g., 15, 20, 25, 30, 35, 40, 45, 50, 55, 60 minutes, or longer), or alternatively for about 1 h, 2 h, 3 h, 4 h, or more. The biological cell may be provided with an environment conducive to production of the molecule of interest. For example, as described in the Example section, a cytokine release assay which measures the production of a cytokine by an antigen-specific T lymphocyte, may include chambers/pens where the biological cell and micro-object are incubated together with other cells that will initiate (or not initiate) production of the biomolecule from the T lymphocyte (e.g, specific antigen-pulsed tumor cells or alternatively, non-target antigen pulsed tumor cells). This is one example only and is not limiting to the types of cells or other molecular species present during incubation. Further, in some embodiments, the biological cell may be incubated with the micro-object under conditions which are designed to inhibit production of the biomolecule of interest.

In various embodiments of the method, detecting binding of the molecule of interest to the micro-object may include introducing a reagent into the microfluidic device, wherein the reagent binds to the molecule of interest while the molecule of interest is bound to the micro-object. The reagent may bind to the molecule of interest at a site (e.g., epitope) such that binding of the reagent to the molecule of interest does not interfere with binding of the molecule of interest to the micro-object. In yet other embodiments, the reagent may bind to the binding agent of the micro-object when the molecule of interest is also bound to the binding agent, but not when the binding agent is not bound to the molecule of interest. The reagent may include a label. The label may permit colorimetric, luminescent or fluorescent detection.

The reagent for detecting binding of the molecule of interest may be flowed into the microfluidic device, and may be perfused through the microfluidic device. In some embodiments, the microfluidic device may further include a microfluidic channel, where the chamber or sequestration pen includes an opening to the microfluidic channel, and flowing the first reagent through the microfluidic device may include flowing the first reagent through the microfluidic channel.

Detection may be repeated at periodic timepoints or may be performed at only one pre-determined timepoint. Detection may include obtaining a brightfield image of the biological cell, micro-object and any other species present in the chamber/sequestration pen of the microfluidic device. Detection may further include obtaining one or more fluorescence images of the biological cell, micro-object and any other species present in the chamber/sequestration pen of the microfluidic device. The automated methods of determination and characterization of micro-objects as described herein may be used to provide the outcome of the assay and correlate the objects observed in the fluorescence images with the objects observed in the brightfield image.

In various embodiments, the method may further include disposing a second (or more) micro-object in or proximal to the chamber of the microfluidic device, wherein the second micro-object comprises a second binding agent that binds to a second molecule of interest produced by the biological cell. The method further may include incubating the biological cell together with the second micro-object (and first micro-object as described in the previous paragraphs) under conditions sufficient to allow the biological cell to secrete the second molecule of interest into the chamber and for sufficient time for the secreted second molecule of interest to diffuse over and bind to the second micro-object. In various embodiments, the second micro-object may be detectably distinguishable from the first micro-object. The second molecule of interest may be different from the first molecule of interest. The second binding agent may bind to the second molecule of interest and substantially not to the first molecule of interest and the first binding agent may not substantially bind to the second molecule of interest. Each of the first micro-object and the second micro-object may specifically and substantially bind to each of the first molecule of interest and the second molecule of interest respectively.

Detection of binding of the second molecule of interest may produce a detectable signal that is distinguishable from the detectable signal of the first molecule of interest. The detectable signal of the binding of the second molecule of interest may be spectrally distinguishable and/or spatially detectable from the detectable signal of the binding of the first molecule of interest. The method also provides for detecting binding of the second molecule of interest to the second micro-object, wherein detecting binding is performed according to any of the methods described herein for the detection and characterization of micro-objects. The detecting of the binding of the second molecule may be distinguishable from the detecting binding of the first molecule of interest.

The second molecule of interest, second binding agent, and second micro-object may be any of the classes described for the first molecule of interest, first binding agent and/or first micro-object described herein. The method may permit further multiplex operations and include three, four or more micro-objects permitting detection of three, four or more molecules of interest, while still permitting distinguishable detection of each. Each of the three, four or more micro-objects may specifically and substantially bind to each of the three, four or more molecules of interest respectively.

Assay of T cell cytotoxicity. Immunotherapy is a promising and rapidly developing field. However, there is need within the field to reproducibly develop or select cellular therapy products with optimized targeting, cytotoxic and persistence phenotypes. Applicant has discovered apparatuses, methods and kits for the determination of the cytotoxic activity of a T lymphocyte (T cell), optionally in combination with other characteristics of the T cell and/or target cell(s) within a microfluidic environment. The ability to assay cytotoxicity or co-assay two or more different activities observable during T cell targeted killing illustrates powerful methods to interrogate the effect(s) of a T cell (or T cells) upon one (or more) target cell(s).

In some embodiments, the methods described herein isolate a single T cell, which may be an antigen specific T cell, with one or more target cells, within a microfluidic environment where the enclosed volume surrounding the T cell and target cell(s) is limited sufficiently to permit 1) the T cell to be maintained in a viable condition and 2) the amount of secreted biomolecule(s) from the T cell are still detectable. In previously available platforms, isolated T cells were not able to be maintained in a viable state, as the volume of media surrounding a T cell excessively diluted the extracellular signaling molecules needed for viability or the T cell was isolated in a droplet where replenishment f nutrients and removal of waste could not occur. These platforms also did not include selective handling technologies, which would permit precise, gentle and selective handling of individual cells and/or capture objects. Additionally, these platforms did not permit imaging of individual cells or groups of cells, so monitoring the effect of a particular secreted biomolecule was not possible. The ability to assay for the production of secreted biomolecule from a biological cell within a microfluidic device, as described herein permits the isolation of the biological cell within a volume of media still permitting observation of binding, despite the low absolute quantities of the molecule of interest. The biological cell is disposed within a chamber of the microfluidic device that limits the volume of surrounding media. In some embodiments, the chamber may have a volume less than about 2 microliters, while in other embodiments the chamber may be a circuit element of the microfluidic device having a volume of about 100 pL to about 2 nL.

Further the methods described here permit co-assay, to multiplex a cytotoxicity assay along with detection of one or more secreted biomolecule(s). Additional flexibility is gained with the further ability to stain for extracellular cell surface markers to gain understanding of the particular state of the T cell.

Figure 29:
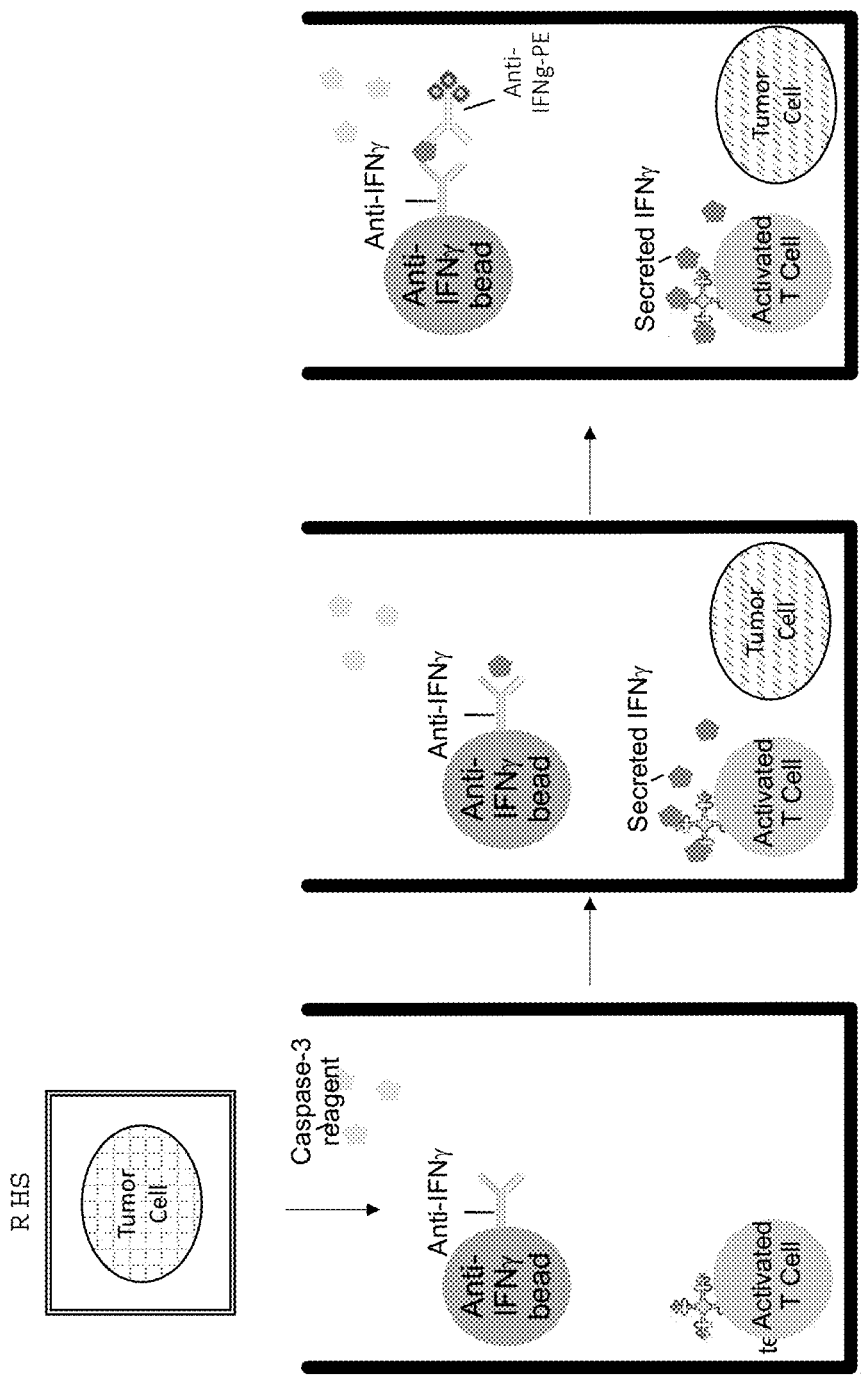
FIG. 29 is a schematic representation of a cytotoxicity/secreted protein detection co-assay according to one embodiment of the disclosure.

Methods. A method for assay of antigen-specific cytotoxicity of a T lymphocyte (T cell) and, optionally, a secreted biomolecule therefrom in a microfluidic device is provided, including: disposing the T cell within the microfluidic device; disposing a first capture object in proximity to the T lymphocyte, where the capture micro-object is configured to capture a first secreted biomolecule released from the T cell; disposing a target cell in proximity to the T cell; detecting the first secreted biomolecule captured to the first capture object; and determining a viability of the target cell after a period of exposure in proximity to the T cell. A schematic diagram of an exemplary co-assay is shown in FIG. 29.

In various embodiments, the target cell expresses an antigen for which the T cell is specific. The target cell may express an antigen associated with melanoma, breast cancer, lung cancer, prostate cancer, or pancreatic cancer. The target cell may be a cancer cell. In some embodiments, the target cancer cell may be a cell from a cell line that expresses a cancer-associated or cancer-specific antigen.

Secreted biomolecule. The secreted biomolecule released from the T cell may be a protein. In some embodiments, the secreted biomolecule may be a cytokine or a growth factor. The cytokine may be Tumor Necrosis Factor alpha (TNF alpha), Interferon gamma (IFN gamma), Interleukin-2 (IL-2), Interleukin-4 (IL-4), Interleukin-5 (IL-5), Interleukin-10 (IL-10), or Interleukin-13 (IL-13). In other embodiments of the method, the secreted protein released from the antigen-specific T cell may be a granzyme or a perforin protein. In other embodiments, the secreted biomolecule may be a hormone (e.g., a proteinaceous hormone). Alternatively, the secreted biomolecule may be an antibody. In other embodiments, the secreted biomolecule may be a small molecule, which may be a peptide or an organic molecule. The secreted biomolecule may be a neurotransmitter. metabolite, secondary messenger, hormone (i.e. a peptidic or organic molecule hormone), lipid, fatty acid, carbohydrate, or the like.

T cell or other immunological cell. The T cell may be a naïve T cell, memory T cell, central memory T cell, effector T cell, or the like. In various embodiments of the method, the T cell may be a mammalian T cell. The T cell may be antigen-specific for a tumor associated antigen. In some embodiments, the tumor associated antigen may be SLC45A2, TCL 1, VCX3A, MART1, or NYESO1. In some embodiments, the T cell may express a chimeric antigen receptor. In other embodiments, the T cell does not express a chimeric antigen receptor. In some embodiments, the method may alternatively use another type of immunological cell instead of a T cell, such as a B cell (e.g., a memory B cell), a plasmablast, or a plasma cell; a NK cell or a macrophage. For simplicity, the discussion following will refer to T cell but the methods are not so limited.

Capture object. The capture object may be a bead or other solid particle which may be modified to bear a binding agent capable of binding the secreted biomolecule. In various embodiments of the method, the binding agent may include a protein. The protein may be an antibody. Alternatively, the protein of the binding agent may be a receptor for the molecule of interest. The binding agent is not so limited to these classes of binding agents, but may be any suitable moiety that can bind a secreted biomolecule specifically. Other binding agents may include chelation complexes or synthetic binding motifs designed to capture a small molecule or peptide.

Microfluidic device useful in the methods. In various embodiments of the method, the microfluidic device useful in the methods may include a flow region for containing a flow of a first fluidic medium and a chamber opening to the flow region. The microfluidic device may further include a microfluidic channel. In some embodiments, the flow region of the microfluidic device may be a microfluidic channel.

In various embodiments of the method, the chamber of the microfluidic device may be a sequestration pen that includes an isolation region and a connection region. The sequestration pen may have a volume of about 100 pL to about 1 nL. The isolation region of the sequestration pen may be an unswept region of the microfluidic device, as described herein, and has a single opening to the connection region, and the connection region of the sequestration pen may fluidically connect the isolation region to a flow region of the microfluidic device. The connection region of the sequestration pen may have a proximal opening to a flow region of the microfluidic device and a distal opening to the isolation region. In some embodiments, the connection region has only the single proximal opening and the single distal opening (i.e. has no other openings). In some embodiments, the proximal opening of the connection region has a width Wcon from about 20 microns to about 100 microns and a length Lcon of the connection region from the proximal opening to the distal opening is at least 1.0 times the width Wcon of the proximal opening. In other embodiments, the length Lcon of the connection region from the proximal opening to the distal opening may be at least 1.5 times or at least 2.0 times the width Wcon of the connection region. The length Lcon of the connection region from the proximal opening to the distal opening may be between about 20 microns to about 500 microns. In various embodiments, the isolation regions of the sequestration pens may have a volume of 1×106 cubic microns, 2×106 cubic microns, or 6×106 cubic microns. In some embodiments, the chamber may have a volume less than about 2 microliters, while in other embodiments the chamber may be a circuit element of the microfluidic device, such as, for example, a sequestration pen, having a volume of about 100 pL to about 2 nL. In some embodiments, the microfluidic device may include a plurality of chambers. At least some of the plurality of chambers of the microfluidic device may each be a sequestration pen having an isolation region and a connection region as described herein. In some embodiments, all of the plurality of chambers may be sequestration pens.

In various embodiments of the method, the microfluidic device may further include an electrode activation substrate. The electrode activation substrate may be configured to generate DEP forces. The microfluidic device useful in the methods may be any microfluidic device as described herein and may have any combination of features.

Introducing cells and capture objects to the microfluidic device. In various embodiments of the method, the T cell, the capture object and the target cell(s) may each be disposed in proximity to each other within the microfluidic device. In some embodiments the T cell, capture object and the target cell(s) may be each disposed within in a chamber of the microfluidic device. In some embodiments, the capture object may be disposed proximal to the chamber. In some embodiments, more than one T cell may be introduced into the chamber of the microfluidic device. In some embodiments, the T cell, the capture object and the target cell may each be disposed in the isolation region of the sequestration pen. In various embodiments, disposing the T cell in the chamber includes disposing a single T cell into the chamber. Disposing the T cell within the microfluidic device may be performed using dielectrophoretic (DEP) forces. In some embodiments, disposing the target cell(s) in the chamber may include disposing a single target cell into the chamber. Disposing the capture object in proximity to the T cell may be performed using dielectrophoretic (DEP) forces. In various embodiments, disposing the target cell(s) in proximity to the T cell may be performed using dielectrophoretic (DEP) forces. After the T cell(s), target cell(s) and the capture object(s) are disposed within the microfluidic environment, incubation may be performed for at least 10 minutes (e.g., 15, 20, 25, 30, 35, 40, 45, 50, 55, 60 minutes, or longer), or alternatively for about 1 h, 2 h, 3 h, 4 h, 5 h, 7 h, 8 h, 10 h, 12 h, or more. The T cell(s) may be provided with an environment conducive to production of the biomolecule. For example, as described in the Example section, a cytokine release assay which measures the production of a cytokine by an antigen-specific T lymphocyte, may include chambers/pens where the T cell and capture object are incubated together with other cells that will initiate (or not initiate) production of the biomolecule from the T lymphocyte (e.g, specific antigen-pulsed tumor cells or alternatively, non-target antigen pulsed tumor cells). This is one example only and is not limiting to the types of cells or other molecular species present during incubation. Further, in some embodiments, the T cell may be incubated with the micro-object under conditions which are designed to inhibit production of the biomolecule. The period of incubation may further include a period of time needed for the secreted biomolecule to diffuse from the T cell to the capture object in order to be captured.

Detection. In various embodiments of the method, the method may further include introducing a secreted biomolecule detection reagent into the microfluidic device. In some embodiments, the secreted protein detection reagent may bind to the secreted biomolecule when it is captured by the first capture object, and may not bind to the secreted biomolecule when it is not captured by the capture object. Detecting the secreted protein may include detecting a colorimetric, luminescent or fluorescent signal. the reagent binds to the molecule of interest while the molecule of interest is bound to the micro-object. The reagent may bind to the molecule of interest at a site (e.g., epitope) such that binding of the reagent to the molecule of interest does not interfere with binding of the molecule of interest to the micro-object. In yet other embodiments, the reagent may bind to the binding agent of the micro-object when the molecule of interest is also bound to the binding agent, but not when the binding agent is not bound to the molecule of interest. The reagent may include a label. The label may permit colorimetric, luminescent or fluorescent detection. Detection may be repeated at periodic timepoints or may be performed at only one pre-determined timepoint. Detection may include obtaining a brightfield image of the biological cell, micro-object and any other species present in the chamber/sequestration pen of the microfluidic device. Detection may further include obtaining one or more fluorescence images of the biological cell, micro-object and any other species present in the chamber/sequestration pen of the microfluidic device. Automated methods of determination and characterization of micro-objects may be used to provide the outcome of the assay and correlate the objects observed in the fluorescence images with the objects observed in the brightfield image, and may include any of the methods described in U.S. Provisional Application No. 62/754,107, filed on Nov. 1, 2018, entitled "Methods for Detection of Secreted Biomolecule of Interest in a Microfluidic Environment Using Automated Detection and Characterization of Micro-Objects", the entire disclosure of which is herein incorporated by reference.

Co-assay and further multiplexed assays. A variety of multiplexed co-assays may be performed using the methods described herein. The absolute number of multiplexed co-assays is limited only by the number of differentiable signals that can be detected within the microfluidic environment. The signals may be differentiable based on, but not limited to, wavelength of fluorescent/colorimetric/luminescent signal, intensity of fluorescent/colorimetric/luminescent signal, combination of fluorescent/colorimetric/luminescent signal, size of micro-object detected, spatial location of signal detected (optionally, in combination with brightfield detection and characterization of micro-objects, including biological cells and capture objects as described herein) and the like.

In some embodiments, the target cell (e.g., tumor cell) may be pre-stained before the start of the co-assay with a stain such a carboxy fluorescein succinimidyl ester (CFSE) to permit better determination, characterization and discrimination between different biological cells and/or other micro-objects within the microfluidic device/chamber/sequestration pen, as described herein.

Cytotoxicity. It is often desirable to combine a cytotoxicity assay in the co-assay methods described herein. A variety of biochemical processes may be tested as measures of cytotoxicity. Any process that assesses cell viability, particularly a process associated with irreversible disruption of function may be employed. Methods can include any of assessing loss of membrane integrity, membrane metabolic activity, arrest of cell in various cell cycle stages, and entrance into apoptotic/necrotic cell death pathways. Identifying cytokine production may help elucidate which T cells may provide the most efficient cytotoxic effect. Lactate dehydrogenase (LDH) assay, trypan blue exclusion and other live/dead staining reagents, 3-(4,5-dimethylthiazolyl-2)-2,5-diphenyl-tetrazolium bromide (MT) and related analogs are some of the reagents which may be used to indicate whether there is loss of membrane integrity. Mitochondrial membrane potential may be used as a cytotoxicity measure, as well as measurement of calcium flux. Another tool for cytotoxicity evaluation is determination of Caspase activity exhibited by the target cell, in particular, activity of Caspase 3 or Caspase 8. Examples 3 and 4 below demonstrate the ability to detect Caspase activity as a marker of cell death, but the methods are not so limited.

Accordingly, determining the viability of the target cell may include contacting the target cell with a detectable marker configured to label a non-viable cell. In some embodiments, the detectable marker configured to label a non-viable cell may be configured to label apoptotic cells. In other embodiments, the detectable marked configured to label a non-viable cell may be configured to label calcium flux or mitochondrial membrane potential. In various embodiments, determining the viability of the target cell after the period of exposure to the T cell may be repeated over a plurality of periods of exposure to the T cell.

In some embodiments, it may be useful to assay for cytotoxicity of a T cell along with evaluation of cytokine secretion from the T cell. The cytokine may be any of Interferon gamma, TNF alpha, IL-2, IL-4, IL-10, IL-13, IL-5, and the like. The co-assay may then combine Caspase 3 or Caspase 8 expression with capture to a capture object of any of Interferon gamma, TNF alpha, IL-2, IL-4, IL-10, IL-13, IL-5, and the like. In other embodiments, the co-assay may combine monitoring of Calcium flux with capture to a capture object of any of Interferon gamma, TNF alpha, IL-2, IL-4, IL-10, IL-13, IL-5, and the like. In yet other embodiments, the co-assay may combine monitoring of mitochondrial membrane potential with capture to a capture object of any of Interferon gamma, TNF alpha, IL-2, IL-4, IL-10, IL-13, IL-5, and the like. I In other embodiments, the secreted biomolecule of the T cell may be a protein having specific activities that may affect cytotoxicity. Examples include, but are not limited to, Granzyme or Perforin. In some embodiments, a co-assay may be performed combining any of the cytotoxicity measurements described above in combination with assessing capture of Granzyme and/or Perforin to a capture object.

Accordingly, in various embodiments of the method, the method may further include introducing a second capture object into the microfluidic device/chamber or sequestration pen of the microfluidic device, where the second capture object is configured to capture a second secreted biomolecule, where the second secreted biomolecule is not the same as a first secreted biomolecule. The second capture object is configured to capture the second secreted biomolecule but not capture the first secreted biomolecule, and the first capture object is configured to capture the first secreted biomolecule but not the second secreted biomolecule. Each of the first capture object and the second capture object specifically captures the first secreted biomolecule and the second secreted biomolecule respectively. The second capture object may be introduced into the microfluidic device and be disposed within or proximal to the chamber or sequestration pen of the microfluidic device The method may further include incubating the biological cell together with the second capture object under conditions sufficient to allow the biological cell to secrete the secreted biomolecule into the chamber and for the secreted biomolecule to diffuse over and bind to the s capture object.

The second secreted biomolecule, second capture object and the binding agent of the second capture object may be any of the classes described for the first molecule of interest, first binding agent and/or first micro-object described herein.

Detecting binding of the second secreted biomolecule may be performed according to any of the methods described herein for the detection and characterization of micro-objects. Detecting the second secreted biomolecule may include detecting a colorimetric, luminescent or fluorescent signal. The colorimetric, luminescent or fluorescent signal of the second secreted biomolecule detection reagent may be distinguishable from the colorimetric, luminescent or fluorescent signal of the first secreted biomolecule detection reagent. The colorimetric, luminescent or fluorescent signal of the second secreted biomolecule detection reagent may be distinguishable from the colorimetric, luminescent or fluorescent signal of the first secreted biomolecule by intensity of signal or by size of the associated capture object. The colorimetric, luminescent or fluorescent signal of the second secreted biomolecule detection reagent may be distinguishable from the colorimetric, luminescent or fluorescent signal of the first secreted biomolecule by location within the microfluidic device, chamber or sequestration pen. The colorimetric, luminescent or fluorescent signal of the second secreted biomolecule detection reagent may be distinguishable from the colorimetric, luminescent or fluorescent signal of the first secreted biomolecule by correlation with the brightfield image and/or autofluorescence properties of the associated capture object. The colorimetric, luminescent or fluorescent signal of the second secreted biomolecule detection reagent may be spectrally distinct from the colorimetric, luminescent or fluorescent signal of the first secreted protein detection reagent.

The method may permit further multiplex operations and include three, four or more capture object permitting detection of three, four or more secreted biomolecules, while still permitting distinguishable detection of each. Each of the three, four or more capture objects specifically and substantially capture each of the three, four or more secreted biomolecules respectively.

Phenotypic assay. In various embodiments of the method, the method may further include labelling the T cell for the presence of one or more cell surface markers associated with proliferation, activation, metabolic activity, memory, exhaustion, and/or lineage. This may be particularly useful for identifying a phenotype of the T cell, but the invention is not so limited. The label for the one or more cell surface markers may be colorimetric, luminescent or fluorescent or may produce a colorimetric, luminescent or fluorescent signal. In some embodiments, the protein may be either on the surface of the T cell or it may be secreted, permitting capture to a capture object as described above for cytokines.

Surface staining may be performed for markers such as: CD4, CD8, CD137, CD107a, and/or CD69, each indicators of classification status of a T cell. In other embodiments, surface staining or bead based capture may be performed for the presence of CD28, CD127, CCR7, and/or CD107. Any of these surface markers may additionally be assayed in combination with IFN gamma cytokine release.

Proliferation (fold-expansion or cell divisions) may be examined for either a T cell or for a target cell by CFSE staining or Live-Dead stain.

Whether the T cell has a memory phenotype may be interrogated by use of surface or intracellular stain for one or more of CD45RA, CD45RO, CCR7. Further, metabolic state may be interrogated using Mitoview or 2-NBDG.

The status of the T cell may be further probed for exhaustion by use of surface stains for markers such as CD57, KLRG1, TIM-3, LAG-3, and/or PD-1.

Additionally, the lineage of the T cell may be probed, such whether it is TH1/TH2, CD4 and the like by looking at the cytokine release and capture of IFNgamma, IL-4, and/or IL13 release or by performing transcriptional profiling of IFNgamma, IL-4, and/or IL-13 expression.

Post Co-Assay. In various embodiments of the method, the method may further include, after determining the viability of the target cell, capturing nucleic acid from the T cell. Capturing the nucleic acid may be performed as described in any suitable method, and may include methods as described in International Application No. PCT/US2017/054628, filed on Sep. 29, 2017, entitled "DNA Barcode Compositions and Methods of In-Situ Identification in a Microfluidic Device" or International Application No. PCT/US2017/057926, filed on Oct. 23, 2017, entitled "Methods for Screening B Cell Lymphocytes" each of which disclosures are herein incorporated in its entirety by reference. The nucleic acid captured from the T cell may be sequenced.

In other embodiments, the method may further include, after determining the viability of the target cell, exporting the T cell from the microfluidic device, for further culturing, processing and/or assaying, such as sequencing.

Kits. Kits for co-assaying antigen-specific cytotoxicity by a T lymphocyte (T cell) and biomolecule release therefrom in a microfluidic device are provided, including: a microfluidic device comprising a flow region for containing a flow of a first fluidic medium and a chamber opening to the flow region; and a cytotoxicity detection reagent configured to detect viability of a target cell. In some embodiments, the chamber of the microfluidic device may include a sequestration pen. The sequestration pen may include an isolation region for containing a second fluidic medium, the isolation region having a single opening, where the isolation region of the sequestration pen is an unswept region of the microfluidic device; and a connection region fluidically connecting the isolation region to the flow region. In some embodiments the microfluidic device may include a microfluidic channel. In various embodiments, the flow region of the microfluidic device may be a microfluidic channel. The microfluidic device of the kit may further include an electrode activation substrate configured to generate dielectrophoretic (DEP) forces. The electrode activation substrate of the microfluidic device may be optically actuated. The microfluidic device may be any microfluidic device described herein and may have any combination of features described herein. The kit may further include a reagent for providing a conditioned surface within the microfluidic device. The reagent may be any suitable reagent for providing a conditioned surface, including a covalently modified surface as described in PCT application No. PCT/US2017/034832, filed on May 26, 2017, entitled "Covalently Modified Surfaces, Kits and Methods of Preparation and Use"

In various embodiments of the kit, the cytotoxicity detection reagent may include a reagent configured to label an apoptotic cell. In other embodiments, the cytotoxicity detection reagent may include a reagent configured to detect calcium flux or mitochondrial membrane potential.

In other embodiment of the kit, the kit may include a first capture object configured to capture a first secreted biomolecule of a T cell. The kit may further include a first biomolecule detection reagent configured to detect the first secreted protein, wherein the reagent is configured to produce a colorimetric, luminescent, or fluorescent signal.

In various embodiments of the kit, the kit may further include a second capture object, and a second secreted biomolecule detection reagent, wherein the second secreted biomolecule is different from the first secreted biomolecule. The second secreted biomolecule detection reagent may produce a colorimetric, luminescent or fluorescent signal. The colorimetric, luminescent or fluorescent signal of the second secreted biomolecule detection reagent may be distinguishable from the colorimetric, luminescent or fluorescent signal of the first secreted biomolecule detection reagent. The colorimetric, luminescent or fluorescent signal of the second secreted biomolecule detection reagent may be distinguishable from the colorimetric, luminescent or fluorescent signal of the first secreted biomolecule by intensity of signal or by size of the associated capture object. The colorimetric, luminescent or fluorescent signal of the second secreted biomolecule reagent may be spectrally distinct from the colorimetric, luminescent or fluorescent signal of the first secreted biomolecule detection reagent.

In yet other embodiments of the kit, the kit may further include one or more reagents to label a cell surface marker of a T lymphocyte, which may be any suitable cell surface marker. The one or more cell surface markers may be any cell surface marker described herein. In some embodiments, more than one cell surface marker is used in the methods.

Microfluidic devices and systems for operating and observing such devices. FIG. 1A illustrates an example of a microfluidic device 100 and a system 150 which can be used for importing, culturing and/or monitoring micro-objects. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device (incorporated within imaging module 164, where the imaging device is not illustrated in FIG. 1A), and a tilting device (part of tilting module 166, where the tilting device is not illustrated in FIG. 1A).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 (part of imaging module 164, discussed below) can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for maintaining, isolating, assaying or culturing biological micro-objects. In some embodiments, the microfluidic circuit 120 comprises a plurality of identical microfluidic sequestration pens.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
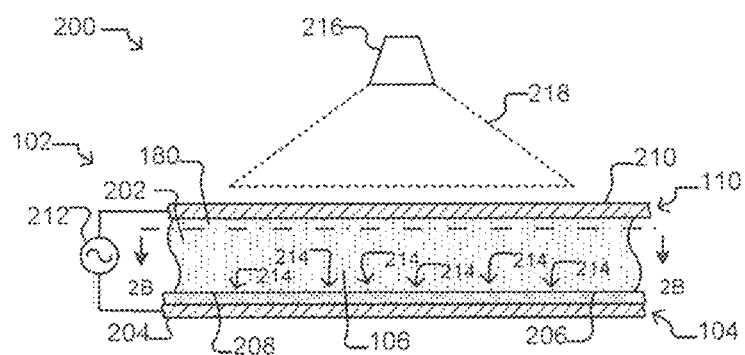
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S.

patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which biological micro-objects can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electrowetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic device motive configurations. As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
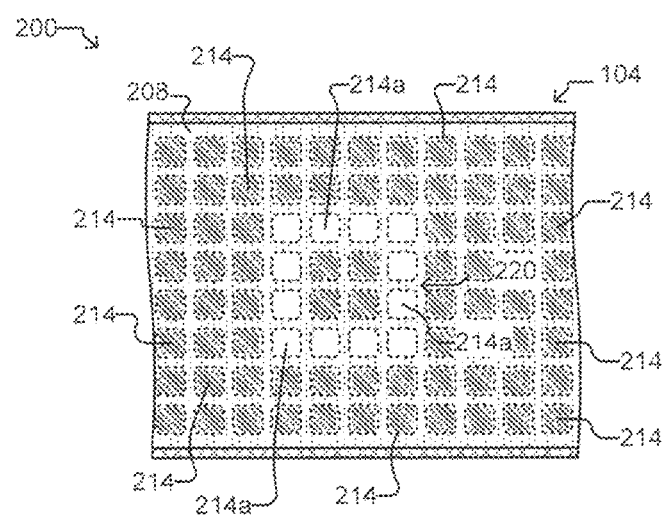

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 □m. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Patent No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.)(see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol.

In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 microns. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration pens. Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

Figure 2A:
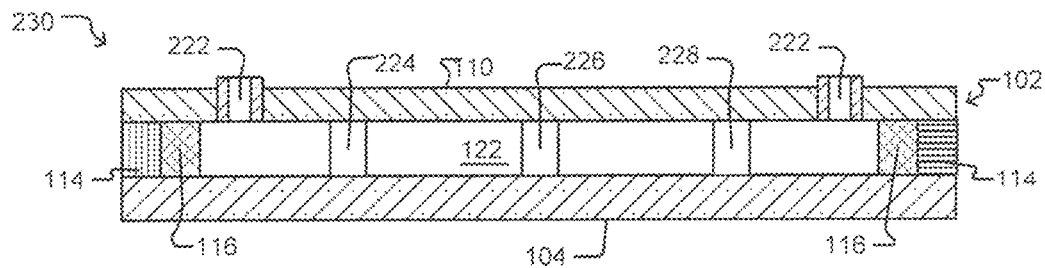
FIGS. 2A and 2B illustrate isolation pens according to some embodiments of the disclosure.
Figure 2B:
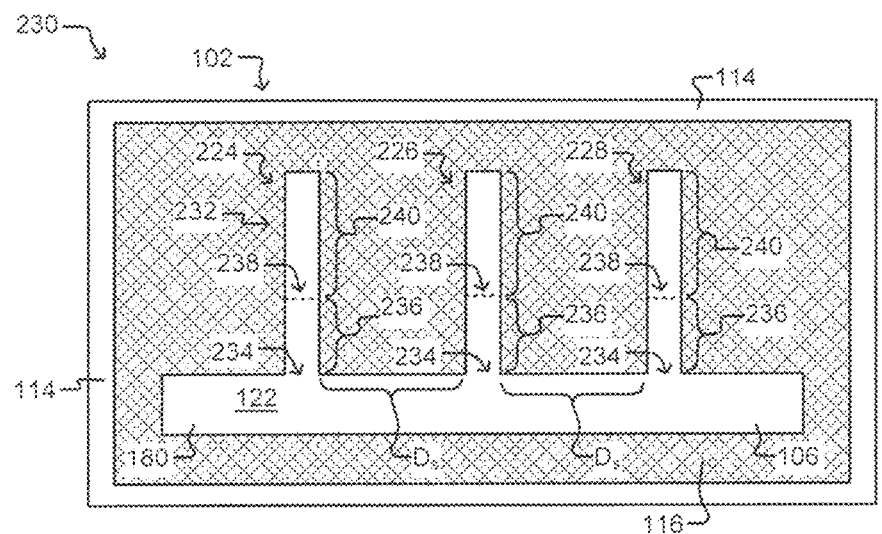
Figure 2C:
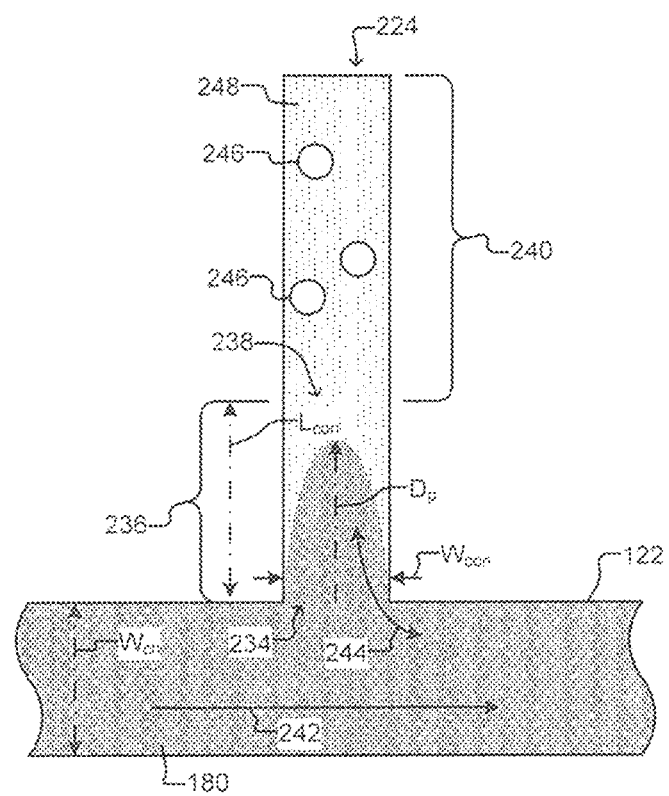
FIG. 2C illustrates a detailed sequestration pen according to some embodiments of the disclosure.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%, 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 200, 230, 250, 280, 290, 300 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be any of the values identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be any of the values identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width Ween of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
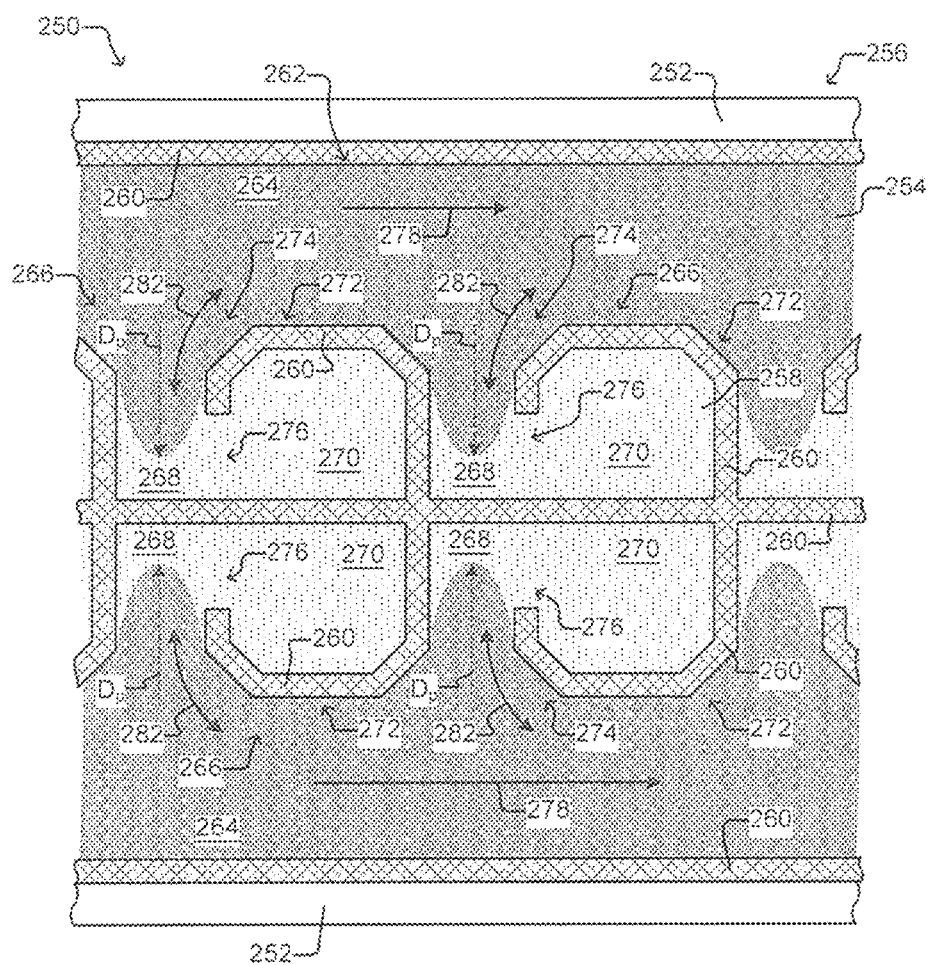
FIGS. 2D-F illustrate sequestration pens according to some other embodiments of the disclosure.
Figure 2E:
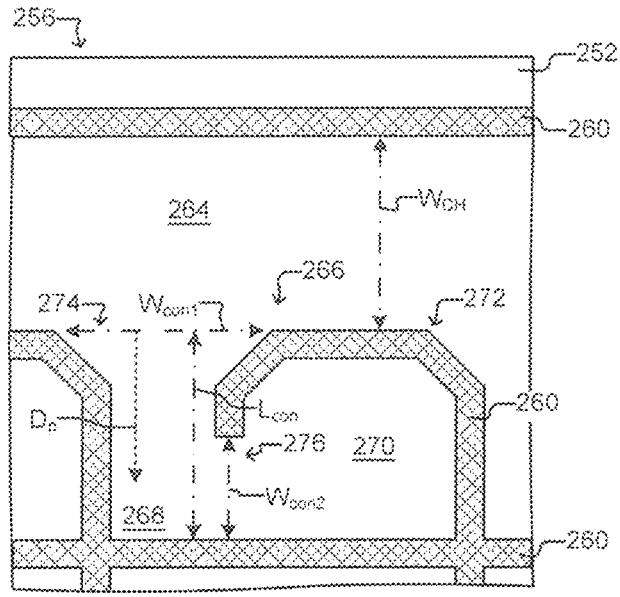
Figure 2F:
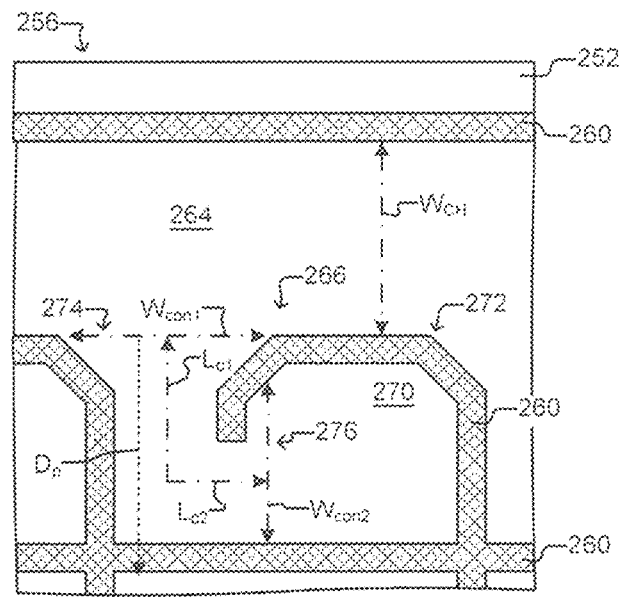

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290, 300. Likewise, the microfluidic device 250 is another variant of the microfluidic device 100, and may also have the same or a different DEP configuration as the above-described microfluidic device 100, 200, 230, 280, 290, 300 as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles of: about 30° to about 90°, about 45° to about 90°, about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the microfluidic channel (e.g., 122) at a proximal opening (e.g. 234) can be about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, or 100-120 microns. In some other embodiments, the width $W_{ch}$ of the microfluidic channel (e.g., 122) at a proximal opening (e.g. 234) can be about 200-800 microns, 200-700 microns, or 200-600 microns. The foregoing are examples only, and the width $W_{ch}$ of the microfluidic channel 122 can be any width within any of the endpoints listed above. Moreover, the $W_{ch}$ of the microfluidic channel 122 can be selected to be in any of these widths in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1 \times 10^4$–$3 \times 10^6$ square microns, $2 \times 10^4$–$2 \times 10^6$ square microns, $4 \times 10^4$–$1 \times 10^6$ square microns, $2 \times 10^4$–$5 \times 10^5$ square microns, $2 \times 10^4$–$1 \times 10^5$ square microns or about $2 \times 10^5$–$2 \times 10^6$ square microns.

In various embodiments of sequestration pens, the height $H_{ch}$ of the microfluidic channel (e.g., 122) at a proximal opening (e.g., 234) can be a height within any of the following heights: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be a height within any of the endpoints listed above. The height $H_{ch}$ of the microfluidic channel 122 can be selected to be in any of these heights in regions of the microfluidic channel other than at a proximal opening of a sequestration pen.

In various embodiments of sequestration pens a cross-sectional area of the microfluidic channel (e.g., 122) at a proximal opening (e.g., 234) can be about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be any area within any of the endpoints listed above.

In various embodiments of sequestration pens, the length Lon of the connection region (e.g., 236) can be about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length Lcm of a connection region (e.g., 236) can be in any length within any of the endpoints listed above.

In various embodiments of sequestration pens the width $W_{con}$ of a connection region (e.g., 236) at a proximal opening (e.g., 234) can be about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, or 80-100 microns. The foregoing are examples only, and the width $W_{con}$ of a connection region (e.g., 236) at a proximal opening (e.g., 234) can be different than the foregoing examples (e.g., any value within any of the endpoints listed above).

In various embodiments of sequestration pens, the width $W_{con}$ of a connection region (e.g., 236) at a proximal opening (e.g., 234) can be at least as large as the largest dimension of a micro-object (e.g., biological cell which may be a T cell, B cell, or an ovum or embryo) that the sequestration pen is intended for. The foregoing are examples only, and the width $W_{con}$ of a connection region (e.g., 236) at a proximal opening (e.g., 234) can be different than the foregoing examples (e.g., a width within any of the endpoints listed above).

In various embodiments of sequestration pens, the width $W_{pr}$ of a proximal opening of a connection region may be at least as large as the largest dimension of a micro-object (e.g., a biological micro-object such as a cell) that the sequestration pen is intended for. For example, the width $W_{pr}$ may be about 50 microns, about 60 microns, about 100 microns, about 200 microns, about 300 microns or may be about 50-300 microns, about 50-200 microns, about 50-100 microns, about 75-150 microns, about 75-100 microns, or about 200-300 microns.

In various embodiments of sequestration pens, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 can be different than the foregoing examples.

In various embodiments of microfluidic devices 100, 200, 23, 250, 280, 290, 300, $V_{max}$ can be set around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, or 15 microliters/sec.

In various embodiments of microfluidic devices having sequestration pens, the volume of an isolation region (e.g., 240) of a sequestration pen can be, for example, at least $5 \times 10^5$, $8 \times 10^5$, $1 \times 10^6$, $2 \times 10^6$, $4 \times 10^6$, $6 \times 10^6$, $8 \times 10^6$, $1 \times 10^7$, $5 \times 10^7$, $1 \times 10^8$, $5 \times 10^8$, or $8 \times 10^8$ cubic microns, or more. In various embodiments of microfluidic devices having sequestration pens, the volume of a sequestration pen may be about $5 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, about 1000 to about 3500 sequestration pens, about 3000 to about 7000 sequestration pens, about 5000 to about 10,000 sequestration pens, about 9,000 to about 15,000 sequestration pens, or about 12,000 to about 20,000 sequestration pens. The sequestration pens need not all be the same size and may include a variety of configurations (e.g., different widths, different features within the sequestration pen).

Figure 2G:
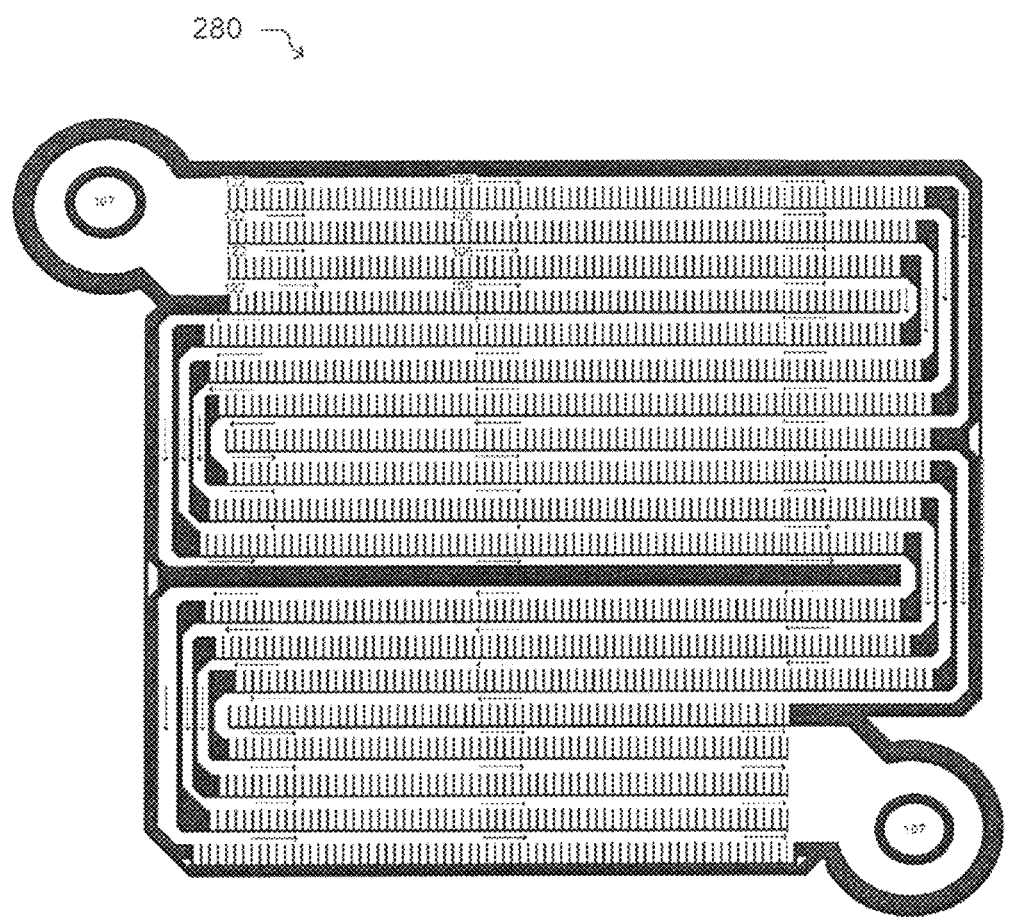
FIG. 2G illustrates a microfluidic device according to an embodiment of the disclosure.

FIG. 2G illustrates a microfluidic device 280 according to one embodiment. The microfluidic device 280 illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
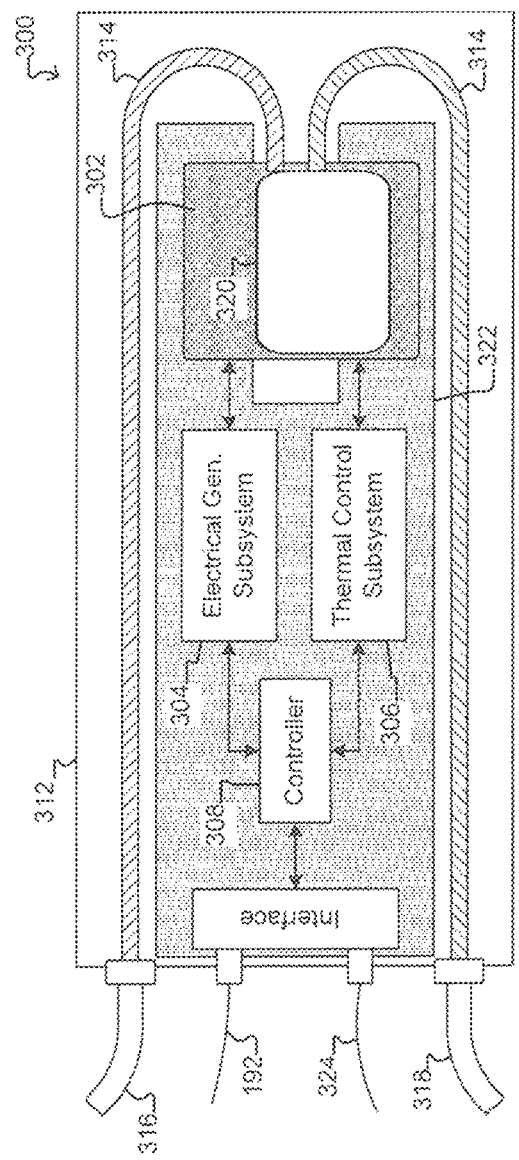
FIG. 3A illustrates a specific example of a system for use with a microfluidic device and associated control equipment according to some embodiments of the disclosure.
Figure 3B:
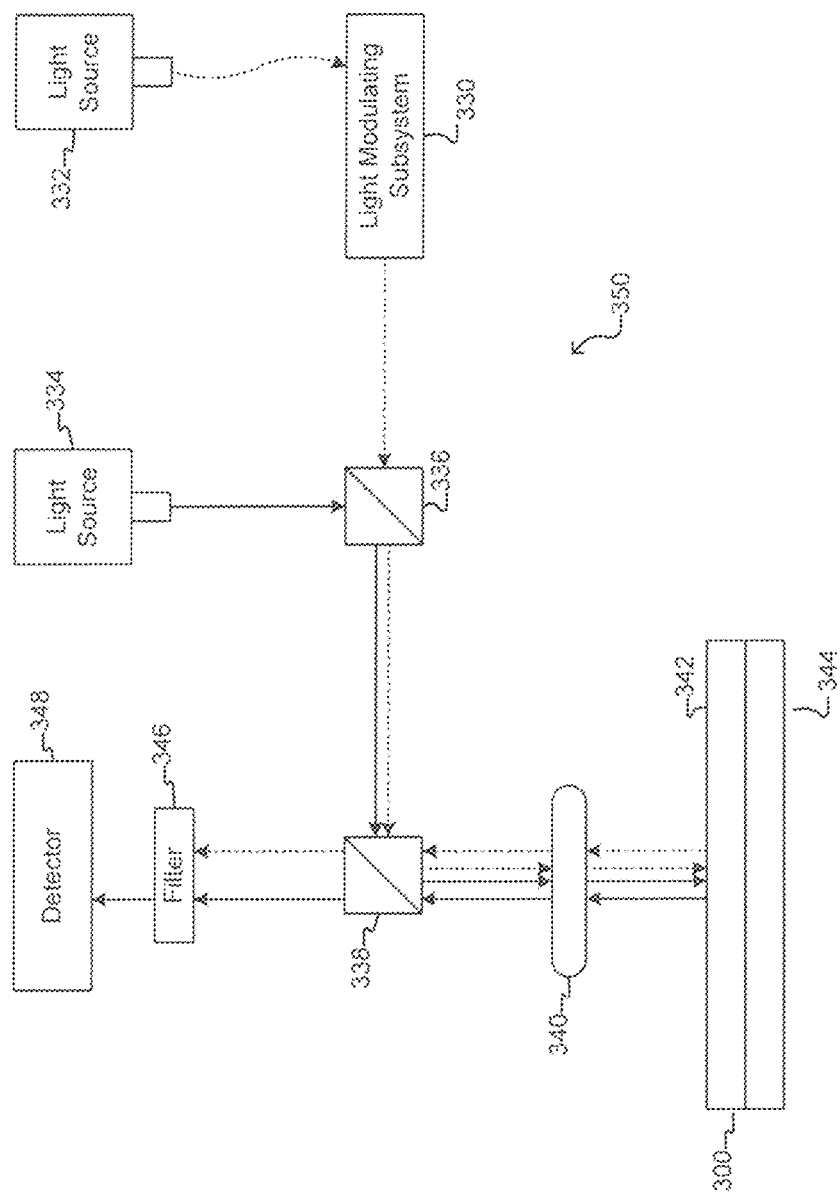
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290, 300) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI)(not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. In certain embodiments, imaging module 164 and/or motive module 162 of system 150 can control the light modulating subsystem 330.

In certain embodiments, the imaging device 194 further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for bright field and/or fluorescent excitation, as well as laser illumination the physical arrangement of the light source(s) may vary from that shown in FIG. 3B, and the laser illumination may be introduced at any suitable physical location within the optical system. The schematic locations of light source 334 and light source 332/light modulating subsystem 330 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through an objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Coating solutions and coating agents. Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating agent/Solution. Any convenient coating agent/coating solution can be used, including but not limited to: serum or serum factors, bovine serum albumin (BSA), polymers, detergents, enzymes, and any combination thereof.

Polymer-based coating materials. The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic non-ionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA)

and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a concentration from about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a concentration of about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently linked coating materials. In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocyclic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprises carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned surface properties. Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface has a thickness of about 1 nm to about 10 nm; about 1 nm to about 7 nm; about 1 nm to about 5 nm; or any individual value therebetween. In other embodiments, the conditioned surface formed by the covalently linked moieties may have a thickness of about 10 nm to about 50 nm. In various embodiments, the conditioned surface prepared as described herein has a thickness of less than 10 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). These values are in contrast to that of a surface prepared by spin coating, for example, which may typically have a thickness of about 30 nm. In some embodiments, the conditioned surface does not require a perfectly formed monolayer to be suitably functional for operation within a DEP-configured microfluidic device.

In various embodiments, the coating material providing a conditioned surface of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-part conditioned surface. The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of preparing a covalently linked coating material. In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

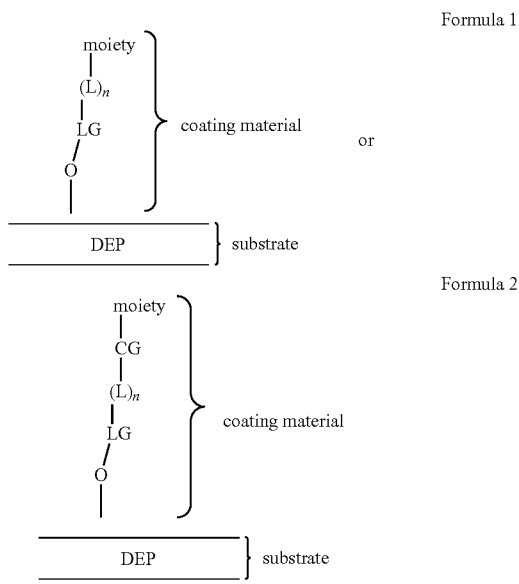

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and/or phosphorus atoms, subject to chemical bonding limitations as is known in the art. It may be interrupted with any combination of one or more moieties, which may be chosen from ether, amino, carbonyl, amido, and/or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety Rx and a reactive pairing moiety $R_{px}$ (i.e., a moiety configured to react with the reactive moiety Rx). For example, one typical coupling group CG may include a carboximidoyl group, which is the result of the reaction of an amino group with a derivative of a carboxylic acid, such as an activated ester, an acid chloride or the like. Other CG may include a triazolylene group, a carboximidoyl, thioimidoyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
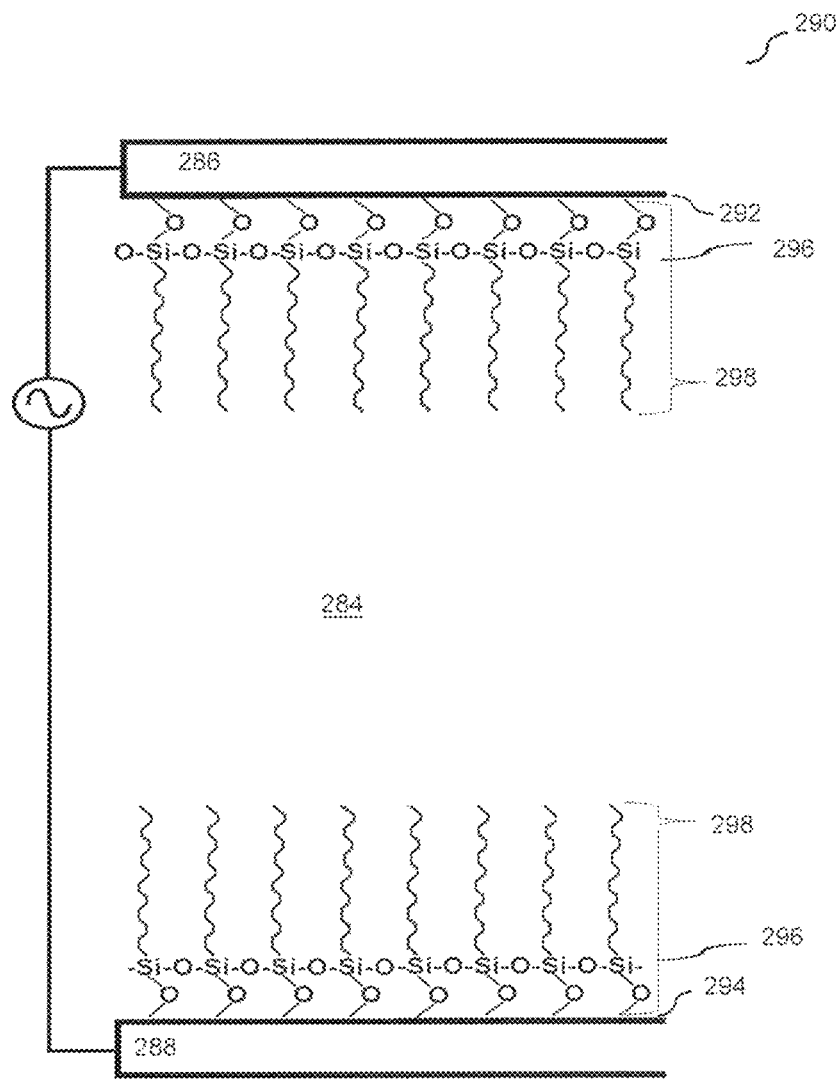
FIG. 2H illustrates a coated surface of the microfluidic device according to an embodiment of the disclosure.

FIG. 2H depicts a cross-sectional view of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated, a fluoroalkyl terminated moiety, a PEG-terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate).

Further details of appropriate coating treatments and modifications may be found at U.S. application Ser. No. 15/135,707, filed on Apr. 22, 2016, and is incorporated by reference in its entirety.

Additional system components for maintenance of viability of cells within the sequestration pens of the microfluidic device. In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

Computer System

Figure 5:
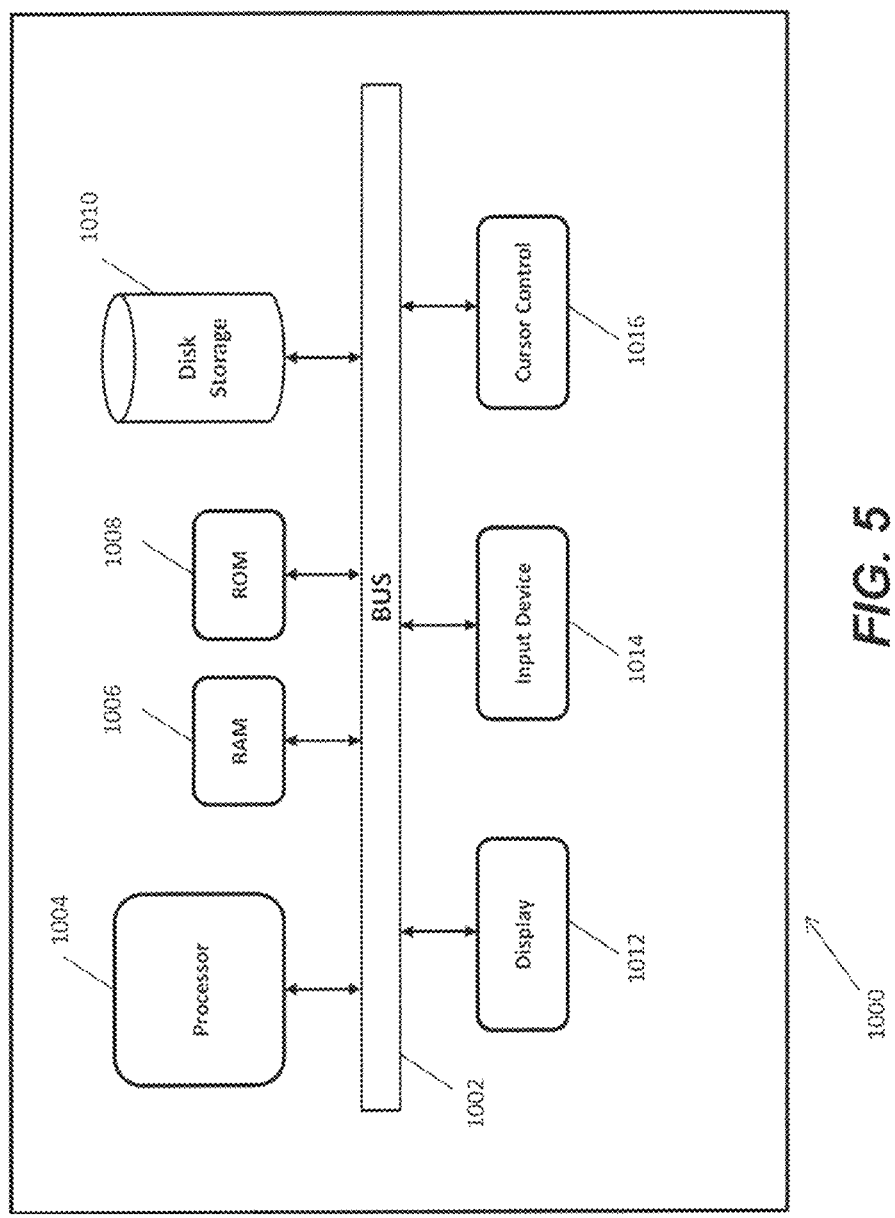
FIG. 5 illustrates is a block diagram of a computer system, in accordance with various embodiments.

FIG. 5 is a block diagram that illustrates a computer system 1000, upon which embodiments, or portions of the embodiments, of the present teachings may be implemented. In various embodiments of the present teachings, computer system 1000 can include a bus 1002 or other communication mechanism for communicating information, and a processor 1004 coupled with bus 1002 for processing information. In various embodiments, computer system 1000 can also include a memory 1006, which can be a random access memory (RAM) or other dynamic storage device, coupled to bus 1002 for determining instructions to be executed by processor 1004. Memory 1006 also can be used for storing temporary variables or other intermediate information during execution of instructions to be executed by processor 1004. In various embodiments, computer system 1000 can further include a read only memory (ROM) 1008 or other static storage device coupled to bus 1002 for storing static information and instructions for processor 1004. A storage device 1010, such as a magnetic disk or optical disk, can be provided and coupled to bus 1002 for storing information and instructions.

In various embodiments, computer system 1000 can be coupled via bus 1002 to a display 1012, such as a cathode ray tube (CRT) or liquid crystal display (LCD), for displaying information to a computer user. An input device 1014, including alphanumeric and other keys, can be coupled to bus 1002 for communicating information and command selections to processor 1004. Another type of user input device is a cursor control 1016, such as a mouse, a trackball or cursor direction keys for communicating direction information and command selections to processor 1004 and for controlling cursor movement on display 1012. This input device 1014 typically has two degrees of freedom in two axes, a first axis (i.e., x) and a second axis (i.e., y), that allows the device to specify positions in a plane. However, it should be understood that input devices 1014 allowing for 3-dimensional (x, y and z) cursor movement are also contemplated herein.

Consistent with certain implementations of the present teachings, results can be provided by computer system 1000 in response to processor 1004 executing one or more sequences of one or more instructions contained in memory 1006. Such instructions can be read into memory 1006 from another computer-readable medium or computer-readable storage medium, such as storage device 1010. Execution of the sequences of instructions contained in memory 1006 can cause processor 1004 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 1004 for execution. Such a medium can take many forms, including but not limited to, non-volatile media, volatile media, and transmission media. Examples of non-volatile media can include, but are not limited to, optical, solid state, magnetic disks, such as storage device 1010. Examples of volatile media can include, but are not limited to, dynamic memory, such as memory 1006. Examples of transmission media can include, but are not limited to, coaxial cables, copper wire, and fiber optics, including the wires that comprise bus 1002.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 1004 of computer system 1000 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein including flow charts, diagrams and accompanying disclosure can be implemented using computer system 1000 as a standalone device or on a distributed network of shared computer processing resources such as a cloud computing network.

It should further be appreciated that in certain embodiments, machine readable storage devices are provided for storing non-transitory machine-readable instructions for executing or carrying out the methods described herein. The machine-readable instructions can control all aspects of the image processing, Convolutional neural network (CNN) flow (described in detail below), logic and memory modules, and micro-object detection and count as described in detail below. Furthermore, the machine-readable instructions can be initially loaded into the memory module or accessed via the cloud or via the API.

Automated detection of a micro-object of interest. In one aspect, methods are provided for the automated detection of a micro-object of interest in an illuminated image, such as a bright field image, and particularly a digital image (or an image that has been digitized). The micro-object of interest can be disposed within a microfluidic device. The micro-object of interest can be a cell, such as a mammalian cell (e.g., a blood cell, a hybridoma, a cancer cell, a transformed cell, a gamete, an embryo, or the like). Alternatively, the micro-object of interest can be a bead, such as might be used in an assay (e.g., a microbead, a magnetic bead, or the like). The methods can involve the use of a machine learning algorithm to process image data (i.e., data relating to pixels in the image). The machine learning algorithm can include a neural network, such as a convolutional neural network.

Image classification requires accepting an input image and outputting a class or a probability of classes that best describes the image. This can be done using a computer system equipped with a processing engine, which utilizes algorithms, to process the input image and output a result. Image detection can also utilize a similar processing engine, whereby the system accepts an input image and identifies objects of interest within that image with a high level of accuracy using the algorithms pre-programmed into the processing engine.

Regarding the input image, the system will generally orient the input image as an array of pixel values. These pixel values, depending on the image resolution and size, will be an array of numbers corresponding to (length)×(width)×(# of channels). The number of channels can also be referred to as the depth. For example, the array could be L×W×Red Green Blue color model (RBG values). The RGB would be considered three channels, each channel representing one of the three colors in the RGB color model. For example, the system can generally characterize a 20×20 image with a representative array of 20×20×3 (for RGB), with each point in the array assigned a value (e.g., 0 to 255) representing pixel intensity. Given this array of values, the processing engine can process these values, using its algorithms, to output numbers that describe the probability of the image being a certain class (e.g., 0.80 for cell, 0.15 for cell wall, and 0.05 for no cell).

A convolutional neural network (CNN) generally accomplishes an advanced form of image processing and classification/detection by first looking for low level features such as, for example, edges and curves, and then advancing to more abstract (e.g., unique to the type of images being classified) concepts through a series of convolutional layers. A CNN can do this by passing an image through a series of convolutional, nonlinear, pooling (or downsampling, as will be discussed in more detail below), and fully connected layers, and get an output. Again, the output can be a single class or a probability of classes that best describes the image or detects objects on the image.

Regarding layers in a CNN, the first layer is generally a convolutional layer (Conv). This first layer will process the image's representative array using a series of parameters. Rather than processing the image as a whole, a CNN will analyze a collection of image sub-sets using a filter (or neuron or kernel). The sub-sets will include a focal point in the array as well as surrounding points. For example, a filter can examine a series of 5×5 areas (or regions) in a 32×32 image. These regions can be referred to as receptive fields. Since the filter generally will possess the same depth as the input, an image with dimensions of 32×32×3 would have a filter of the same depth (e.g., 5×5×3). The actual step of convolving, using the exemplary dimensions above, would involve sliding the filter along the input image, multiplying filter values with the original pixel values of the image to compute element wise multiplications, and summing these values to arrive at a single number for that examined region of the image.

After completion of this convolving step, using a 5×5×3 filter, an activation map (or filter map) having dimensions of 28×28×1 will result. For each additional layer used, spatial dimensions are better preserved such that using two filters will result in an activation map of 28×28×2. Each filter will generally have a unique feature it represents (e.g., colors, edges, curves, etc) that, together, represent the feature identifiers required for the final image output. These filters, when used in combination, allow the CNN to process an image input to detect those features present at each pixel. Therefore, if a filter serves as a curve detector, the convolving of the filter along the image input will produce an array of numbers in the activation map that correspond to high likelihood of a curve (high summed element wise multiplications), low likelihood of a curve (low summed element wise multiplications) or a zero value where the input volume at certain points provided nothing that would activate the curve detector filter. As such, the greater number of filters (also referred to as channels) in the Conv, the more depth (or data) that is provided on the activation map, and therefore more information about the input that will lead to a more accurate output.

Balanced with accuracy of the CNN is the processing time and power needed to produce a result. In other words, the more filters (or channels) used, the more time and processing power needed to execute the Conv. Therefore, the choice and number of filters (or channels) to meet the needs of the CNN method should be specifically chosen to produce as accurate an output as possible while considering the time and power available.

To further enable a CNN to detect more complex features, additional Convs can be added to analyze what outputs from the previous Conv (i.e., activation maps). For example, if a first Conv looks for a basic feature such as a curve or an edge, a second Conv can look for a more complex feature such as shapes, which can be a combination of individual features detected in an earlier Conv layer. By providing a series of Convs, the CNN can detect increasingly higher level features to eventually arrive at a probability of detecting the specific desired object. Moreover, as the Convs stack on top of each other, analyzing the previous activation map output, each Conv in the stack is naturally going to analyze a larger and larger receptive field by virtue of the scaling down that occurs at each Conv level, thereby allowing the CNN to respond to a growing region of pixel space in detecting the object of interest.

A CNN architecture generally consists of a group of processing blocks, including at least one processing block for convoluting an input volume (image) and at least one for deconvolution (or transpose convolution). Additionally, the processing blocks can include at least one pooling block and unpooling block. Pooling blocks can be used to scale down an image in resolution to produce an output available for Conv. This can provide computational efficiency (efficient time and power), which can in turn improve actual performance of the CNN. Though these pooling, or subsampling, blocks keep filters small and computational requirements reasonable, these blocks can coarsen the output (can result in lost spatial information within a receptive field), reducing it from the size of the input by a specific factor.

Unpooling blocks can be used to reconstruct these coarse outputs to produce an output volume with the same dimensions as the input volume. An unpooling block can be considered a reverse operation of a convoluting block to return an activation output to the original input volume dimension.

However, the unpooling process generally just simply enlarges the coarse outputs into a sparse activation map. To avoid this result, the deconvolution block densifies this sparse activation map to produce both an enlarged and dense activation map that eventually, after any further necessary processing, produces a final output volume with size and density much closer to the input volume. As a reverse operation of the convolution block, rather than reducing multiple array points in the receptive field to a single number, the deconvolution block associates a single activation output point with multiple outputs to enlarge and densify the resulting activation output.

It should be noted that while pooling blocks can be used to scale down an image and unpooling blocks can be used to enlarge these scaled down activation maps, convolution and deconvolution blocks can be structured to both convolve/deconvolve and scale down/enlarge without the need for separate pooling and unpooling blocks.

The pooling and unpooling process can have drawbacks depending on the objects of interest being detected in an image input. Since pooling generally scales down an image by looking at sub-image windows without overlap of windows, there is a clear loss of spatial info as scale down occurs.

A processing block can include other layers that are packaged with a convolutional or deconvolutional layer. These can include, for example, a rectified linear unit layer (ReLU) or exponential linear unit layer (ELU), which are activation functions that examine the output from a Conv in its processing block. The ReLU or ELU layer acts as a gating function to advance only those values corresponding to positive detection of the feature of interest unique to the Conv.

Given a basic architecture, the CNN is then prepared for a training process to hone its accuracy in image classification/detection (of objects of interest). This involves a process called backpropagation (backprop), which uses training data sets, or sample images used to train the CNN so that it updates its parameters in reaching an optimal, or threshold, accuracy. Backpropagation involves a series of repeated steps (training iterations) that, depending on the parameters of the backprop, will either slowly or quickly train the CNN. Backprop steps generally include a forward pass, loss function, backward pass, and parameter (weight) update according to a given learning rate. The forward pass involves passing a training image through the CNN. The loss function is a measure of error in the output. The backward pass determines the contributing factors to the loss function. The weight update involves updating the parameters of the filters to move the CNN towards optimal. The learning rate determines the extent of weight update per iteration to arrive at optimal. If the learning rate is too low, the training may take too long and involve too much processing capacity. If the learning rate is too fast, each weight update may be too large to allow for precise achievement of a given optimum or threshold.

The backprop process can cause complications in training, thus leading to the need for lower learning rates and more specific and carefully determined initial parameters upon start of training. One such complication is that, as weight updates occur at the conclusion of each iteration, the changes to the parameters of the Convs amplify the deeper the network goes. For example, if a CNN has a plurality of Convs that, as discussed above, allows for higher level feature analysis, the parameter update to the first Conv is multiplied at each subsequent Conv. The net effect is that the smallest changes to parameters can have large impact depending on the depth of a given CNN. This phenomenon is referred to as internal covariate shift.

The embodiments disclosed herein have several advantages versus known CNNs. These advantages include, for example, providing a CNN that avoids the lost spatial information inherent in pooling layers, reduces/minimizes the internal covariate shift inherent in the backprop process, and reduces the processing time and speed generally needed in deep neural networks to achieve more complex feature detection.

As described above, CNNs consist of multiple layers of receptive fields. These are "neuron" (or kernel) collections which process portions of the input image. The outputs of these collections are then tiled so that their input regions overlap, to obtain a better representation of the original image; this is repeated for every such layer. Tiling allows CNNs to tolerate translation of the input image. CNNs have been described, for example, in Long et al., "Fully Convolutional Networks for Semantic Segmentation," CVPR 2015, and Noh et al., "Learning Deconvolution Network for Semantic Segmentation," ICCV 2015, the contents of each of which are incorporated herein by reference.

The CNN can comprise combinations of convolutional and fully connected layers, with pointwise nonlinearity applied at the end of or after each layer. Convolution operation on small regions of input is introduced to reduce the number of free parameters and improve generalization. One major advantage of convolutional networks is the use of shared weight in convolutional layers, which means that the same filter (weights bank) is used for each pixel in the layer: this both reduces memory footprint and improves performance.

In one embodiment, the CNN is formed by a stack of distinct layers that transform the input volume into an output volume (e.g. holding the class scores) through a differentiable function.

In this embodiment, the convolutional layers are defined as empty, monoclonal, and polyclonal. The layer's parameters can include a set of learnable filters, which have a small receptive field, but extend through the full depth of the input volume. During the forward pass, each filter is convolved across the width and height of the input volume, computing the dot product between the entries of the filter and the input and producing a 2-dimensional activation map of that filter. As a result, the network learns filters that activate when they see some specific type of feature at some spatial position in the input.

Stacking the activation maps for all filters along the depth dimension forms the full output volume of the convolution layer. Every entry in the output volume can thus also be interpreted as an output of a neuron that looks at a small region in the input and shares parameters with neurons in the same activation map.

In one embodiment, the spatial arrangement is based on hyperparameters that control the size of the output volume of the convolutional layer: such as, the depth, stride, and zero-padding.

In one embodiment, the depth of the output volume controls the number of neurons in the layer that connect to the same region of the input volume. All of these neurons will learn to activate for different features in the input. For example, if the first convolutional layer takes the raw image as input, then different neurons along the depth dimension may activate in the presence of various oriented edges, or blobs of color.

In one embodiment, stride controls how depth columns around the spatial dimensions (width and height) are allocated. When the stride is 1, a new depth column of neurons is allocated to spatial positions only 1 spatial unit apart. This leads to heavily overlapping receptive fields between the columns, and also to large output volumes. Conversely, if higher strides are used then the receptive fields will overlap less and the resulting output volume will have smaller dimensions spatially.

Sometimes it is convenient to pad the input with zeros on the border of the input volume. The size of this zero-padding is a third hyperparameter. Zero padding provides control of the output volume spatial size. In particular, sometimes it is desirable to exactly preserve the spatial size of the input volume.

In this embodiment, parameter sharing scheme is used in convolutional layers to control the number of free parameters. It relies on one reasonable assumption: That if one patch feature is useful to compute at some spatial position, then it should also be useful to compute at a different position. In other words, denoting a single 2-dimensional slice of depth as a depth slice, we constrain the neurons in each depth slice to use the same weights and bias.

Since all neurons in a single depth slice are sharing the same parametrization, then the forward pass in each depth slice of the CONV layer can be computed as a convolution of the neuron's weights with the input volume (hence the name: convolutional layer).

Therefore, it is common to refer to the sets of weights as a filter which is convolved with the input. The result of this convolution is an activation map, and the set of activation maps for each different filter are stacked together along the depth dimension to produce the output volume. Parameter Sharing contributes to the translation invariance of the CNN architecture.

Figure 7:
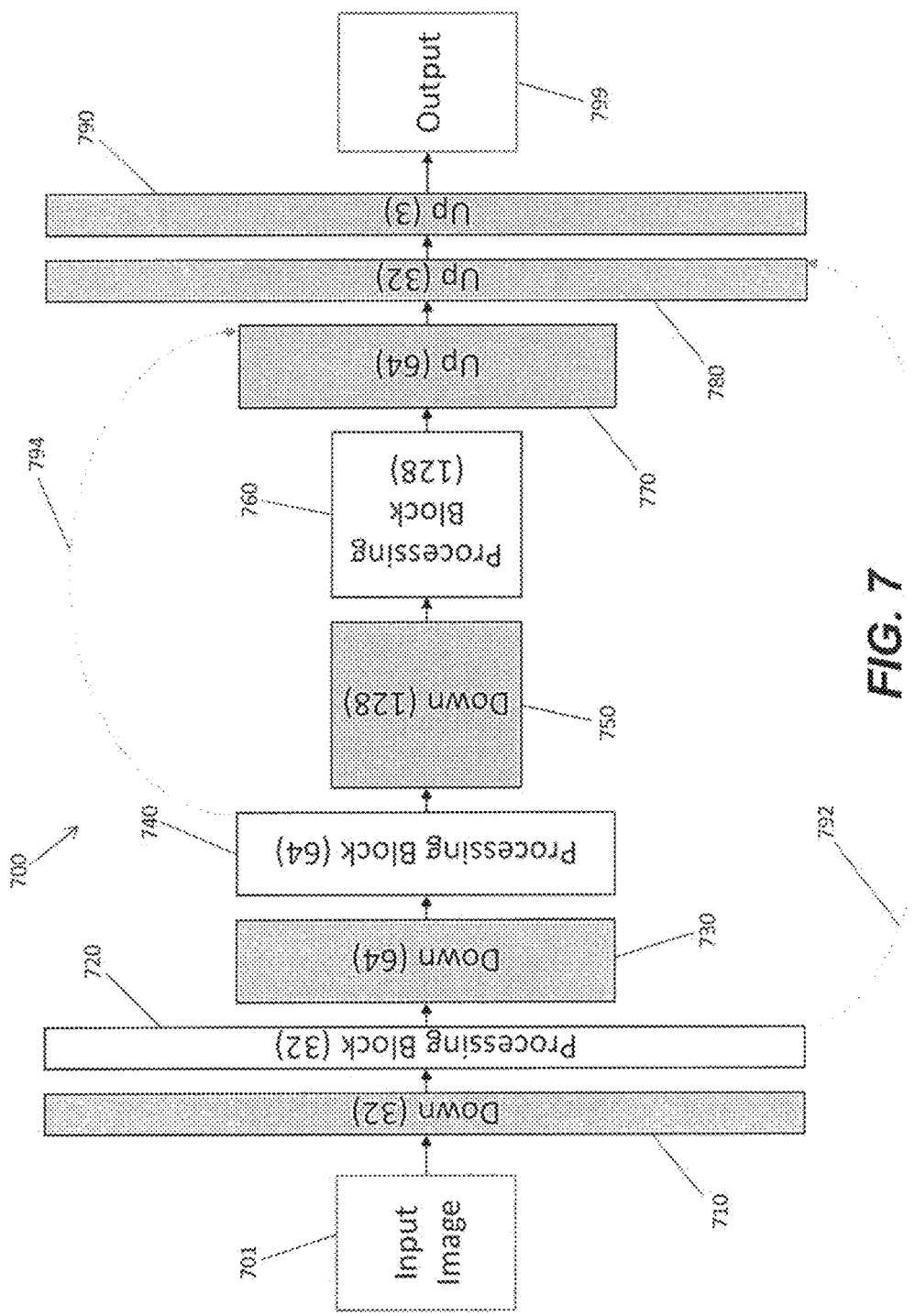
FIG. 7 illustrates a schematic diagram of a convolutional neural network in accordance with various embodiments.

In various embodiments, a neural network (or CNN) is provided, as illustrated, for example, by a neural network 700 of FIG. 7. Additional detail related to example neural networks are illustrated in FIGS. 8 and 9A-9D and will be used for reference purposes only in describing this embodiment, as the CNN features captured by FIGS. 8 and 9A-9D can be used in conjunction with the illustrated network of FIG. 7 or with various other embodiments herein.

In FIG. 7, neural network 700 includes a first down-sampling block 710, a second down-sampling block 730, and a third down-sampling block 750, with associated first 720, second 740 and third 760 processing blocks (or residual network block). First down-sampling block 710 receives an input image 701. As illustrated, each down-sampling block can be followed by its associated processing (or residual) block. The processing (or residual) block can be single or multi branched as discussed in detail below.

The CNN can comprise a plurality of down-sampling blocks (such as, for example, three as in FIG. 7), wherein each down-sampling block can comprise a down-sampling convolutional layer (Conv), a batch normalization (norm) layer, and an activation layer comprising a gating function.

Figure 8A:
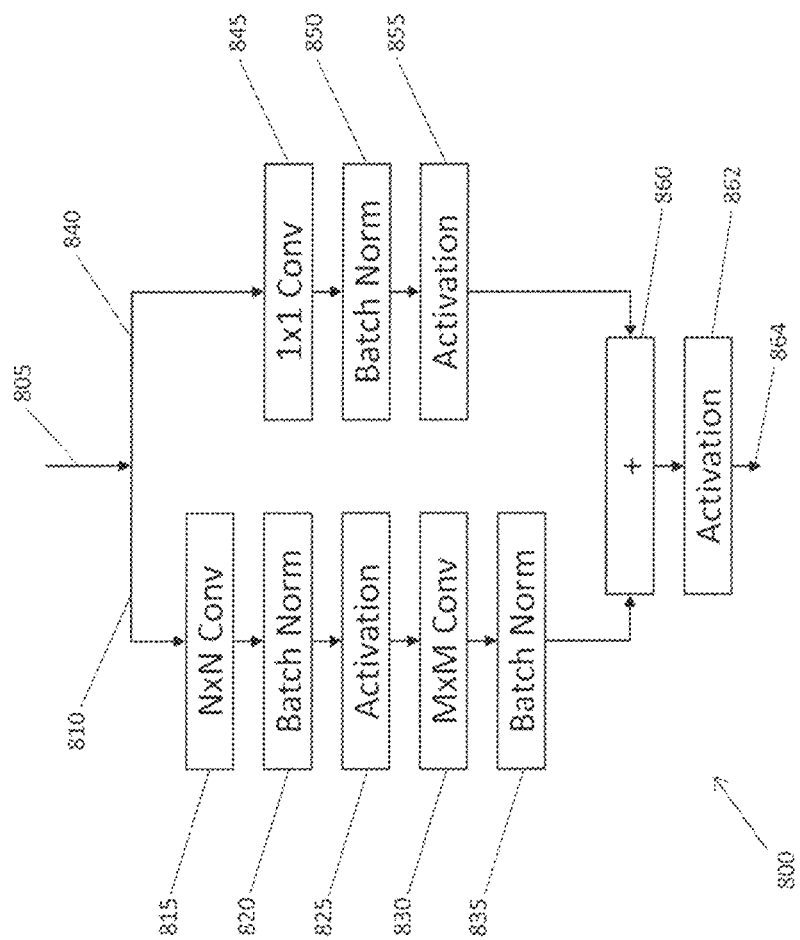
FIGS. 8A-8C illustrate schematic diagrams of a residual network, down-sampling block, and up-sampling block in accordance with various embodiments.
Figure 8B:
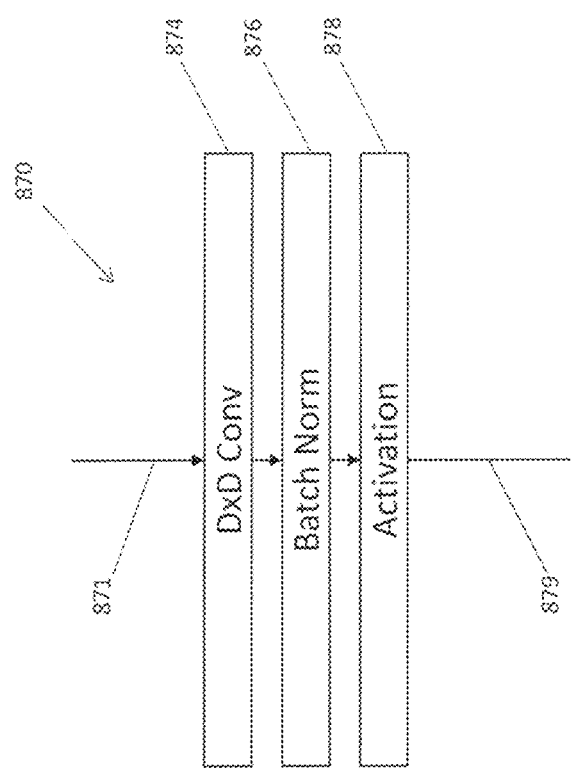

FIG. 8B illustrates as example of a down-sampling block that accepts input 871 and provides an output 879, and that includes a Conv 874 having kernel size D×D, a batch norm layer 876 and an activation layer 878. The activation layer can be, for example, an ELU or ReLU. In various embodiments, the activation layer receives image data directly from the batch norm layer, which receives image data directly from the down-sampling convolutional layer. The down-sampling convolutional layers can function to reduce the spatial resolution of image data that it receives. This will be discussed in more detail with reference to FIGS. 9A-9D.

Processing blocks (or residual network block) can be a single branch processing block or a multi-branch processing block where each branch processes outputs from a preceding down-sampling block, and then combines the output of both branches to produce a down-sampled activation map for further down-sampling, or up-sampling to a final output.

Figure 9A:
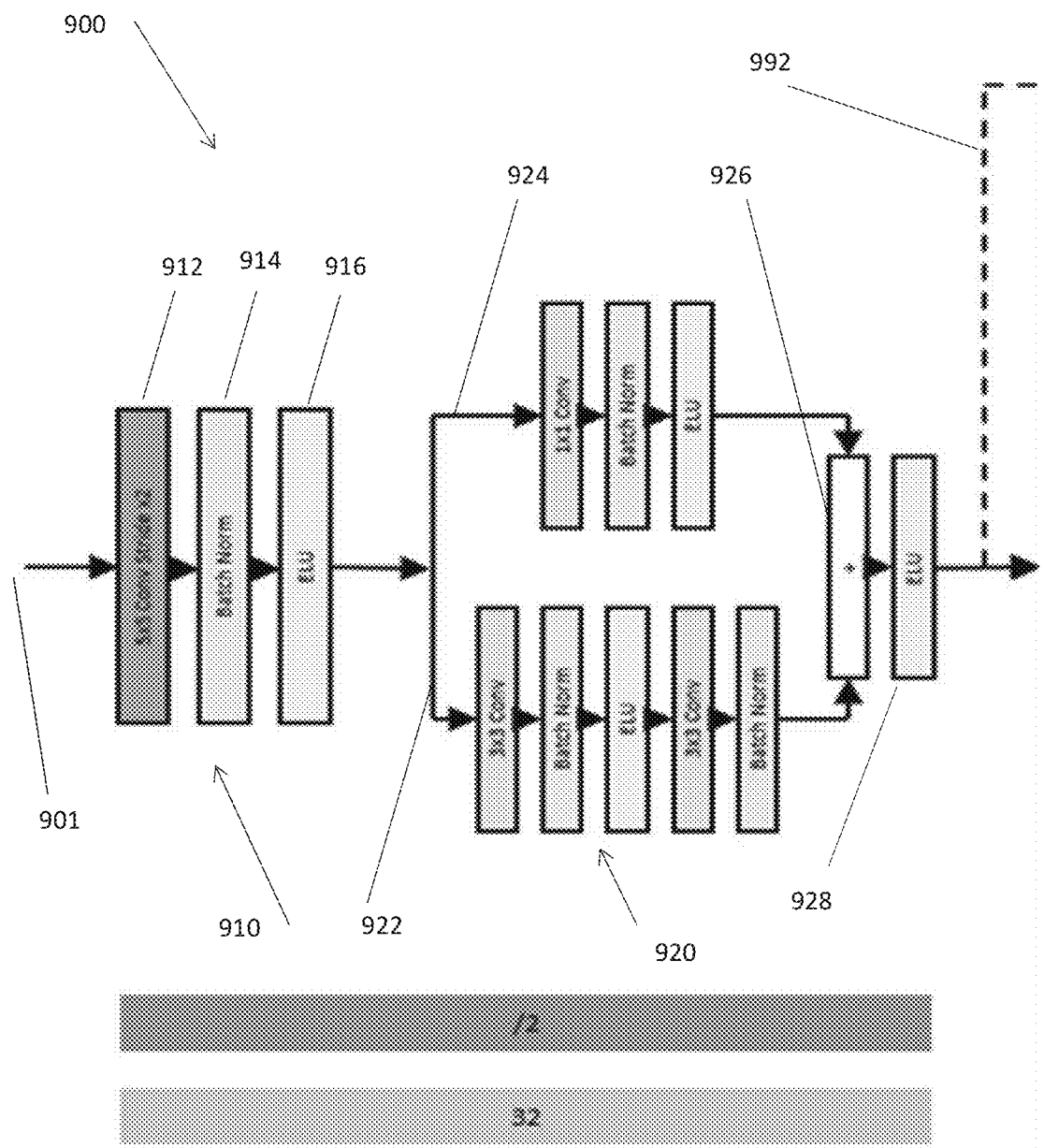
FIGS. 9A-D illustrate sections of a more detailed schematic diagram of a convolutional neural network in accordance with various embodiments.
Figure 9B:
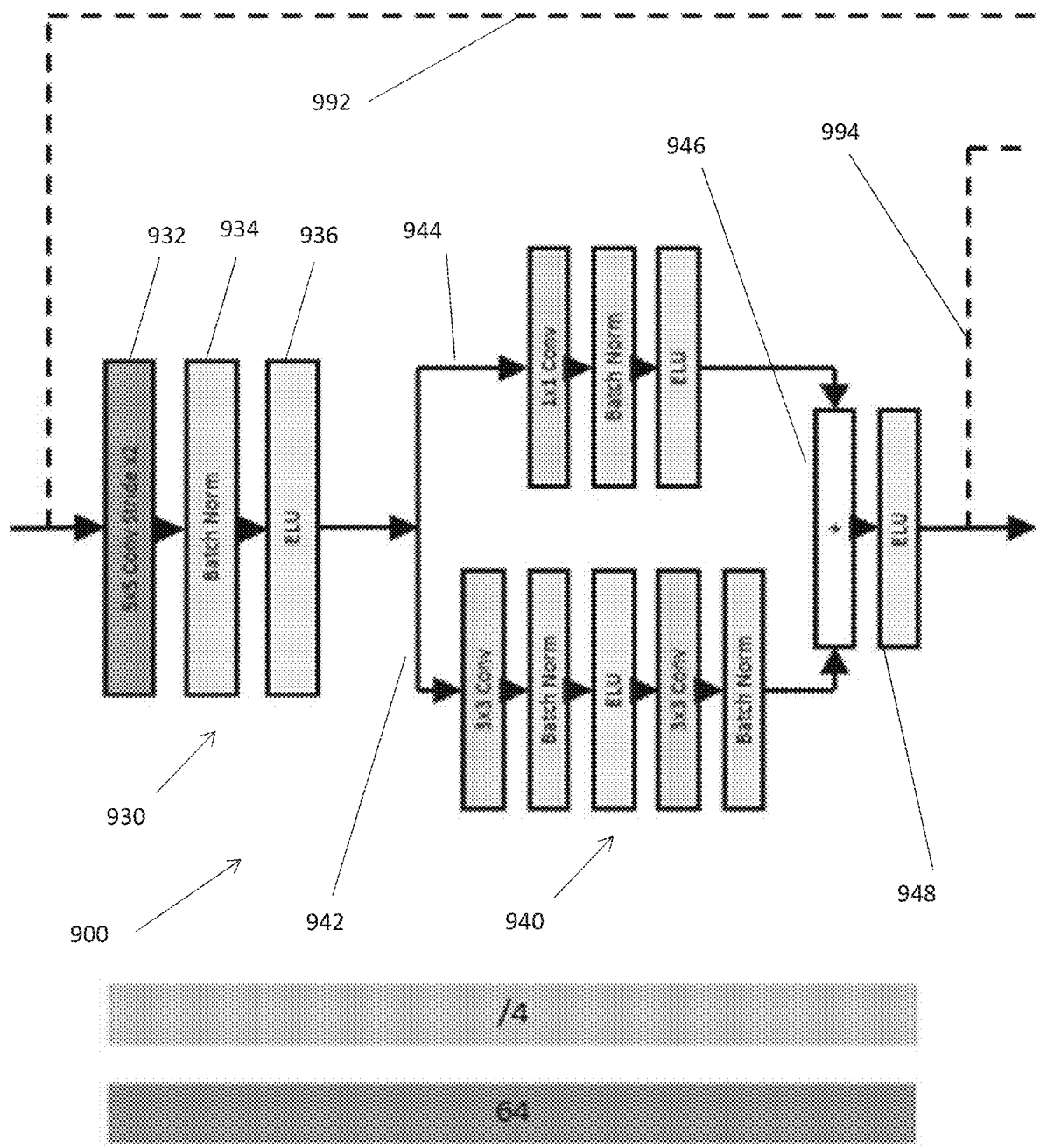
Figure 9C:
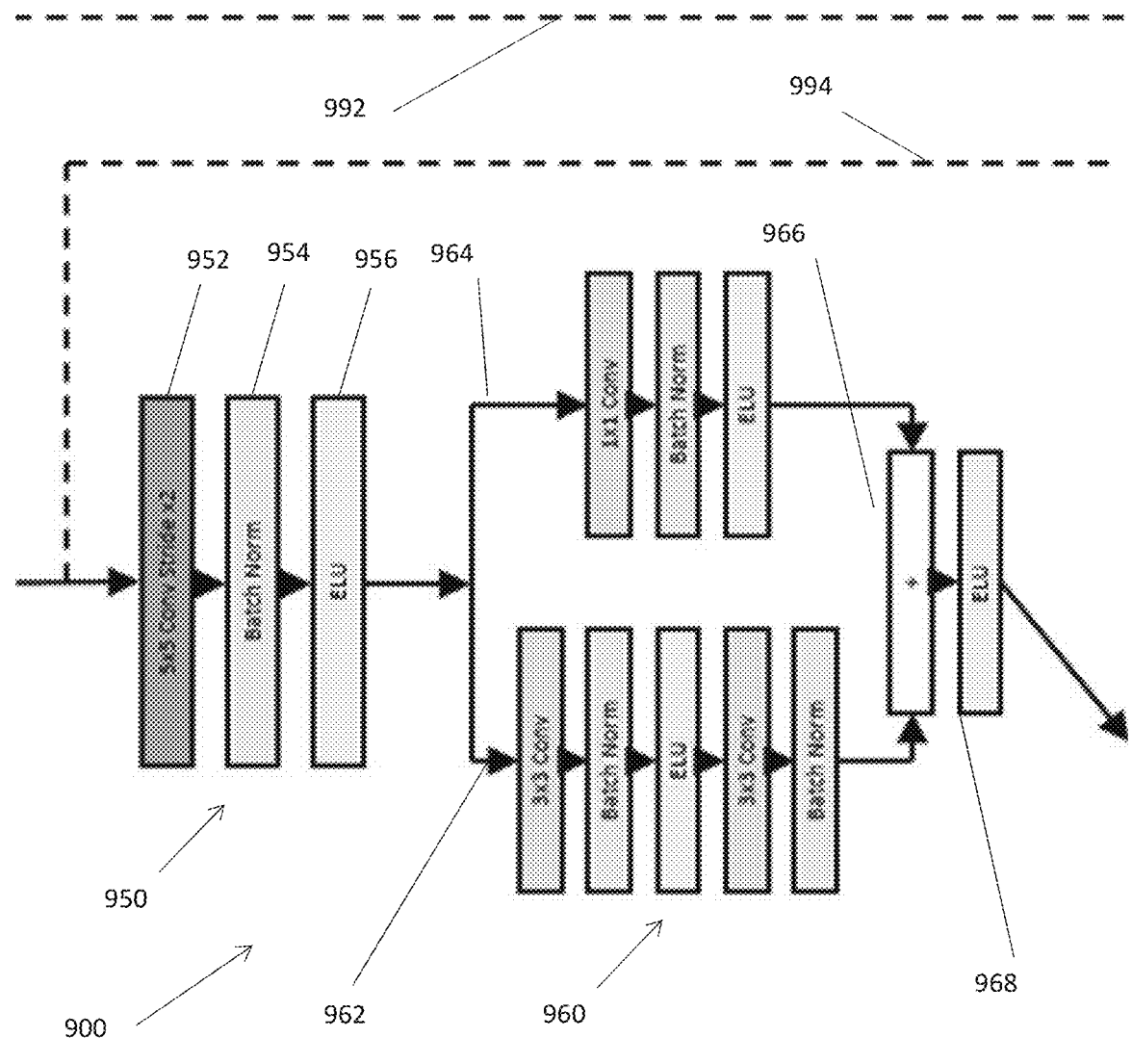

FIG. 8A illustrates an example of a multi-branched processing block 800 (or residual network block) configured to accept input 805 (e.g., in the form of an activation map) from an upstream down-sampling block (not pictured, see discussion related to FIG. 8B). Block 800 includes a first branch 810 and a second branch 840. First branch 810 includes a first convolutional layer 815 (Conv) having a kernel of N×N, a first batch normalization (norm) layer 820 that receives data from first Conv 815, a first activation layer 825 (which can include or act as a gating function) that receives data from first batch norm layer 820, a second Conv 830, having a kernel of M×M, that receives data passing through first activation layer 825, and a second batch norm layer 835 that receives data from second Conv 830. Note that the kernels of Conv 815 (N×N) and 830 (M×M) can have the same size or can differ. As illustrated in FIGS. 9A-9C (discussed below), the kernels from serial Convs in the illustrated residual networks are the same (3×3). Regardless, it is generally preferable for the Convs 815/830 to have a kernel greater than 1×1.

Second branch 840 includes a third Conv 845, a third batch norm layer 850 that receives data from third Conv 845, and a second activation layer 855 (which can include or act as a gating function) that receives data from third batch norm layer 850. Block 800 further includes a recombination layer 860 that receives data from both second batch norm layer 835 and data passing through second activation layer 855. Finally, block 800 includes a block activation layer 862 that can serve as a gating function, for data received from recombination layer 860, before an output 864 is produced from block 800 for further processing. As noted above, the activation layer can be, for example, an ELU or a ReLU. In various embodiments, the activation layer(s) is an ELU.

In FIG. 8A, second branch 840 processes image data received from a preceding down-sampling block to a lesser extent that first branch 810. In particular, the third Conv 845 of second branch 840 uses a filter window (or dimensions or kernel) of 1×1, whereas first and second Conv 815/830 of first branch 810 uses a filter window (or dimensions or kernel) of N×N and M×M respectively, which, as discussed above, will generally be greater than 1×1. These filter windows can be adjusted as needed depending on need, considering factors such as, for example, image type, image quality, object type, object size, object shape, output requirements, time constraints, stride length (discussed below), and power/processing resources. For example, first and second Conv 815/830 could use a filter window (or dimensions) of 3×3 (see FIGS. 9A-9D below illustrating this filter window size).

While both branches in FIG. 8A can have Convs with stride of one, strides can differ as well. However, to allow for recombination layer 860 to be effective, the product of multiplying the strides of Convs 815/830 on the first branch 810 must equal the stride of Conv 845 of second branch 840. Again, stride is discussed in more detail below.

The insertion of batch normalization layers before activation steps provides the advantage of helping to minimize internal covariate shift. By inserting batch norm layers as such, and by extension, after a Conv, the batch norm can normalize the output of the Conv, thus providing normalized data to the activation step, allowing for a more stable distribution of activations. By minimizing internal covariate shift during the backpropagation process, training the neural network can be done more aggressively via higher learning rates (extent of weight update), leading to faster CNN learning without the loss of efficiency and accuracy as the CNN works towards optimal parameters for the given filters in the network.

Moreover, addition of residual networks with a branch of minimally processed information (e.g., 1×1 Conv branch), allows for easier learning during training. This minimally processed branch provides a more direct pathway to trace influence of earlier parameters on a final result. In effect, this branch serves much the same purpose as a skip connection (discussed in greater detail below) within a given residual network, allowing some information to pass through the network unchanged so as not to lose spatial info that can be lost during down-sampling.

In summary, therefore, the use of residual networks alone and in combination with batch normalization layers, allows for easier and more efficient learning during training versus neural networks known in the art. This advantage is accomplished by, for example, retaining more spatial info during down-sampling and minimizing internal covariate shift. Minimizing loss of spatial info is also accomplished using striding (discussed in more detail below), which allows for more overlap during down-sampling versus known methods such as pooling, as well as skip connections, which allow for less processed information to be fed forward during the neural network process (within down-sampling steps as discussed above, and forward to up-sampling steps as will be discussed below).

By using multi-branch residual networks, particularly with one of the branches using a 1×1 filter window (i.e., not down-sampled), the neural network is allowed to further convolve the output data from the preceding Conv while maintaining the same resolution to ensure that analysis of every pixel as a single window is combined, at recombination layer 860, with data from the other branch (which may undergo multiple convolutions at a greater kernel or filter size) to output quality image data (not down-sampled from preceding Conv) that is prepared for further down-sampling.

Returning to FIG. 7, neural network 700 further includes a first up-sampling block 770, a second up-sampling block 780, and a third up-sampling block 790, with an output 799 following third up-sampling block 790. Each up-sampling block can comprise a transpose convolutional (or deconvolutional) layer, an up-sampling batch norm layer, and an up-sampling activation layer comprising a gating function.

Figure 8C:
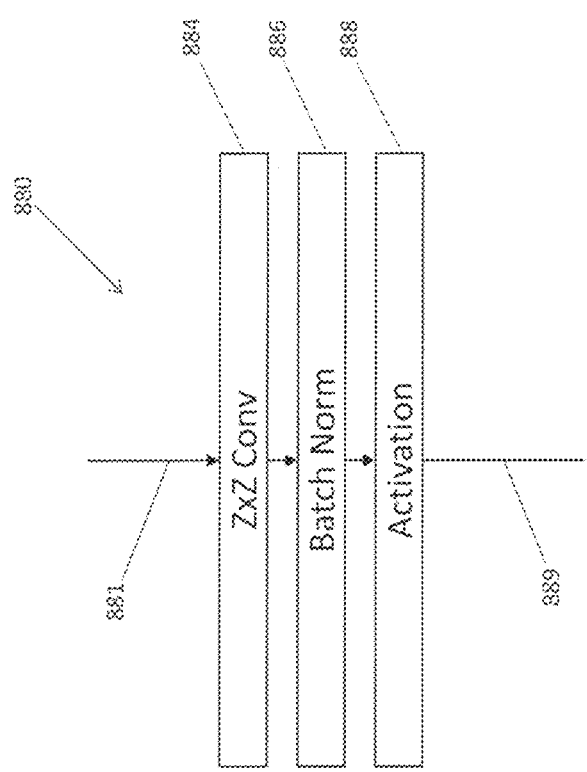

FIG. 8C illustrates as example of an up-sampling block that accepts input 881 and provides an output 889, and that includes a transpose Conv 884 having kernel size Z×Z, a batch norm layer 886 and an activation layer 888. These subcomponents will be discussed in more detail with respect to FIGS. 9A-9D. The transpose convolutional layer of each up-sampling block can be configured to increase the spatial resolution of image data that it receives, and thereby reconstruct the down-sampled output. Additionally, one or more of the up-sampling blocks can also include a recombination layer, whereby image data from the up-sampling batch normalization layer is merged with image data from a preceding residual network block (via skip connection, discussed below).

Regarding architecture of a neural network, the number of up-sampling blocks can be configured to be equal to the number of down-sampling blocks. In various embodiments, the neural network has n down-sampling blocks, n residual network (or processing) blocks, n up-sampling blocks, and n−1 up-sampling blocks that include a recombination layer (see discussion of FIG. 9D). As will be discussed in greater detail below, as spatial resolution is reduced fractionally during the down-sampling process, one may desire to increase spatial resolution at the same fractional rates. For example, if spatial resolution is halved (factor of 2) each time through a down-sampling block (or combined down-sampling and residual network block), it may be most efficient to, in turn, double (factor of 2) the spatial resolution back up to original image dimensions. This can lead to an equal number of down-sampling and up-sampling blocks.

For example, in FIG. 7, each Conv decreases spatial resolution of image data by a factor of 2 and each transpose Conv increases spatial resolution of image data by a factor of 2. The reduction in spatial resolution can be accomplished, for example, by sliding a convolutional filter (or kernel) two pixels at a time. This two pixel slide is referred to as the stride length. In the case of sliding two pixels at a time, the stride would be two. By using a stride length of 2, the Conv can down-sample by halving the dimensions of the activation map that is output from the Conv.

However, by striding, and not pooling as taught above, one can avoid loss of spatial information that can be inherent in pooling. A filter size determines how much local information gets pulled in to a single pixel analysis to affect each pixel of the next layer in the network. Generally, the filter size is odd so as to be centered on the pixel of interest. For example, a 5×5 filter will examine the surrounding 24 pixels to analyze the one center pixel of a given area. With pooling, a first area is examined to effectively determine a single value that corresponds to the pixels in that first area. Once the filter moves on to a second area, the pixels in the first area are no longer analyzed during that filter sweep. That can lead to very misleading, coarse, or inaccurate results depending on the type of image analysis conducted (e.g., object type being detected).

On the other hand, using the stride theory, once a first area is examined (a 5×5 area for example), and the two-pixel stride occurs to a second area (also at 5×5), there will clearly by overlap such that pixel points will be looked at more than once and are factored into decisions for multiple pixels, all the while still allowing for down-sampling, since the end result of a two-pixel stride sampling will result in an image output (activation map output) half the size of previous. Therefore, with striding, down-sampling would occur with much less loss of spatial info compared to pooling. Factors for determining appropriate stride length include, for example, image type, image quality, object type, object size, object shape, output requirements, time constraints, and power/processing resources.

As illustrated, if the spatial resolution of input image 701 is X, down-sampling block 710 can reduce spatial resolution by half to X/2, then X/4 by down-sampling block 730, then X/8 by down-sampling block 750. Up-sampling block 770 can then double the X/8 input to X/4, block 780 to X/2 and block 790 to X, or original size at output 799. FIG. 7 visually represents this with the decreasing height of each down-sampling block and increasing height of each up-sampling block.

As down-sampling progresses, a CNN can be designed to increase its feature complexity of processing, going from lower level feature analysis to higher level feature analysis. As discussed earlier, to further enable a CNN to detect more complex features, additional Convs can be added to analyze what outputs from the previous Conv (i.e., activation maps). For example, if a first Convs looks for a basic feature such as a curve or an edge, a second Conv can look for a more complex feature such as shapes, which can be a combination of individual features detected in an earlier Conv. By providing a series of Convs, the CNN can detect increasingly higher level features to eventually arrive at the specific desired object detection. Moreover, as the Convs stack on top of each other, analyzing the previous activation map output, each Conv in the stack is naturally going to analyze a larger and larger receptive field by virtue of the scaling down that occurs at each Conv level, thereby allowing the CNN to respond to a growing region of pixel space in detecting the object of interest.

In FIG. 7, each Conv and processing block increases channel depth by a factor of 2 and each up-sampling block decreases channel depth by a factor of 2 until the third up-sampling block 790. As illustrated, at down-sampling block 710 and processing block 720, 32 channels or filters are used. At down-sampling block 730 and processing block 740, the number of channels is 64. Finally, down-sampling block 750 and processing block 760 uses 128 channels. In reverse, up-sampling block 770 halves the channels back up to 64, up-sampling block 780 to 32 and up-sampling block 790 to three (the significance of which will be discussed in more detail below). FIG. 7 visually generally represents this increase and decrease in channel use with the increasing width of each down-sampling block and decreasing width of each up-sampling block (except final block 790).

While the rate of change in spatial resolution (original, X/2, X/4, X/8, X/4, X/2, original) is nearly the opposite that of channel depth rate (0, 32, 64, 128, 64, 32, 3, 0), this is not necessary for a CNN architecture. However, the coinciding changes in spatial resolution versus channel number advantageously allow the CNN to maximize time, processing power, and quality of output 799 by offsetting a sequential increase in filter depth with a sequential decrease in input data (activation map dimension). In effect, as the processing demands on the CNN increase with the depth of filter through each successive down-sampling block, the CNN offsets this by decreasing the image array input (activation map dimension) through each successive down-sampling block to allow the CNN to analyze smaller inputs across greater depth. Correspondingly, the reverse occurs back up the up-sampling blocks to output 799.

Reconstruction of an image volume can also be aided by a form of skip architecture. For example, skip connections inserted within a neural network can project information from an earlier down-sampling layer to a later up-sampling layer so that this earlier, minimally processed information becomes part of the reconstruction process. Without the use of skip architecture, some information that was captured in the initial Conv layers, which may greatly assist in reconstruction during up-sampling, would have been lost during the down-sampling process. In other words, such valuable information would have been down-sampled to the point that it could become too abstract for the information to be used further. Feeding this information from the primary layers to the later up-sampling layers using the skip architecture allows the earlier information to be retained and used for efficient up-sampling.

In various embodiments, the neural network can include a first up-sampling block having a recombination layer that receives image data from a second residual network block (e.g., via a skip connection), a second up-sampling block having a recombination layer that receives image data from a first residual network block (e.g., via a skip connection), and a third up-sampling block that does not include a recombination layer.

In FIG. 7, for example, a first skip connection 792 and a second skip connection 794 are provided. First skip connection 792 forward feeds output information from processing block 720 at X/2 resolution to a recombination layer, post-batch norm (discussed below), of up-sampling block 780, also at X/2 resolution. Via this skip connection, the neural network provides earlier and minimally processed information, at the same resolution as the corresponding up-sampling block, to allow for more accurate and efficient up-sampling. Second skip connection 794 functions similarly by forward feeding output information from processing block 740 at X/4 resolution to a recombination layer, post-batch norm (discussed below), of up-sampling block 770, also at X/4 resolution.

As noted above. CNN's can be used for many purposes, including image classification and image detection (also object detection within an image). As such, depending on the target of the CNN, the output must answer the main question posed to the CNN. In various embodiments herein, the CNN is used in image detection. In various embodiments, the image detection can be used for detection of objects of interest. In various embodiments, the objects of interest can be micro-objects. In various embodiments, the image detection can be used for classifying the micro-objects into at least one of a plurality of micro-object types. In various embodiments, the micro-objects are biological cells. In various embodiments, the biological cells are immunological cells such as, for example, T cells, B cells, NK cells, macrophages, or combinations thereof. In various embodiments, the biological cells are cells from a cell line (e.g., CHO cells) or cancer cells. In various embodiments, the biological cells are oocytes, sperm, or embryos.

Regarding the illustrated use of three channels in up-sampling block 790 of FIG. 7, in various embodiments, a system utilizing a CNN obtains a micro-object count from an image input. The system can do this by annotating a plurality of pixels of the input image, each pixel annotation of the set representing a probability that a corresponding pixel in the image represents the corresponding micro-object characteristic. From this analysis, a micro-object count can be obtained. In various embodiments, the plurality of micro-object characteristics comprises at least three micro-object characteristics. In various embodiments, the plurality of micro-object characteristics comprises at least a micro-object center, a micro-object edge, and a non-micro-object (or cell center, cell edge, and non-cell). Up-sampling block 790 of FIG. 7 illustrates this three micro-object characterization by its three channel depth. As such, the last up-sampling block 790 of FIG. 7 provides the object characterization necessary for neural network 700 to determine an accurate micro-object (e.g, cell) count.

FIGS. 9A-9D illustrates a schematic diagram of a more detailed convolutional neural network (CNN) 900 in accordance with various embodiments. The schematic diagram incorporates many of the neural network principles discussed above and, for that reason, these principles will not be repeated in detail. Note, however, that while the principles may be similar, the parameters used in the various embodiments herein all may vary based on specific reasons as discussed above, which include, for example, image type, image quality, object type, object size, object shape, output requirements, time constraints, and power/processing resources. As such, the parameters used in the schematic diagram of FIGS. 9A-9D are examples only.

Figure 9D:
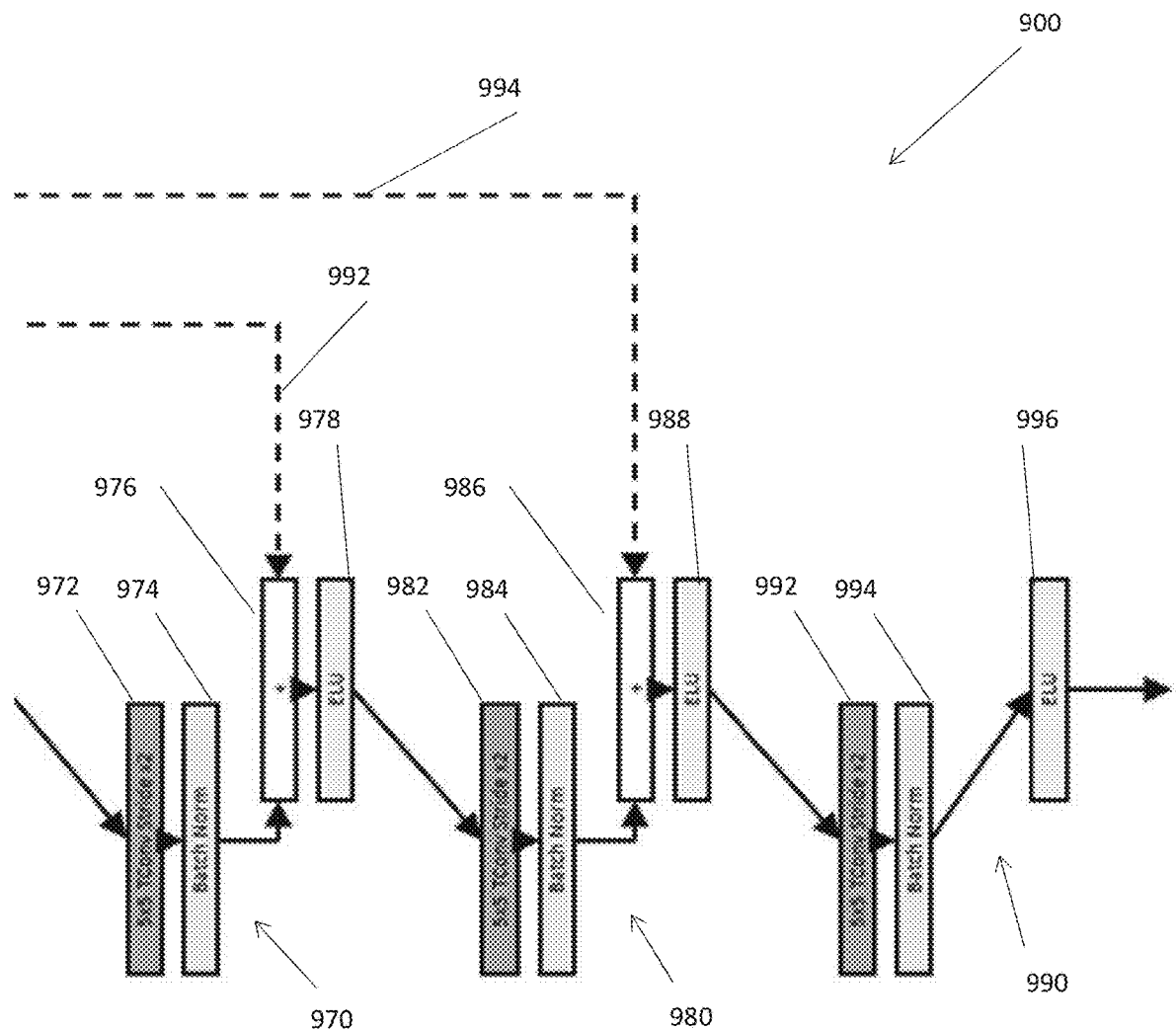

For orientation purposes, FIG. 9A, from left to right, illustrates a first down-sampling block 910 followed by a first residual network block 920, according to various embodiments. FIG. 9B shows, from left to right, a second down-sampling block 930 which receives data from first residual network block 920 (of FIG. 9A), followed by a second residual network block 940, according to various embodiments. FIG. 9C shows, from left to right, a third down-sampling block 950, which receives data from second residual network block 940 (of FIG. 9B), followed by a third residual network block 960, according to various embodiments. FIG. 9D shows, from left to right, a first up-sampling block 970, a second up-sampling block 980, and a third up-sampling block 990. First up-sampling block 970 receives data from third residual network block 960 (FIG. 9C), and includes a first up-sampling recombination layer 976 whereby data from a batch normalization layer of first up-sampling block 970 is recombined with data from a final ELU layer 948 of second residual network block 940 fed forward via a second skip connection 994. Similarly, second up-sampling block 980 includes a second up-sampling recombination layer 986 whereby data from a batch normalization layer of second up-sampling block 980 is recombined with data from a final ELU layer 928 of first residual network block 920 fed forward via a first skip connection 992.

Referring back to FIG. 9A, CNN 900 includes first down-sampling block 910 that is configured to receive an image input 901. First down-sampling block 910 includes a first Conv 912, a first batch norm layer 914, and a first activation layer 916 (e.g., an ELU in FIG. 9A). First Conv 912 can have differing parameters for kernel size and stride. Here, the kernel is 5×5 and the stride is two pixels. Output from layer 916 feeds first residual network block 920, which includes a first branch 922 and a second branch 924. See FIG. 8 for a general discussion of layout of residual networks. In first branch 922, the two Convs have kernel size of 3×3. FIG. 9A also illustrates the beginning of first skip connection 992 that feeds forward data that outputs post a first recombination layer 926 and first ELU 928, as discussed above. Note also that the scale down for this stage of CNN 900 is by a factor of 2 (down-sampled to ½ spatial resolution) and that 32 channels of features are used at this stage.

Referring to FIG. 9B, CNN 900 further includes second down-sampling block 930, which includes a second Conv 932, second batch norm layer 934 and second activation layer 936 (e.g., an ELU in FIG. 9B). Second down-sampling block 930 is configured to receive output from first ELU 928. Second Conv 932 can have differing parameters for kernel size and stride. Here, the kernel is again 5×5 and the stride is again two pixels. Output from layer 936 feeds second residual network block 940, which includes a third branch 942 and a fourth branch 944. See FIG. 8 for a general discussion of layout of residual networks. In first branch 942, the two Convs have kernel size of 3×3. FIG. 9B also illustrates the beginning of second skip connection 994 that feeds forward data that outputs post a second recombination layer 946 and second ELU 948, as discussed above. Note also that the scale down for this stage of CNN 900 is by a factor of 2 versus the previous stage of FIG. 9A (down-sampled to ¼ spatial resolution versus original) and that 64 channels of features are used at this stage.

Referring to FIG. 9C, CNN 900 includes third down-sampling block 950, which includes a third Conv 952, a third batch norm layer 954, and a third activation layer 956 (e.g., an ELU in FIG. 9C). Third down-sampling block 950 is configured to receive output from second ELU 948. Third Conv 952 can have differing parameters for kernel size and stride. Here, the kernel is again 5×5 and the stride is again two pixels. Output from layer 956 feeds third residual network block 960, which includes a fifth branch 962 and a sixth branch 964. See FIG. 8 for a general discussion of layout of residual networks. In fifth branch 962, the two Convs have kernel size of 3×3. Note also that the scale down for this stage of CNN 900 is by a factor of 2 (down-sampled to ⅛ spatial resolution) and that 128 channels of features are used at this stage.

Referring to FIG. 9D, CNN 900 includes first up-sampling block 970, second up-sampling block 980, and third up-sampling block 990. First up-sampling block 970 includes a first up-sampling Conv 972, a first up-sampling batch norm layer 974, first up-sampling recombination layer 976 and a first up-sampling activation layer 978 (e.g, ELU). First up-sampling recombination layer 976 is configured to receive input from first skip connection 992, combine that input with the output from first up-sampling batch norm layer 974, and feed that combined output to first up-sampling activation layer 978. As discussed above with reference to down-sampling Conv 912/932/952, up-sampling Conv layers can have differing parameters for kernel size and stride. Here, the kernel is 5×5 and the stride is two pixels for first up-sampling Conv 972. Note also that the scale up for this stage of CNN 900 is by a factor of 2 versus the output from third residual network 960 (up-sampled to ¼ spatial resolution) and that 64 channels of features are used at this stage.

Second up-sampling block 980 includes a second up-sampling Conv 982, a second up-sampling batch norm layer 984, second up-sampling recombination layer 986 and a second up-sampling activation layer 988 (e.g, ELU). Second up-sampling recombination layer 986 is configured to receive input from second skip connection 994, combine that input with the output from second up-sampling batch norm layer 984, and feed that combined output to second up-sampling activation layer 988. As discussed above with reference to down-sampling Conv 912/932/952, up-sampling Conv layers can have differing parameters for kernel size and stride. Here, the kernel is 5×5 and the stride is two pixels for second up-sampling Conv 982. Note also that the scale up for this stage of CNN 900 is by a factor of 2 versus the output from first up-sampling block 970 (up-sampled to ½ spatial resolution) and that 32 channels of features are used at this stage.

Third up-sampling block 990 includes a third up-sampling Conv 992, a third up-sampling batch norm layer 994, and a third up-sampling activation layer 996 (e.g, ELU). Layer 996 produces an output 999 for CNN 900. As discussed above with reference to down-sampling Conv 912/

932/952, up-sampling Conv layers can have differing parameters for kernel size and stride. Here, the kernel is 5×5 and the stride is two pixels for third up-sampling Conv 992. Note also that the scale up for this stage of CNN 900 is by a factor of 2 versus the output from second up-sampling block 980 (up-sampled to original spatial resolution) and that three channels of features are used at this stage.

As discussed above in relation to FIG. 7, in various embodiments, a system utilizing a CNN obtains a micro-object count from an image input. The system can do this by annotating a plurality of pixels of the input image, each pixel annotation of the set representing a probability that a corresponding pixel in the image represents the corresponding micro-object characteristic. From this analysis, a micro-object count can be obtained. In various embodiments, the plurality of micro-object characteristics comprises at least three micro-object characteristics. In various embodiments, the plurality of micro-object characteristics comprises at least a micro-object center, a micro-object edge, and a non-micro-object (or cell center, cell edge, and non-cell). Up-sampling block 990 of FIG. 9D illustrates this three micro-object characterization by its three channel depth. As such, the last up-sampling block 990 of FIG. 9D provides the object characterization necessary for neural network 900 to determine an accurate micro-object (e.g, cell) count.

In accordance with various embodiments, systems and methods for automatically detecting micro-objects in an image are disclosed. In various embodiments, the micro-objects are biological cells. In various embodiments, the biological cells are immunological cells such as, for example, T cells, B cells, NK cells, macrophages, or combinations thereof. In various embodiments, the biological cells are cells from a cell line (e.g., CHO cells) or cancer cells. In various embodiments, the biological cells are oocytes, sperm, or embryos. In various embodiments, the biological cells are bacteria. In various embodiments, the biological cells are fungi, such as yeast or filamentous fungi. In various embodiments, the bacteria or fungi are exposed to a hypotonic solution prior to imaging and detection, thereby swelling the cells and facilitating their detection.

Figure 10:
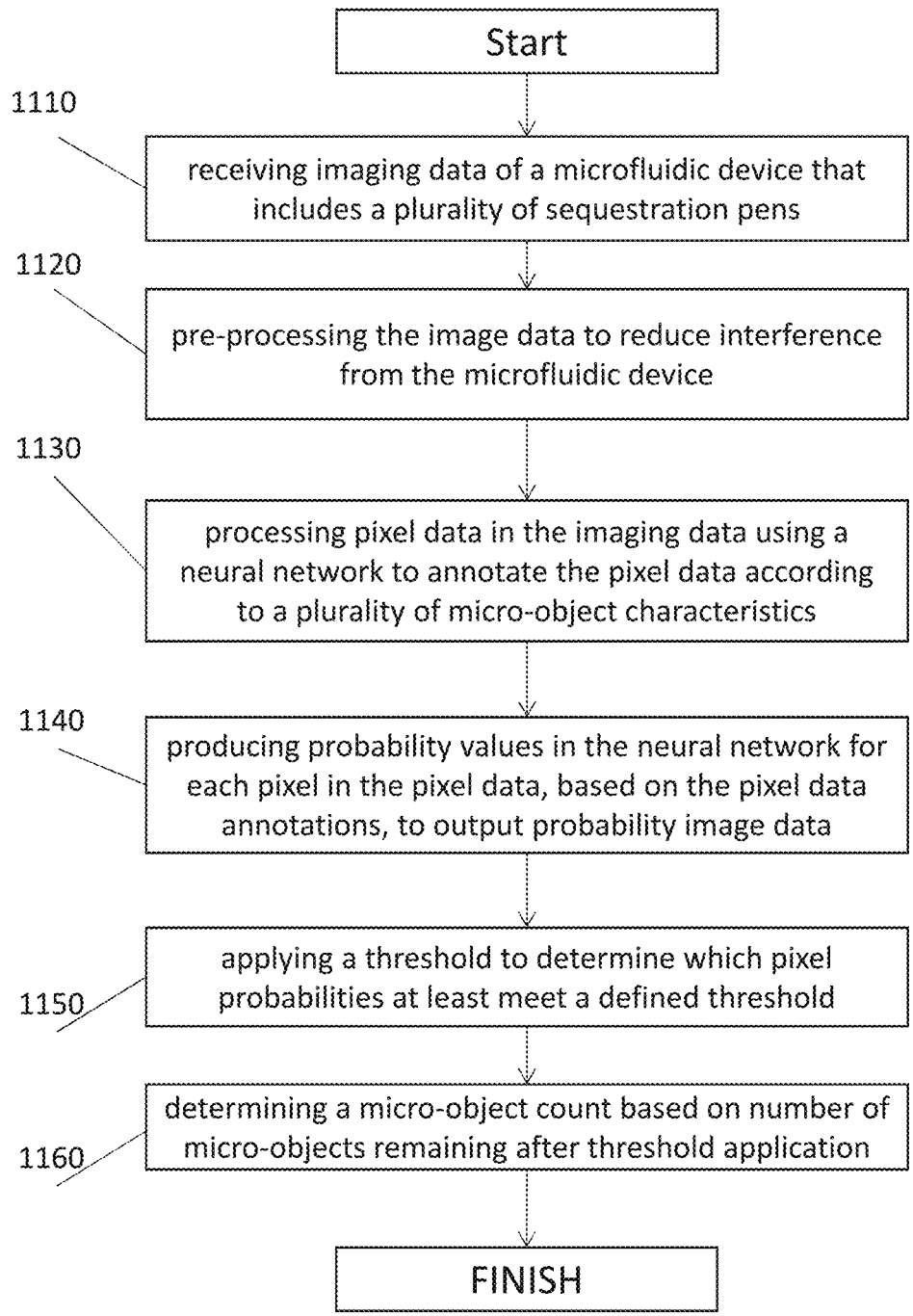
FIG. 10 illustrates a flow chart of a method for automatically detecting micro-objects in an image in accordance with various embodiments.

FIG. 10 is an exemplary flow chart illustrating a method for automatically detecting micro-objects in an image, in accordance with various embodiments. The exemplary flow chart can be carried out on, for example, a system 1200 of FIG. 11, as will be described in detail below. As depicted herein, step 1110, which can be carried out by an imaging element 1206 of an image acquisition unit 1202 of system 1200, includes receiving imaging data of a microfluidic device.

As depicted herein, step 1120 details an exemplary workflow step that can be implemented by an image pre-processing engine 1208 of image acquisition unit 1202 of system 1200. In step 1120, the method includes pre-processing the image data to reduce anomalies, such as noise and/or image distortion(s), in the image data. One example of noise is a repeating pattern, such as might be associated with an internal surface of the microfluidic device.

As depicted herein, steps 1130 and 1140 detail exemplary workflow steps that can be implemented by a machine learning algorithm, such as a neural network 1210 of a micro-object detection unit 1204 of system 1200. At step 1130, the method includes processing pixel data in the imaging data using a neural network to annotate the pixel data according to a plurality of micro-object characteristics. At step 1140, the method includes outputting probability values for each pixel in the pixel data. The output probability values can be in the form of a plurality of pixel masks, each mask corresponding to a micro-object characteristic from a plurality of micro-object characteristics. Each mask can comprise a set of pixel annotations (or set of probability values) for the image in relation to the specific micro-object characteristic associated with that mask.

As depicted herein, step 1150 details an exemplary workflow step that can be implemented by a threshold engine 1212 of micro-object detection unit 1204 of system 1200. At step 1150, the method includes applying a threshold to determine which pixel probabilities at least meet a defined threshold.

As depicted herein, step 1160 details an exemplary workflow step that can be implemented by a detection engine 1214 of micro-object detection unit 1204 of system 1200. At step 1160, the method includes determining a micro-object count based on number of micro-objects identifiable after threshold application.

Figure 12:
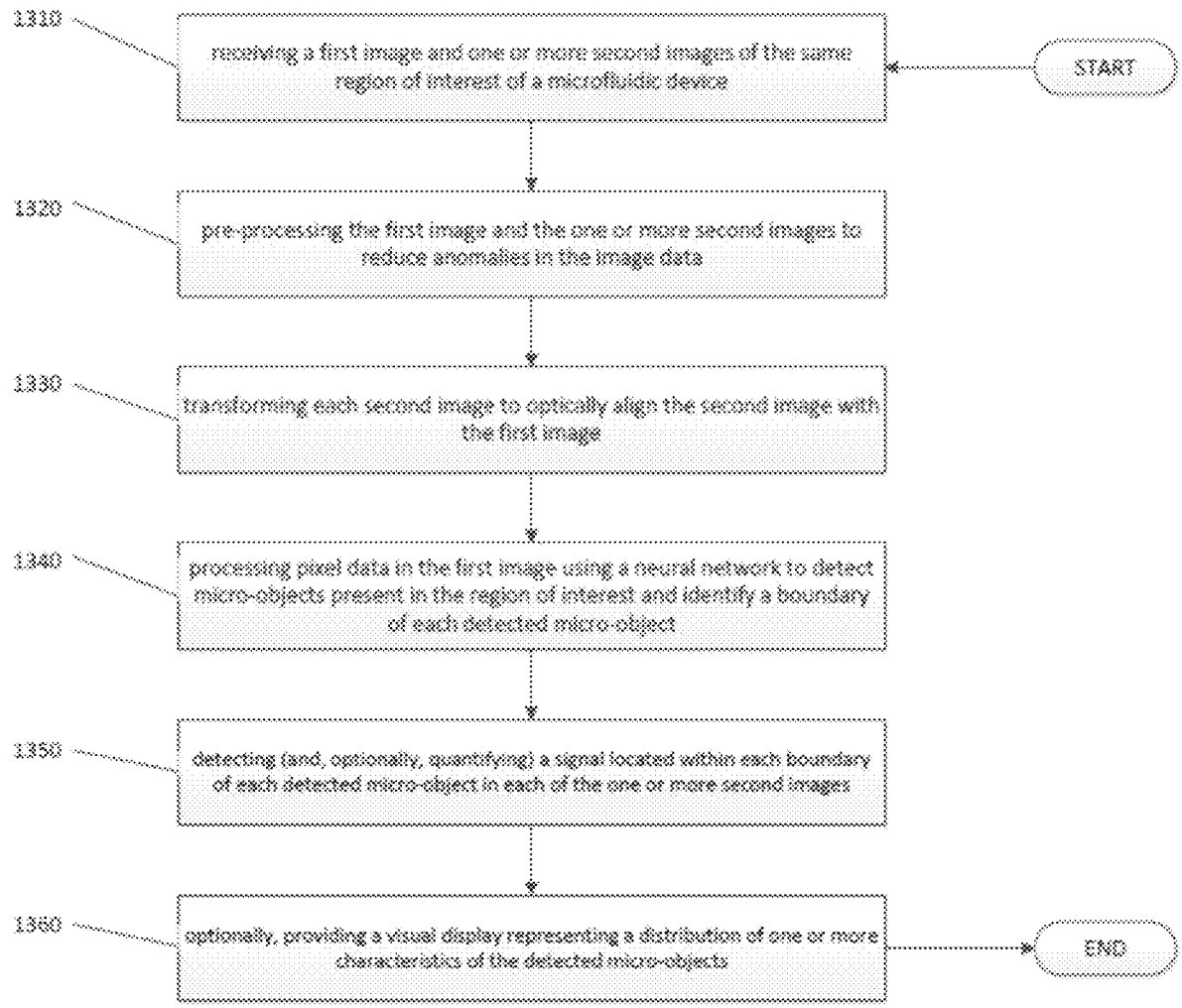
FIG. 12 illustrates a flow chart of a method for automatically detecting micro-objects in an image in accordance with various embodiments.

FIG. 12 is an exemplary flow chart illustrating a method for detecting and characterizing micro-objects in a microfluidic device, in accordance with various embodiments. The exemplary flow chart can be carried out on, for example, a system 1400 of FIG. 13, as will be described in detail below. As depicted herein, step 1310, which can be carried out by an imaging element 1406 of system 1400, includes receiving a first image and one or more second images of the same region of interest of a microfluidic device. In accordance with various embodiments, the first image can be a bright field (or "illuminated") image and each of the one or more second images can be a non-bright field (or non-illuminated) image, such as a fluorescent image, an infrared image, an ultraviolet image, or the like. In accordance with various embodiments, the first image can be a non-illuminated image (e.g., fluorescent, infrared, ultraviolet) and each of the one or more second images can be a non-illuminated image (e.g., fluorescent, infrared, ultraviolet). In accordance with various embodiments, the first image can be a non-illuminated image (e.g., fluorescent, infrared, ultraviolet) and each of the one or more second images can be an illuminated or non-illuminated image (e.g., fluorescent, infrared, ultraviolet). Although not required, the imaging element 1406 can be part of an image acquisition unit of system 1400.

In various embodiments, time lapse images can be gathered of the region of interest of the microfluidic device over a selected time period. Gathering time lapse images can also include selecting time lapse values. Time lapse values 1818 can be selected from a group consisting of time interval, time delay, total number of cycles, and combinations thereof. Time lapse image analysis can be useful in many circumstances. For example, it can be useful to track cellular mobility with cells such as, for example, T-cells. Using time lapse, micro-objects can be followed based on factors such as proximity, trajectory, and changes in any of the selectable parameters used to characterize the micro-object, such as circularity, position, brightness, etc., Moreover, an image sequence file can be maintained to capture the time lapse images, the file being configured to include a time stamp, exposure time/sequence, illumination percentage, and other variables necessary to understand changes over time.

As depicted herein, step 1320 details an exemplary workflow step that can be implemented by image pre-processing engine 1408 of system 1400. In step 1320, the method includes pre-processing the image data to reduce anomalies, such as noise and/or image distortion(s), in the first image and each of the second images. Although not required, the pre-processing engine 1408 can be part of an image acquisition unit of system 1400.

As depicted herein, step 1330 details an exemplary workflow step that can be implemented by an image alignment engine 1409 of system 1400. In step 1330, the method includes transforming each second image to optically align the second image with the first image. Although not required, the image alignment element 1409 can be part of an image acquisition unit of system 1400.

In various embodiments, each image (of the first and one or more second images) can be associated with a specific parameter such as, for example, a filter (or fluorescent) cube. Moreover, each cube can have its own focal plane (or off-set) along the z-axis. If multiple images along the z-axis are generated and analyzed, the derivative with respect to z (d/dz) of a z-stack of images can be used to identify discontinuities, which can typically correspond to the edge of a micro-object (e.g., a cell, an organelle, or the like). Furthermore, analyzed images can be false colored and layered or combined to generate composite images. This can occur after image pre-processing and alignment.

As depicted herein, step 1340 details an exemplary workflow step that can be implemented by a machine learning algorithm, such as a neural network 1410 (e.g., a CNN), of system 1400. At step 1340, the method includes processing pixel data in the first image using a neural network to detect micro-objects present in the region of interest. Detecting the micro-objects present in the region of interest can include detecting the corresponding boundary of each detected micro-object. Although not required, the machine learning algorithm can be part of a micro-object detection unit (or micro-object detection and characterization unit—see FIG. 13) 1404 of system 1400. Moreover, at step 1340 or at a subsequent step after step 1350 discussed below, detecting the micro-objects present in the region of interest can include increasing or decreasing the detected boundary of at least one, or each, detected micro-object. The increasing or decreasing of the boundary can be, for example, by a fixed value (e.g., +/−0.5 microns, +/−1.0 micron, +/−1.5 microns, +/−2.0 microns, or the like). Alternatively, the increasing or decreasing of the boundary can be, for example, by a relative value (e.g., 10%, 20%, 30%, 40%, 50%, or greater of the diameter of a micro-object). Increasing the boundary can be used to ensure that all "positive" signal is captured in each image. Increasing the boundary can be used to eliminate all signal associated with a micro-object from an image (e.g., when calculating background). Decreasing the boundary can help ensure that signal from neighboring micro-objects does not get associated with the micro-object of interest.

As depicted herein, step 1350 details an exemplary workflow step that can be implemented by a detection engine 1414 of system 1400. At step 1350, the method includes detecting a signal located within the corresponding boundary of each detected micro-object in each of the one or more second images. The signal can be, for example, a fluorescent signal. Detecting the signal can include quantifying the amount of signal Although not required, the detection engine 1414 can be part of a detection and characterization unit 1404 of system 1400.

As depicted herein, step 1360 details an exemplary workflow step that can be implemented by a data processing engine (not shown) of system 1400. At step 1360, the method optionally includes providing a visual display that corresponds to a distribution of one or more characteristics of the detected micro-objects. The visual display can be multi-dimensional (e.g., two- or three-dimensional). The visual display can identify subsets of micro-objects that share the same characteristics. Alternatively, or in addition, the visual display can allow for user input to select specific sub-populations of micro-objects. Although not required, the data processing engine can be part of a data processing unit (not shown) of system 1400.

The method of FIG. 12 can be performed in a variety of different ways. The first image can be a bright field image. Each of the one or more second images can be a fluorescence image, luminescence image, infrared image, ultraviolet image, or the like. Alternatively, the first image and each of the second images can be a fluorescence image, luminescence image, infrared image, ultraviolet image, or the like. Each image can, for example, capture signal emitted in a unique portion of the electromagnetic spectrum. The unique portions of the electromagnetic spectrum can be overlapping or non-overlapping. The micro-objects can be cells. The method can further comprise receiving a plurality of second images (e.g., two, three, four, etc.), each of which may correspond to a unique characteristic (e.g., expression of a specific biological molecule, such as a cell surface protein). The pre-processing can include computing distortion correction for each received image. Distortion correction of images can include using, for example, a lookup table computed by examining a dot array having known spacings between the dots. The transforming step can include, for example, scaling, shifting, rotating, or a combination thereof, the second image (e.g., fluorescence images) to align with the first image (e.g., bright-field image). The scaling can be linear or higher order, as needed. Shifting can occur along an X-axis or Y-axis. The neural network can be a convolutional neural network (discussed in detail above). Micro-object characteristics can include, for example, micro-object (e.g., cell) diameter, area, volume, circularity, brightness, ratio of brightness to background, location, distance to nearest neighbor micro-object, and the like.

Grouping micro-objects into sub-populations based on fluorescence, luminescence, and/or other characteristics (e.g., size, shape, distance to nearest neighbor, and the like) can be carried out in a manner similar to that of fluorescence-activated cell sorting (FACS), in which quantified fluorescent signals and, optionally, forward scatter are graphed in a two-dimensional plot allowing distinct sub-populations to be identified and selected. In general, when multiple characteristics are involved, graphical representation takes place across N dimensions, with N representing the number of characteristics involved (see above), whether that be multiple different fluorescent signals or, alternatively or in addition, various characteristics such as those example characteristics provided above. In some instances, a two-dimensional plot can be used to represent N>2 dimensions, for example, by using shape, color, and the presence or absence of symbols to denote additional information. Different shapes and colors, for instance, can represent different levels of expression of corresponding markers. The presence of symbols can denote that a marker is present at a user-selected threshold level (or greater) or the absence (at or below background) of a marker. Alternatively, the presence of symbols can represent that a corresponding micro-object is separated from its nearest neighbor micro-object by a user-selected minimum distance.

By identifying micro-objects (e.g., cells) and grouping these micro-objects into sub-populations based on shared characteristics, specific micro-objects can be selected and handled accordingly. For example, with cells, as discussed above, when grouped by characteristics, the cells can be appropriately selected to be moved into respective pens (e.g., using dielectrophoretic force) for further analysis. Such analysis can be performed on the system 150 itself or can be exported offline for analysis on applications (such as, for example, FlowJo) using any usable file format such as, for example Flow Cytometry Standard (FCS) format.

Figure 11:
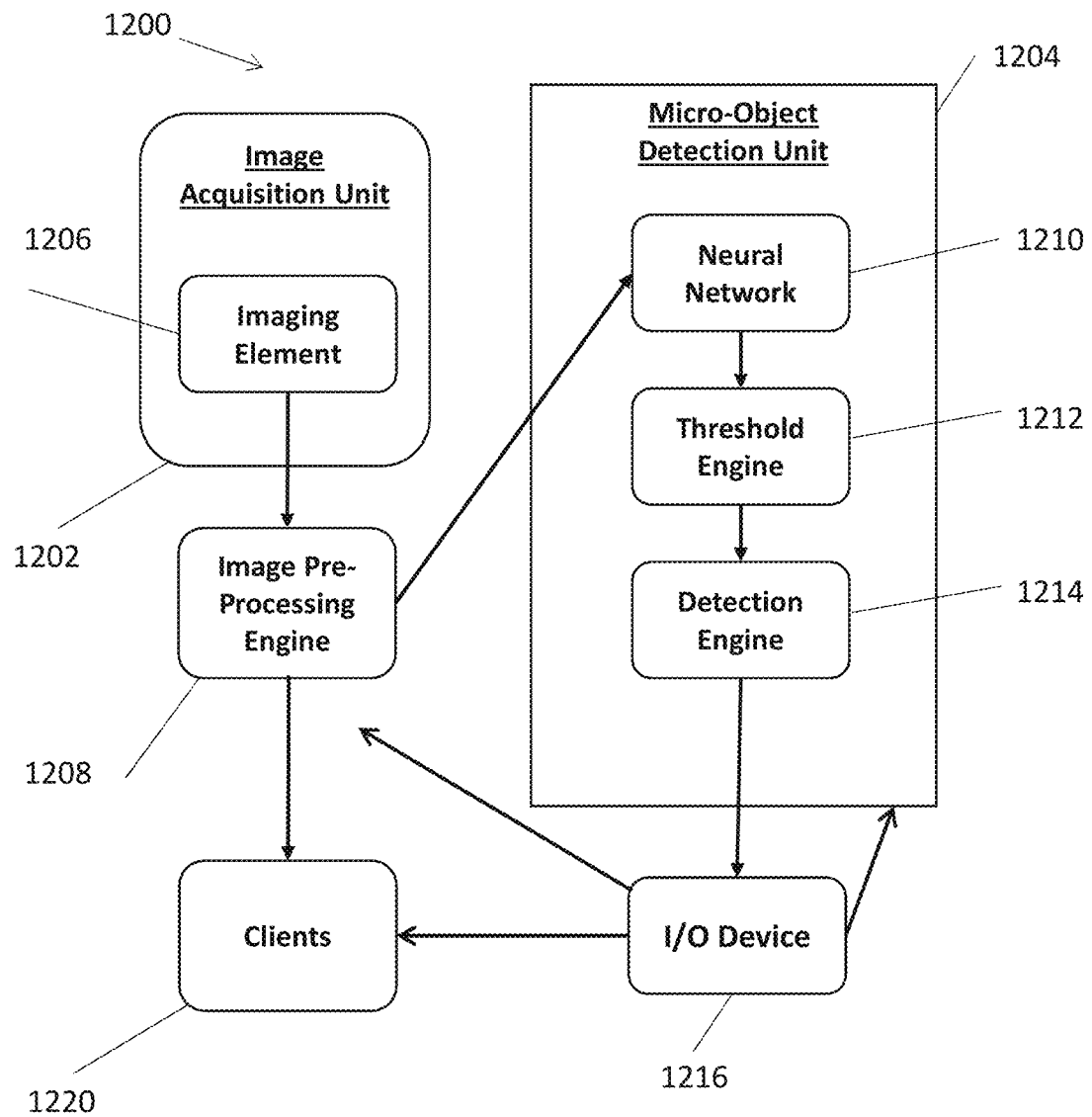
FIG. 11 illustrates a system for automatically detecting micro-objects in an image in accordance with various embodiments.
Figure 13:
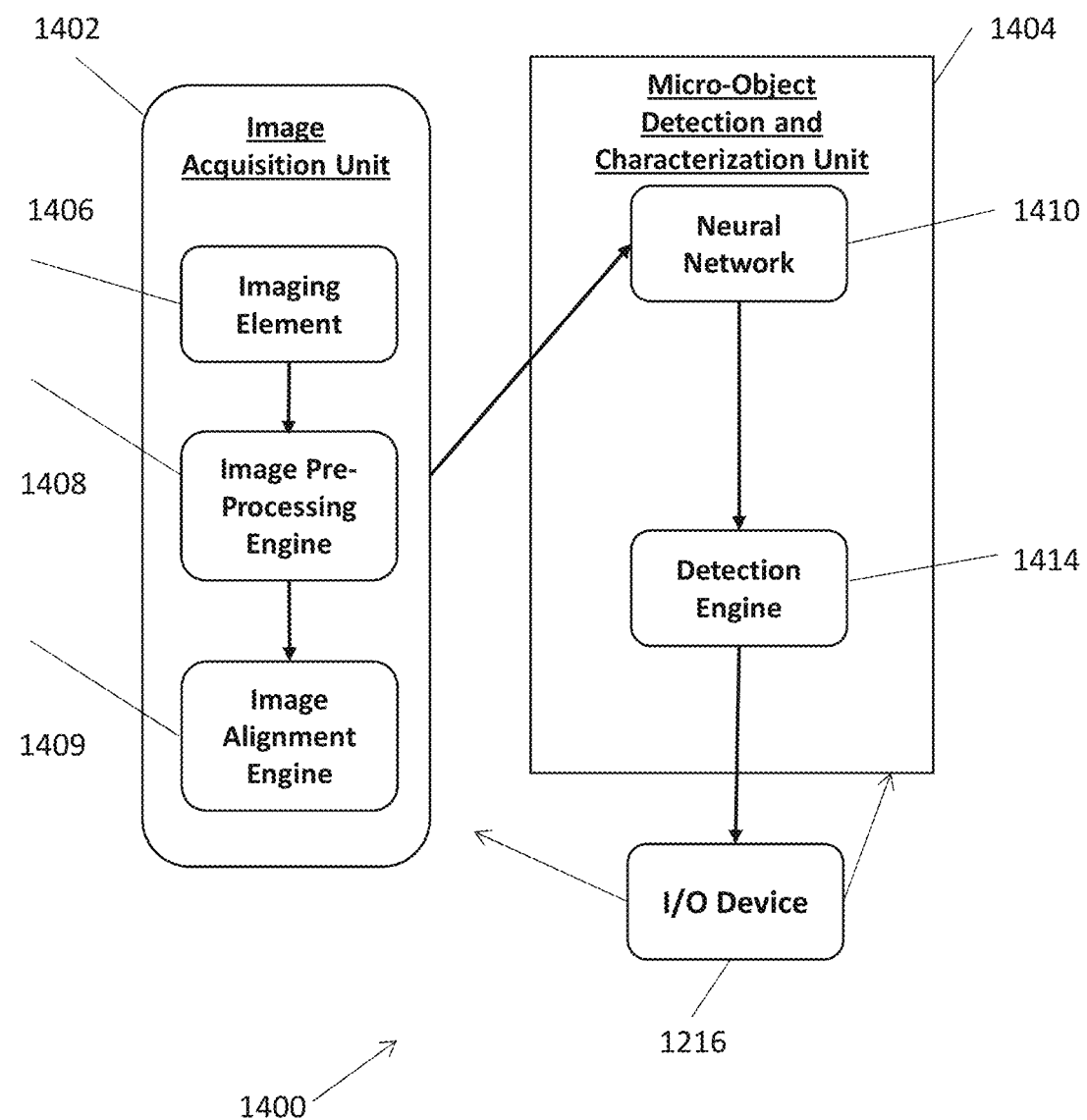
FIG. 13 illustrates a system for automatically detecting micro-objects in an image in accordance with various embodiments.

FIG. 11 is a schematic diagram of a system for automatically detecting micro-objects in an image, in accordance with various embodiments. As depicted herein, the system 1200 can include an image acquisition unit 1202, an image pre-processing engine 1208, a micro-object detection unit 1204, and an input/output device (I/O device) 1216 for outputting an image and/or final count of the detected micro-objects. FIG. 13 is another schematic diagram of a system for automatically detecting and characterizing micro-objects in an image, in accordance with various embodiments. System 1400 of FIG. 13 includes an image alignment engine 1409 but does not include a threshold engine as provided in FIG. 11 (threshold engine 1212 discussed below). The discussion below regarding system 1200 applies as well to the similar features (e.g., units, neural networks, imaging elements and engines) in system 1400.

I/O device 1216 can be configured to include, for example, an associated display device 1012 and/or input device 1014 of system 1000 (see FIG. 5), which can be in the form of data (for example, parameters, user requirements, etc) that can be transferred to, for example, image acquisition unit 1202, image pre-processing engine 1208, micro-object detection unit 1204, or combinations thereof. I/O device 1216 can also be configured to receive user input via an associated display device 1012 and/or input device 1014 of system 1000 (see FIG. 5), which can be in the form of data (for example, parameters, user requirements, etc) that can be transferred to, for example, image acquisition unit 1202, image pre-processing engine 1208, micro-object detection unit 1204, or combinations thereof. Alternatively, or in combination, input device 1014 of computer system 1000 (see FIG. 5) can also be used to directly transfer user input, parameters, and/or the like, to, for example, image acquisition unit 1202, image pre-processing engine 1208, micro-object detection unit 1204, or combinations thereof. Moreover, I/O device 1216 can be configured to display data or images received from, for example, detection engine 1214, on an embedded display device 1012. Device 1216 can also be configured to transfer data or images to a separate display 1012 for data or image display.

Image acquisition unit 1202 (such as, but not limited to, imaging module 164 depicted in FIG. 1A above) can include an imaging element 1206 (such as, but not limited to, imaging device 194). Alternatively, unit 1202 can also be configured to include (or house) image pre-processing engine 1208.

Imaging element 1206 can be configured to capture one or more images (or image data). The images can be of, for example, the plurality of chambers (e.g., sequestration pens) and/or surrounding structures (e.g., channels) of a microfluidic device. The microfluidic device can include any of the various examples described herein (such as, but not limited to, microfluidic device 100, 200, 230, 250, 280 and 290 depicted in FIGS. 1A-1C, 2A-2B, 2D and 2G-2H above). The microfluidic device can include a flow region and a chamber, or plurality of chambers, which can be fluidically connected to the flow region, wherein each of the chambers can hold one or more micro-objects. As previously noted, the chambers can be, for example, sequestration pens. It should be appreciated that the chambers can be of on any shape, size or orientation as required by the particular application that they are used for. The flow region can be a single microfluidic channel, or a plurality of microfluidic flow channels (such as, but not limited to, channel 122 as depicted in FIGS. 1A and 2A-2C above, and flow channels 264 as depicted in FIGS. 2D-2F above), which provide a single flow path or a plurality of flow paths (such as, but not limited to, flow path 106 depicted in FIGS. 1A and 2B above). The flow region can be in fluid communication with a single, or a plurality of chambers. Alternatively, the flow region may be in fluid communication with the single chamber, or a plurality of chambers, via a reversible closure such as, for example, a valve. The flow region can be configured to receive a flow of material via an inlet as previously described. The flow of material can include, for example, a flow of micro-objects, binding agent or reagents, or a flow of medium including the material.

In various embodiments, imaging element 1206 can also be configured to resize the captured image prior to sending forward for further processing. Resizing can be accomplished, for example, by binning (e.g., four pixels to one).

In various embodiments, imaging element 1206 can also be configured to receive a first image and one or more second images of the same region of interest of the microfluidic device. Such an operation is performed by imaging element 1406 of FIG. 13.

Image pre-processing engine 1208 can be configured to prepare an image for further analysis in accordance with various embodiments. For example, if the capture image was binned prior to being received by engine 1208, engine 1208 can resize the image to full size to compensate for binning. Engine 1208 can resize using, for example, linear interpolation between pixel values. Engine 1208 can flip and/or rotate the image as necessary to a desired orientation. Engine 1208 can apply a distortion correction step to the image using, for example, a lookup table computed by examining a dot array having known spacings between the dots. Engine 1208 can be provided as part of image acquisition unit 1202 (as illustrated by image pre-processing engine 1408 of image acquisition unit 1402 in FIG. 13) or can be a stand-alone engine (as illustrated in FIG. 11).

Note that system 1400 of FIG. 13 further includes an image alignment engine 1409 configured to transform each second image to optically align the second image with the first image. Alternatively, such a function can be performed by image pre-processing engine 1408, sharing the characteristics described below in relation to image pre-processing engine 1208 of FIG. 11.

In various embodiments, engine 1208 can execute a level brightness procedure across the image. For example, engine 1208 can use a polynomial best-fit correction, such as a quadratic or higher order polynomial best-fit correction. Optionally, a sine wave or exponential function could be used in lieu of polynomial function. Leveling can be achieved by multiplying the image brightness by a scaling image, with the desired multipliers of the best-fit function being determined during system calibration. Engine 1208 can also execute a radiometric correction, to subtract background brightness stemming from, for example, auto-fluorescence.

In various embodiments, sometimes fluorescent images are needed to visualize cells that can otherwise appear translucent (e.g., DAPI can be used to stain nuclei as a means of better detecting/counting certain cells). In those cases, engine 1208 can scale, shift, and/or rotate fluorescent images to align with bright-field images, with calibration being accomplished using dot array.

In various embodiments, a Fourier transform can be used to reduce interference from a conductive silicon substrate on the microfluidic device. The Fourier transform allows for a frequency representation of the image that facilitates identification of artifacts and interference associated with the conductive silicon substrate, such as a photo-transistor array. The Fourier transform of a function of time itself is a complex-valued function of frequency, whose absolute value represents the amount of that frequency present in the original function, and whose complex argument is the phase offset of the basic sinusoid in that frequency. The Fourier transform is called the frequency domain representation of the original signal. The term Fourier transform refers to both the frequency domain representation and the mathematical operation that associates the frequency domain representation to a function of time. The Fourier transform is not limited to functions of time, but in order to have a unified language, the domain of the original function is commonly referred to as the time domain.

As will be discussed in greater detail below, micro-objects of interest may have similar, confounding morphology compared to features of the microfluidic device, such as, for example, a phototransistor array. In addition, micro-objects such as cells can be relatively translucent compared to various features of the microfluidic device. Accordingly, it can be helpful to identify and remove unwanted features of the microfluidic device (e.g. photo transistor arrays, walls or circuit elements of the microfluidic device) prior to identifying micro-objects of interest. Fourier analysis can be used to remove, for example, a transistor pattern prior to micro-object detection. This step can occur within engine 1208 or, alternatively, in a post-processing step in a detection engine 1214 of micro-object detection unit 1204 (described in more detail below).

In various embodiments, the pre-processing the image can include utilizing a brightness normalization or a contrast enhancement to reduce interference from the conductive silicon substrate on the microfluidic device.

In various embodiments, engine 1208 can make a copy of the image pre-processed as described above and transfer to various 'clients' 1220 (e.g., GUI, image processing, movie creation, image capture, memory/storage/server, etc.).

In various embodiments, a watershed algorithm can be used to fill out cell boundaries on the original image input. This algorithm treats an image much like a topographical map, with objects of interests as catchment basins and the edges of those objects as watershed lines around the basins. In so doing, this image analysis method allows for a clearer definition of object boundaries (watershed lines) around objects (catchment basins).

Micro-object detection unit 1204 of system 1200 of FIG. 11 can be communicatively connected to the image acquisition unit 1202. In various embodiments, micro-object detection unit 1204 can include a neural network 1210, a threshold engine 1212 and a detection engine 1214. It should be appreciated that each component (e.g., engine, module, etc.) depicted as part of micro-object detection unit 1204 (and described herein) can be implemented as hardware, firmware, software, or any combination thereof.

In various embodiments, micro-object detection unit 1204 can be implemented as an integrated instrument system assembly with the image acquisition unit 1202. That is, micro-object detection unit 1204 and image acquisition unit 1202 can be housed in the same housing assembly and communicate via conventional device/component connection means (e.g. serial bus, optical cabling, electrical cabling, etc.).

In various embodiments, micro-object detection unit 1204 can be implemented as a standalone computing device (as shown in FIG. 11) that is communicatively connected to the image acquisition unit 1202 via an optical, serial port, network or modem connection. For example, the image processing unit can be connected via a LAN or WAN connection that allows for the transmission of imaging data acquired by the image acquisition unit 1202 to micro-object detection unit 1204 for analysis.

In various embodiments, the functions of micro-object detection unit 1204 can be implemented on a distributed network of shared computer processing resources (such as a cloud computing network) that is communicatively connected to the image acquisition unit 1202 via a WAN (or equivalent) connection. For example, the functionalities of micro-object detection unit 1204 can be divided up to be implemented in one or more computing nodes on a cloud processing service such as AMAZON WEB SERVICES™.

Neural network 1210 can be designed and configured to receive image data input from image pre-processing engine 1208, annotate pixel data in the image data according to a plurality of micro-object characteristics, assign probability values for each pixel in the pixel data based on the pixel annotations, and output probability image data. Neural network 1210 can be a convolutional neural network and can have an architecture utilizing any combination of the above-described architecture examples (see, for example, FIGS. 7, 8 and 9A-9D, and associated discussion). Neural network 1210 can, as is done by 1410 of a micro-object detection and characterization unit 1404 of system 1400, be designed and configured to process pixel data in the first image to identify respective boundaries of micro-objects present in the region of interest. The first image, as discussed above, can be a bright-field image.

Threshold engine 1212 can be designed and configured to receive output probability image data from neural network 1210 and apply a given threshold to determine which pixel probabilities at least meet a defined threshold. For example, in various embodiments, the micro-object type can be either one of a cell center, a cell border, or not a cell type and includes micro-object characteristics, such as, a circularity feature, a size feature, or both. The probability assigned to the pixel annotation can be compared to an assigned threshold to facilitate further analysis or elimination of pixels below the threshold. The threshold may be user-defined and may reclassify the pixel annotation to another type if probability for the pixel annotation is below the threshold. The probability that is assigned generally indicates the confidence of the pixel annotation. For example, a probability could be assigned as follows: 0.15 for a Border, 0.8 for a Cell Center, and 0.05 for not a cell. As a cluster of pixels are analyzed, each pixel annotation could be used with neighboring pixels to determine the likelihood of a correct identification.

Detection engine 1214 of system 1200 of FIG. 11 can be designed and configured to receive image output data, corrected for threshold analysis in threshold engine 1212, apply image post-processing techniques and output a micro-object count. Detection engine 1214 can also be, as is provided by detection engine 1414 of system 1400 of FIG. 13, designed and configured to quantify the amount of signal (e.g., fluorescence, chemiluminescence, or the like) in the second images located within the corresponding boundaries of the detected micro-objects. Quantification of signal can facilitate and improve the grouping of micro-objects into sub-populations that share the same characteristics.

Numerous post-processing techniques are contemplated with some examples provided as follows. Engine 1214 can be configured to align CAD model of sequestration pens (in the microfluidic device) to the actual image output to find precisely where pens are located. In the case of fluorescent images (depending on cell type being detected), engine 1214 can be configured to remove background by subtraction, for example, by subtracting a corresponding image obtained from a blur (image) routine. Engine 1214 can also be configured to chop an image output into individual pens for micro-object count. Engine 1214 can also apply a pixel mask that can remove any structures around the objects of interests (e.g., microfluidic device or pen walls). Finally, engine 1214 can determine a micro-object count based on the objects identifiable after threshold and post-processing. That count and output image from engine 1214 can be transferred to I/O device 1216, where it can be, for example, stored, transferred to a memory storage, further analyzed, and/or transferred to clients 1220 (see example in FIG. 11).

In accordance with various embodiments, image acquisition unit 1202 and micro-object detection unit 1204 can be integrated into a single physical unit. Alternatively, image acquisition unit 1202 and micro-object detection unit 1204 can be separably oriented, provided in independent units such that the units are still communicatively connected and able to exchange information.

Each component of micro-object detection unit 1204 described above may be hardware or may partially or entirely be a software module.

In accordance with various embodiments, a computing device for characterizing and selecting micro-objects in a microfluidic device is provided, wherein the computing device comprises a display screen. The computing device can be configured to display on the screen a menu for selecting a first parameter, e.g., selected from a provided parameter list, for characterizing a set of detected micro-objects. Parameter that can be included in the parameter list are discussed below. The computing device can also be configured to display on the screen a plot of the detected micro-object set based on the selected first parameter.

In accordance with various embodiments, the provided parameter list can be a limited list of parameters offered within the menu, each of the parameters in the list being selectable to characterize the set of detected micro-objects based on the associated parameter.

In accordance with various embodiments, the display screen can enable selection of a sub-population of the set of detected micro-objects based on at least one selected threshold value for the selected first parameter, and can enable display of the detected micro-object set by visually differentiating the sub-population meeting the at least one selected threshold from the remaining micro-objects of the detected set.

As further discussed in detail below, when observing a population of objects, creating a set of filters can specifically enable the separation of the population of objects into n distinct populations.

As stated above with reference to FIG. 5, a computing system (or device) 1000 can be provided to include an I/O device 1216. I/O device 1216 can be configured to receive user input via associated display device 1012 and/or input device 1014, which can be in the form of data (for example, parameters, user requirements, etc.) that can be transferred to various units and engines discussed previously (see, for example, FIG. 12). Alternatively, or in combination, input device 1014 of computer system 1000 can also be used to directly transfer user input, parameters, and/or the like, to various units and engines discussed previously (see, for example, FIG. 12). Moreover, I/O device 1216 can be configured to display data or images received from, for example, detection engine 1214 or other various units or engines discussed herein, on an embedded display device 1012. Device 1216 can also be configured to transfer data or images to a separate display 1012 for data or image display.

Figure 14:
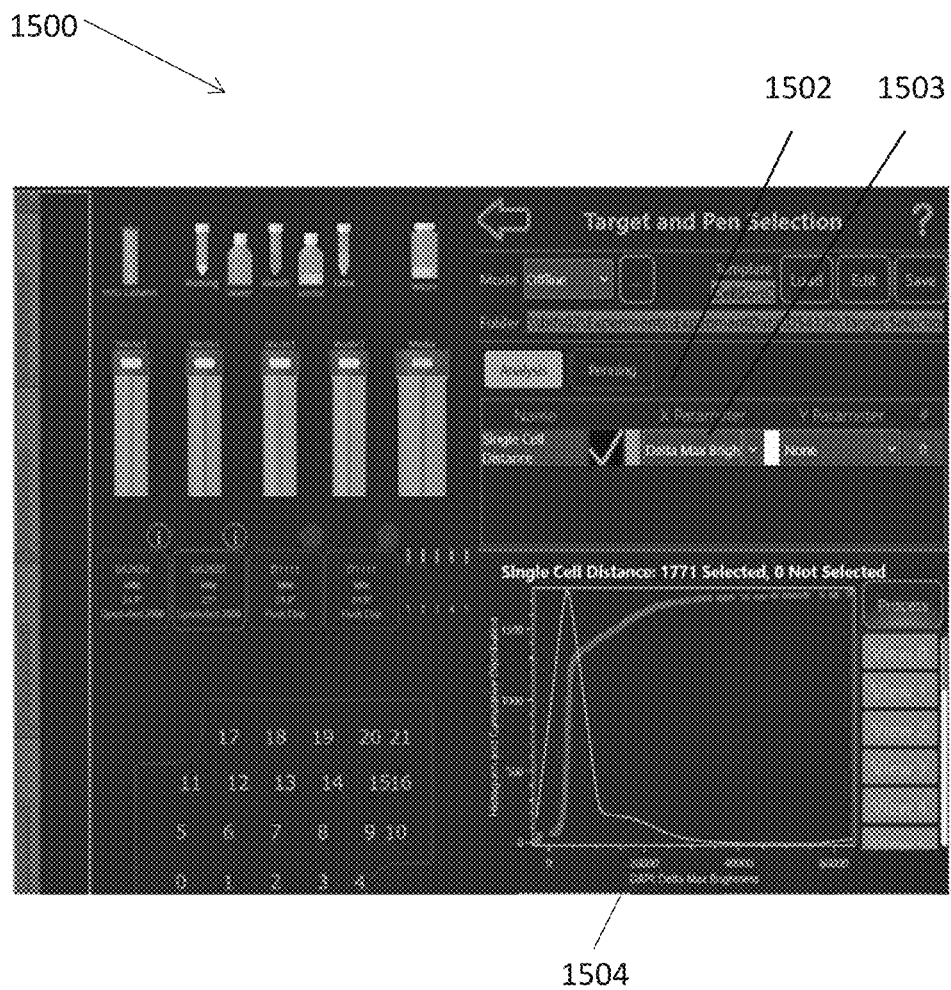
FIG. 14 illustrates a display screen for characterizing and selecting micro-objects in accordance with various embodiments.
Figure 15:
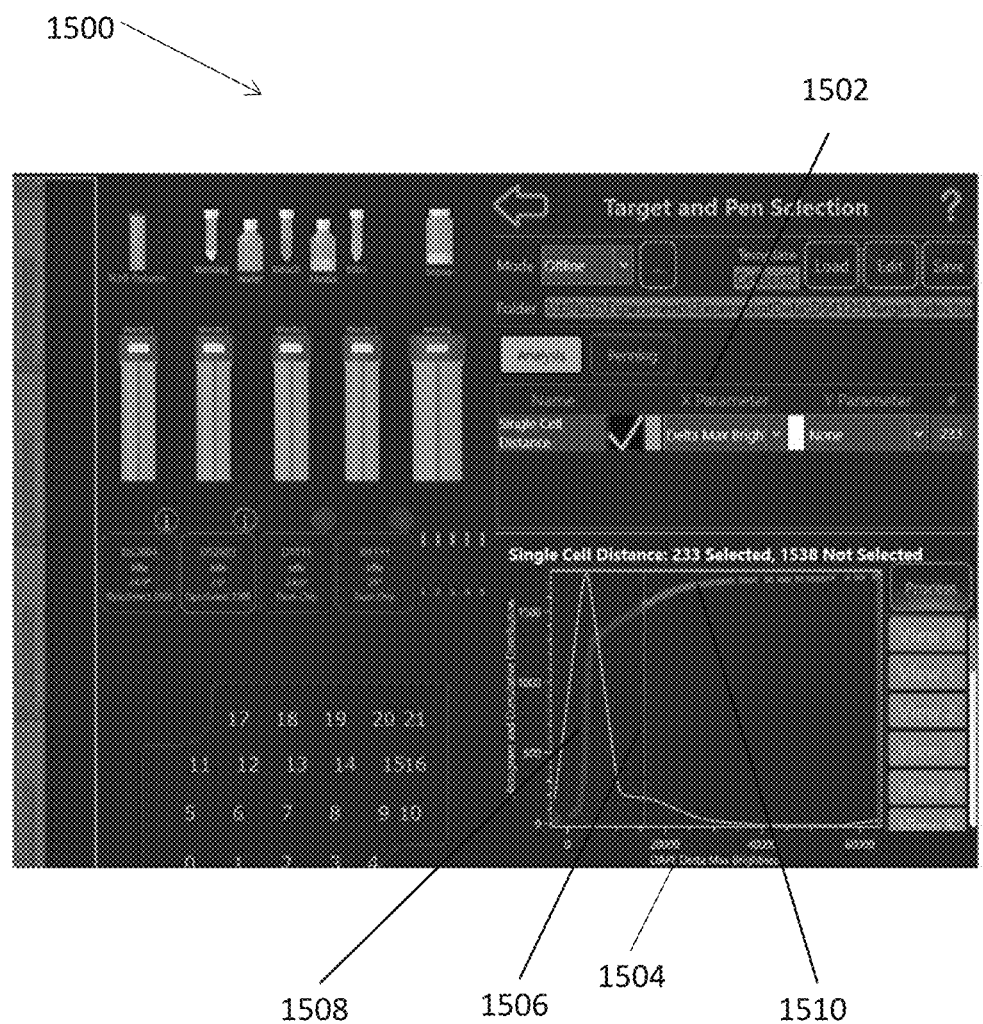
FIG. 15 illustrates a display screen for characterizing and selecting micro-objects in accordance with various embodiments.

Referring now to FIGS. 14 and 15, a display screen 1500 is provided, as part of a computing device (e.g., computing system 1000), for characterizing and selecting micro-objects in a microfluidic device. Display screen 1500 can be a graphic user interface (GUI). Screen 1500 displays a menu 1502, the menu configured for selecting a first parameter 1503, selected from a provided parameter list, for characterizing a set of detected micro-objects. The first parameter can be, for example, maximum brightness (or "Delta Max Brightness," which is a measure of brightness in which background brightness has been subtracted out), as illustrated in FIGS. 14 and 15. Taken as an example only, the display of FIGS. 14 and 15 illustrates the observation of a set of objects that have a known maximum brightness distribution under one of the fluorescent cubes (configured to detect the DAPI fluorophore, in this example) across the microfluidic device (e.g., chip). Further, in this example, a threshold value 1506 is chosen to further drill down on micro-objects of interest. In this case, the selection is for objects having a brightness that is higher than ~16000 Delta Max Brightness (i.e., max background brightness).

The provided parameter list can be, for example, a limited list of parameters offered within the menu, each of the parameters in the list being selectable to characterize the set of detected micro-objects based on the associated parameter. The provided parameter list can provides parameters selected from the group consisting of, Circularity, CentroidXPixels, CentroidYPixels, CentroidXMicrons, CentroidYMicrons. CentroidXMicronsPenRelative, CentroidYMicronsPenRelative, NearestNeighborMicrons. DiameterMicrons, VolumeFemtoliters, BackgroundAreaMicrons, MeanBrightness, MinBrightness, MaxBrightness, MedianBrightness, BackgroundMedianBrightness, DeltaMedianBrightness, DeltaMaxBrightness, LogMeanBrightness, LogMaxBrightness. LogMedianBrightness. LogDeltaMaxBrightness, LogDeltaMedianBrightnessCV, BackgroundCV, LogDeltaBrightnessMaxToBackgroundRatio, LogDeltaBrightnessSum, FluidChannelNumber, FieldOfView, CellCount, CellsPerPen.

Circularity can refer to circularity of the detected target, which can be quantified, for example, as between 0 for highly non-circular target and 1 for a perfect circle target. Can be defined by the formula 4*pi*AreaPixels/PerimeterPixels.

CentroidXPixels can refer to centroid of the target along the x-axis, which can be defined in pixels.

CentroidYPixels can refer to centroid of the target along the y-axis, which can be defined in pixels. In various embodiments, the y-coordinates on a plot can be opposite those on the associated image, so target locations can be inverted along the y-axis.

CentroidXMicrons can refer to centroid of the target along the x-axis, which can be defined in microns.

CentroidYMicrons can refer to centroid of the target along the y-axis, which can be defined in microns.

CentroidXMicronsPenRelative can refer to the position of the center of a micro-object along the x-axis of the sequestration pen in which the micro-object is located, as measured in microns from a selected origin within (or at the edge or corner) of the sequestration pen.

CentroidYMicronsPenRelative can refer to the position of the center of a micro-object along they-axis of the sequestration pen in which the micro-object is located, as measured in microns from a selected origin within (or at the edge or corner) of the sequestration pen.

NearestNeighborMicrons can refer to number of microns from nearest detected target DiameterMicrons can refer to the effective measured target diameter in microns, as computed from area.

VolumeFemtoliters can refer to an estimation of the volume of a micro-object, which can primarily depend on the shape of the micro-object and its diameter (or major and minor axes, if the micro-object has an ellipsoidal shape).

BackgroundAreaMicrons can refer to the area used in background calculation, defined in microns. This can be referred to as the area of a 'donut' around the selected target, excluding pen walls and nearby detected targets. BackgroundAreaPixels is the same parameter, except defined in pixels instead of microns.

MeanBrightness can refer to the mean brightness of the area inside the detected target boundary.

MinBrightness can refer to the minimum brightness of the area inside the detected target boundary.

MaxBrightness can refer to the maximum brightness of the area inside the detected target boundary.

MedianBrightness can refer to median brightness of the area inside the detected target boundary.

BackgroundMedianBrightness can refer to the median brightness of the background area around the detected target.

DeltaMedianBrightness can refer to the difference between the median brightness of the detected target and the median brightness of the surrounding background area.

DeltaMaxBrightness can refer to the difference between the maximum brightness of the detected target and the median brightness of the surrounding background area LogMeanBrightness can refer to the Log (base 10) value of the mean brightness of the detected target.

LogMaxBrightness can refer to the Log (base 10) value of the maximum brightness of the detected target.

LogMedianBrightness can refer to the Log (base 10) value of the median brightness of the detected target.

LogDeltaMaxBrightness can refer to the Log (base 10) value of the difference between the maximum brightness of the detected target and the median brightness of the surrounding background area LogDeltaMedianBrightness can refer to the Log (base 10) value of the difference between the median brightness of the detected target and the median brightness of the surrounding background area.

CV stands for Coefficient of Variation, which can represent the ratio of the standard deviation of the target brightness to the median target brightness.

BackgroundCV stands for Coefficient of variation of the background area, which can represent the ratio of the standard deviation of the background brightness to the median background brightness.

LogDeltaBrightnessMaxToBackgroundRatio can refer to the Log (base 10) value of the difference between max target and median background brightness, divided by the median background brightness.

LogDeltaBrightnessSum can refer to the Log (base 10) value of the difference between the mean target and median background brightness, times the area (which can be in pixels).

FluidChannelNumber can refer to the fluid channel number of the channel in which the target was found. The number can be 0 to 4, but can also be a different value, such as −1 if number is not found in chip definition file.

FieldOfView can refer to the portion of microfluidic chip that can be observed by the imaging system at a single point in time. This can primarily depend on position of the imaging system relative to microfluidic chip and the power of the objective being used by the imaging system. This parameter can allow cells to be characterized on a per field-of-view basis.

CellCount can refer to a count of the number of cells detected by the imaging system; cells may be counted on a per field-of-view basis or across the entire microfluidic chip.

CellsPerPen can refer to a count of the number of cells detected in each sequestration pen.

Screen 1500 can also display a plot 1504, which can visually represent the detected micro-object set based on the selected first parameter. The display screen can enable selection of a sub-population of the set of detected micro-objects based on at least one selected threshold value 1506 for the selected first parameter, and can enable display of the detected micro-object set by visually differentiating the sub-population meeting the at least one selected threshold from the remaining micro-objects of the detected set.

The selection can occur on plot 1504 as provided in FIG. 14, with a threshold 1506 represented, in FIG. 15, as a vertical bar, differentiating a first sub-population 1508 of micro-objects from a second sub-population 1510 of micro-objects, either which can be considered to be the sub-population meeting the set threshold. In FIG. 15, second sub-population 1510 is the sub-population meeting the threshold (233 of 1538 total micro-objects). As such, the threshold can comprise an upper threshold value. Alternatively, the threshold can comprise a lower threshold value, or both a lower threshold value and an upper threshold value.

In FIG. 15, sub-populations 1508 and 1510 are differentiated by color, which may be grey scale or any color from the visual light spectrum. Visual differentiation can take many other forms including, for example, size of data points on plot (e.g., size of data point for one sub-population larger than the other) and symbols for data points (e.g, "x" for one sub-population and "*" for the other), either of which may be combined with color to increase the differentiation.

Figure 21:
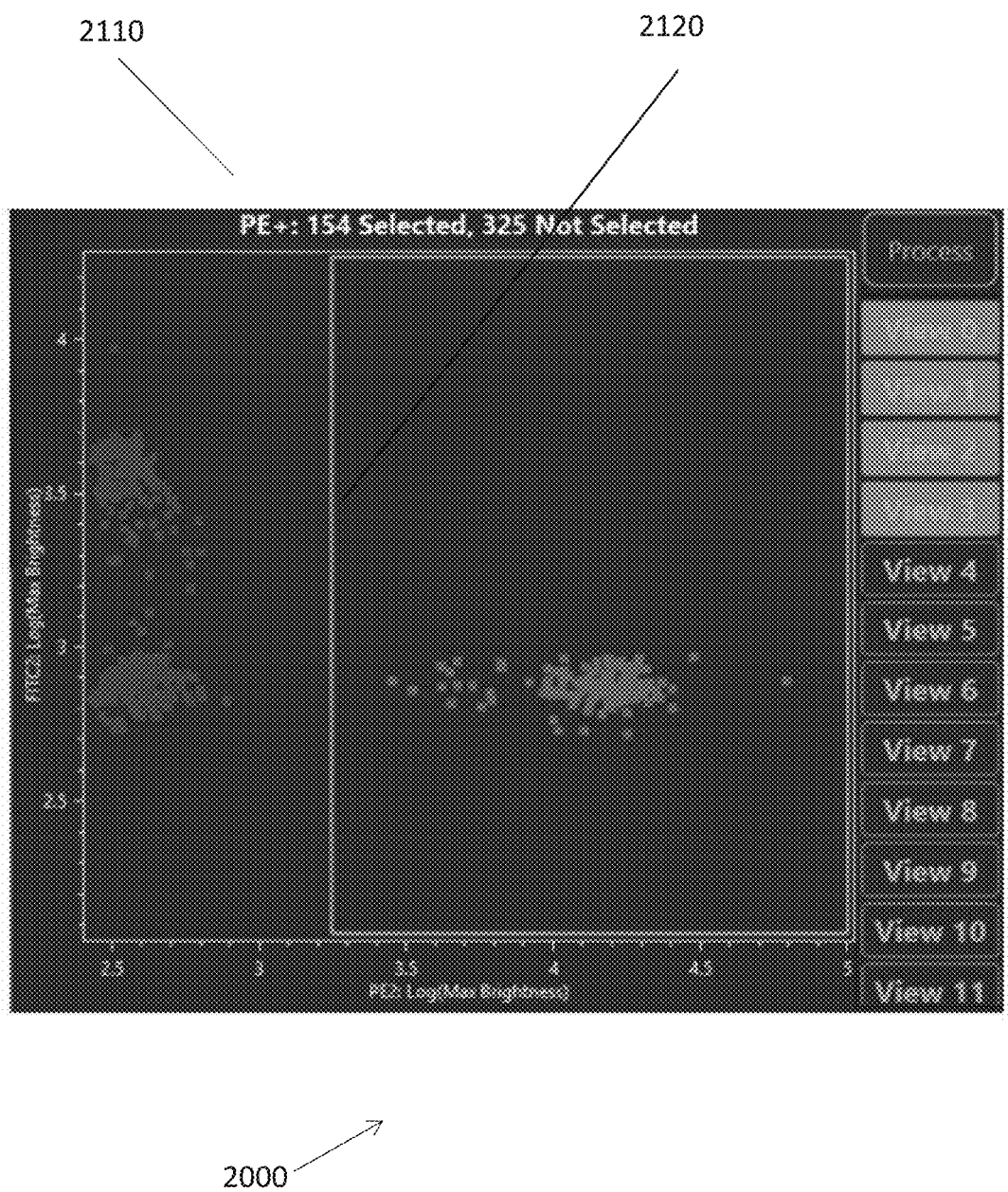
FIG. 21 illustrates a display screen for characterizing and selecting micro-objects in accordance with various embodiments.

In accordance with various embodiments, the display screen can enable a slidable selector for threshold value selection. That slidable selector can be provided, for example, as a vertical bar as illustrated in FIG. 15. Alternatively, or in addition, the display screen can enable a point selector for threshold value selection. Alternatively, or in addition, the display screen can enable a user-entered value for threshold value selection. Alternatively, or in addition, and as illustrated in FIG. 21 (described in detail below), the display can enable area selection, whereby an area of the plot is selected, within which are the micro-objects meeting the threshold. This area selection feature could be in the form of a circle, square, and any other conceivable shape necessary to define an area of interest.

Figure 16:
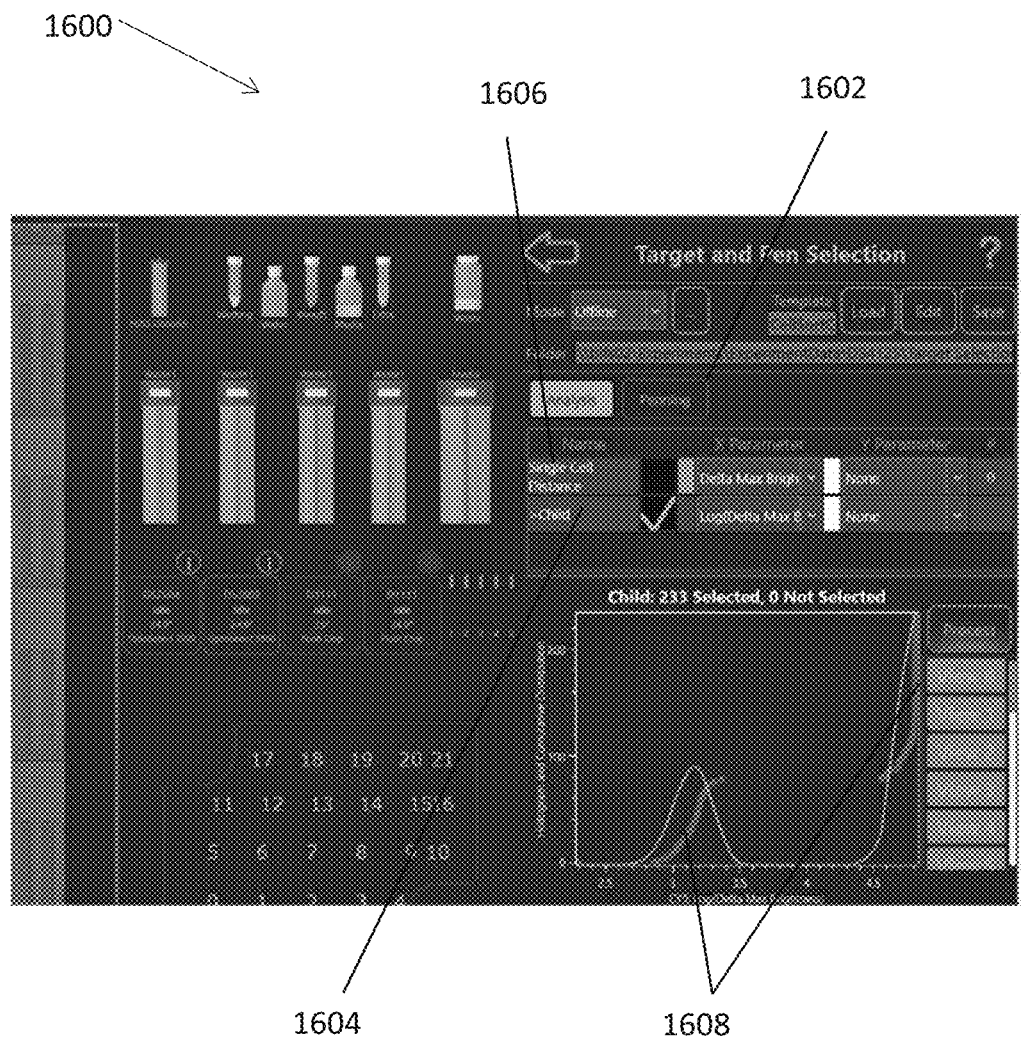
FIG. 16 illustrates a display screen for characterizing and selecting micro-objects in accordance with various embodiments.
Figure 17:
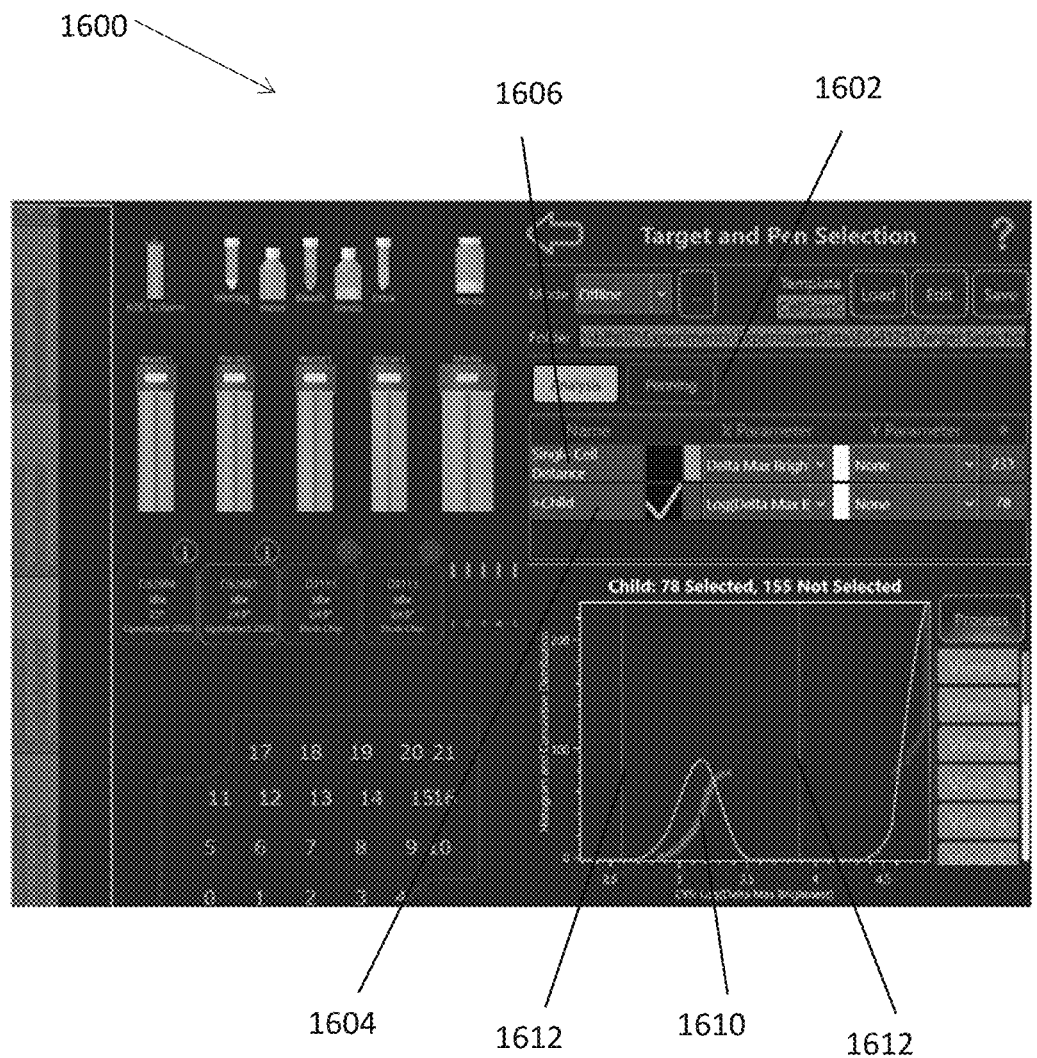
FIG. 17 illustrates a display screen for characterizing and selecting micro-objects in accordance with various embodiments.

In accordance with various embodiments, and as illustrated in FIGS. 16 and 17, a menu 1602 displayed on a screen 1600 can further be configured for selecting a second parameter 1604, selected from a provided parameter list, for characterizing the set of detected micro-objects also characterized by a first parameter 1606. In the case of the example illustrated in FIGS. 16 and 17, the second parameter is the logarithm of maximum brightness (or "LogDelta Max Brightness," which is a measure of brightness in which background brightness has been subtracted out and the resulting value is converted into a logarithmic value, which may be base 10, e, or any other suitable logarithmic base) under a fluorescent cube (configured to detect the CY5 fluorophore, in the example). The second parameter can be added as a filter underneath the first parameter (DeltaMax Brightness under a cube configured to detect the DAPI fluorophore, in this example) to analyze micro-objects under both parameters.

In accordance with various embodiments, and as illustrated in FIG. 16, the menu 1602 displayed on the screen 1600 can be associated with a plot that displays the characterization of the micro-objects based upon the selected first parameter 1606 and second parameter 1604. For example, the display screen 1600 can be further enabled to display a plot of the sub-population 1608 of detected micro-objects meeting the at least one threshold value for the first parameter 1606 and characterized by the second parameter 1604.

In accordance with various embodiments, and as illustrated in FIG. 17, the display screen can further enable selection of a subset 1610 of the sub-population 1608 of detected micro-objects based on at least one selected threshold value 1612 for the selected second parameter 1604. FIG. 17 illustrates this at least one threshold value as having both an upper and lower threshold though, as discussed herein, both either threshold value can be used individually.

In accordance with various embodiments, the computing device is further configured to accept user instructions, and/or display on the screen instructions, for repositioning one of the set of detected micro-objects, sub-population of the set of detected micro-objects, or the subset of the sub-population. The repositioning can be performed, for example, as described elsewhere herein.

Figure 18:
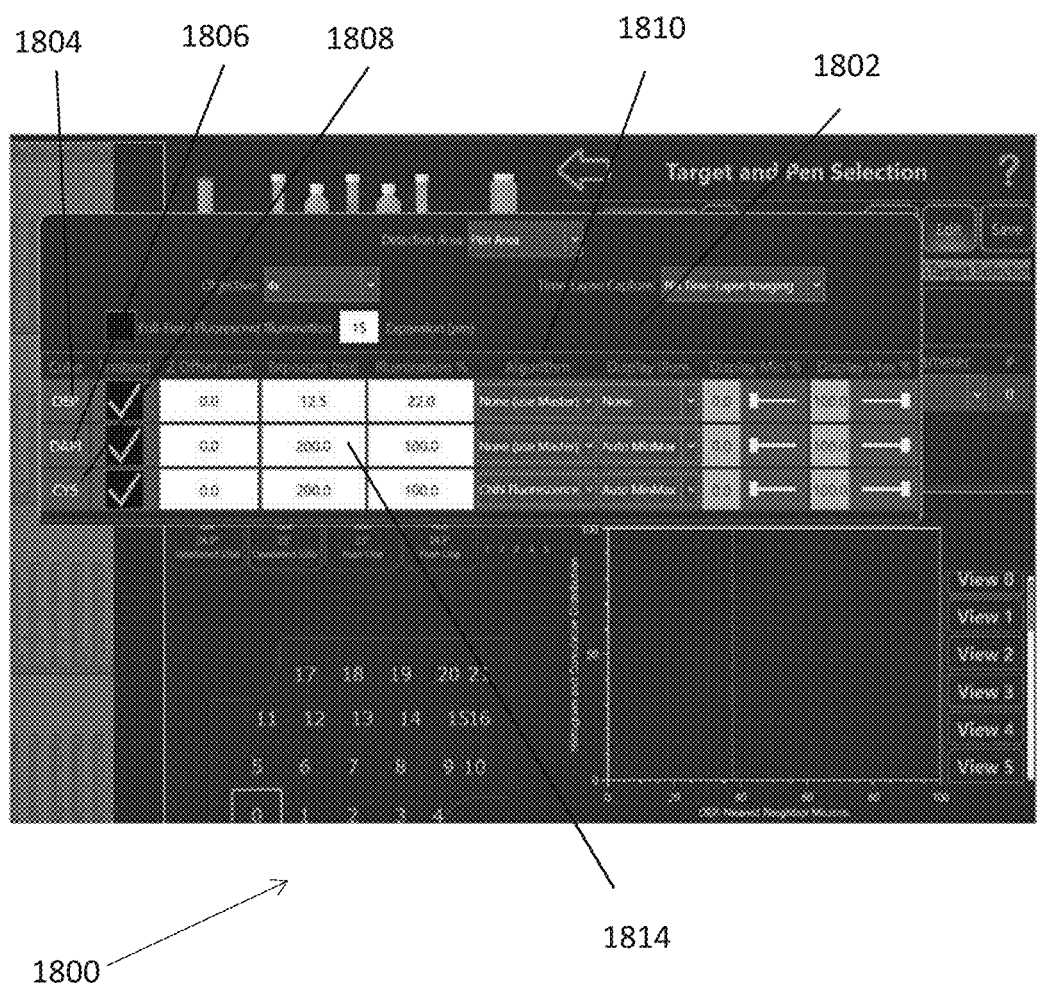
FIG. 18 illustrates a display screen for characterizing and selecting micro-objects in accordance with various embodiments.
Figure 19:
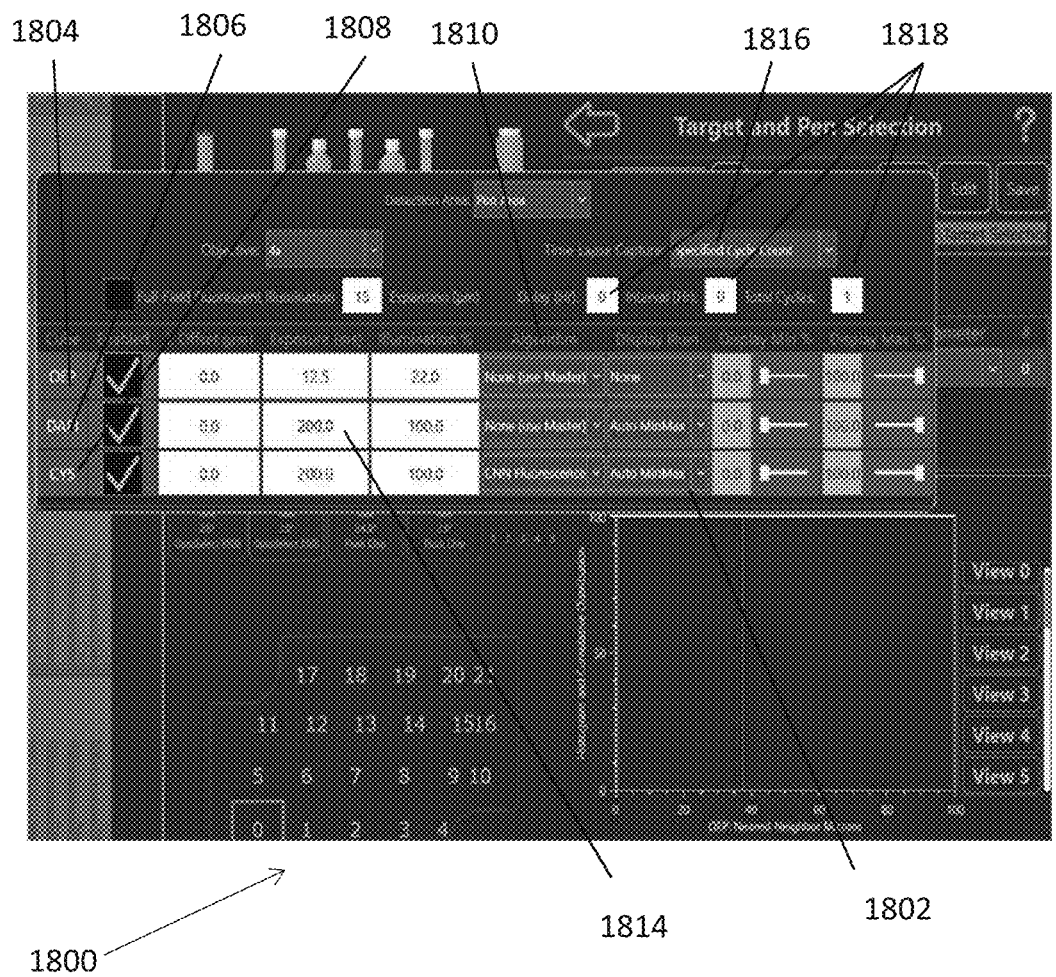
FIG. 19 illustrates a display screen for characterizing and selecting micro-objects in accordance with various embodiments.

In accordance with various embodiments, and as illustrated by FIGS. 18 and 19, the computing device 1000 can be further configured to display on a screen 1800 an imaging menu 1802 for selecting an imaging parameter 1804, selected from a provided imaging parameter list, for imaging at least a portion of the microfluidic device. The computing device can be further configured to display on the screen an imaging menu for selecting a plurality of imaging parameters 1804/1806/1808, selected from a provided imaging parameter list, for imaging at least a portion of the microfluidic device. Though FIGS. 18 and 19 illustrate three different imaging parameter selections, the number of imaging parameters is not correspondingly restricted. In various embodiments, the number of imaging parameters can range from one to five, one to ten, etc.

In accordance with various embodiments, the imaging parameter can comprise a filter or "cube" type. Cube types are selected based upon the portion of the electromagnetic spectrum that passes through the cube and is detected. Cube types can include brightfield (e.g., non-filtered, sampling the entire visible spectrum, identified as "OEP" in FIG. 18), various fluorescent filters configured to detect specific fluorescent fluorophores (e.g., DAPI, Texas Red, Cy5, FITC, and the like), infrared filters, ultraviolet filters, etc. The imaging parameter can also comprise at least one sub-parameter 1814. The at least one sub-parameter 1814, or plurality of sub-parameters, can be selected from the group consisting of illuminationPercent, exposureTimeMs, UserOffsetMicrons (across z-axis), and combinations thereof.

In accordance with various embodiments, the computing device can be further configured to display on the screen an algorithm selector 1810 for selecting an algorithm, selected from a provided algorithm list, for analyzing images acquired through each selected imaging parameter (e.g., 1804/1806/1808 of FIGS. 18 and 19), and detecting the set of micro-objects. As such, each imaging parameter can be provided with a field for selecting an algorithm to apply against that specific parameter. In various embodiments, one "Master" algorithm can be used on the image set of one of the imaging parameters (e.g., brightfield cube), and therefore locations of micro-objects detected in the master image set can be used to analyze the image sets of the other selected imaging parameters (e.g., fluorescent cubes).

In accordance with various embodiments, and as illustrated in FIG. 19, the displayed imaging menu is further configured to provide a time lapse selector 1816. The time lapse selector enables selection of time lapse values for imaging at least a portion of the microfluidic device over a selected time period. Time lapse selector 1816 can also include a selector for time lapse values 1818. Time lapse values 1818 can be selected from a group consisting of time interval, time delay, total number of cycles, and combinations thereof. Time lapse image analysis can be useful in many circumstances. For example, it can be useful to track cellular mobility with cells such as, for example, T-cells. Using time lapse, micro-objects can be followed based on factors such as proximity, trajectory, and changes in any of the selectable parameters used to characterize the micro-objects, such as circularity, position, brightness, etc. Moreover, an image sequence file can be maintained to capture the time lapse, the file being able to include a time stamp, exposure time/sequence, illumination percentage, and other variables necessary to understand changes over time.

Figure 20:
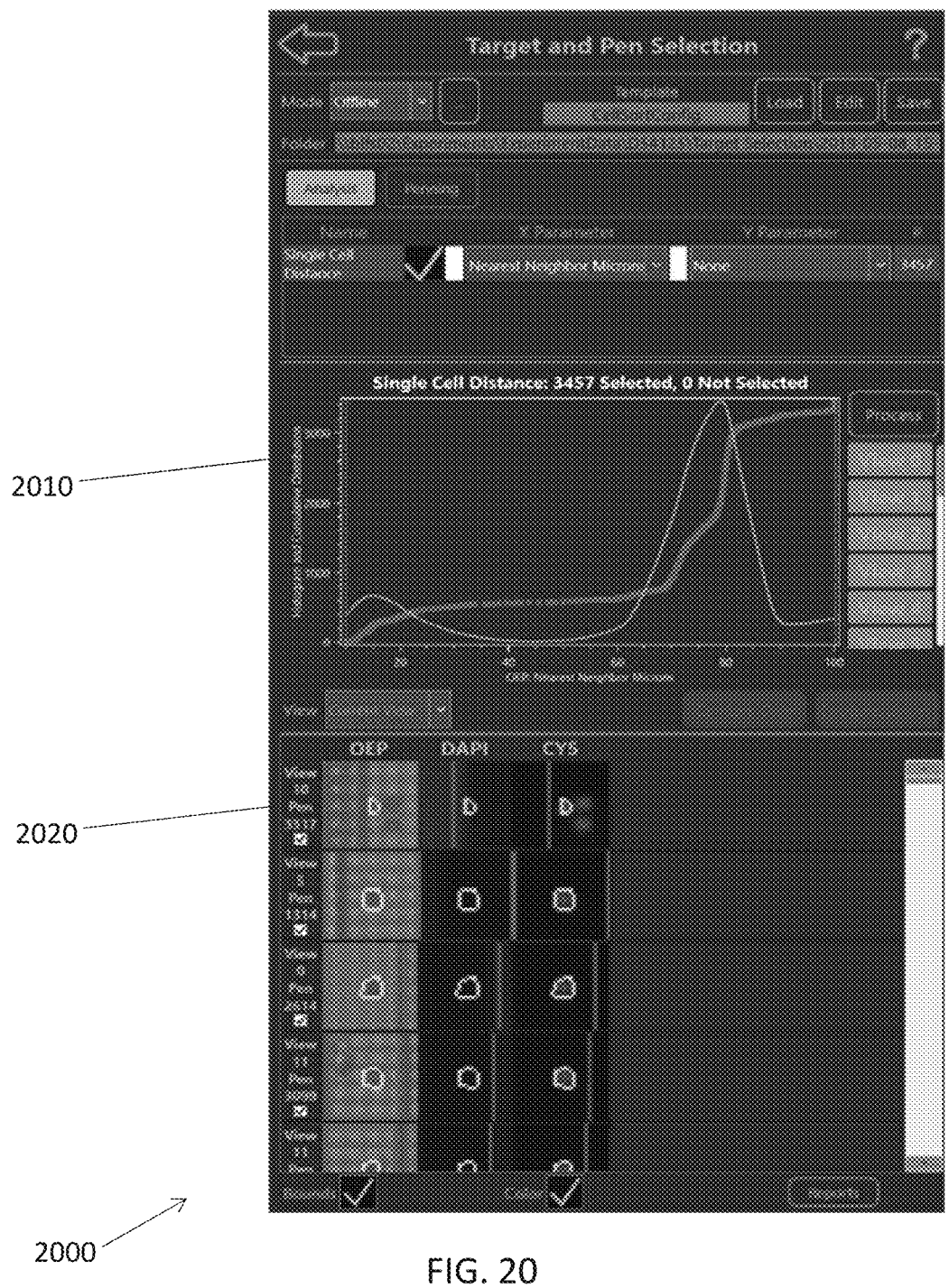
FIG. 20 illustrates a display screen for characterizing and selecting micro-objects in accordance with various embodiments.

Referring now to FIG. 20, a display 2000 is illustrated. As illustrated, the computing device can be configured to display on a screen 2010 at least one image 2020 of each individual detected micro-object. The micro-object in the microfluidic device (or cells in the microfluidic chip) can be identified in the image, for example, with a colored symbol (overlaid on or surrounding the micro-object or cell) or using a false-color display of selected micro-objects or cells. In various embodiment, the number of images displayed for each detected micro-object is equal to the number of imaging parameters selected. For example, referring to FIGS. 17 and 18, three imaging parameters were selected (i.e., OEP, DAPI and CY5). As such, the display provided in FIG. 20 shows that, for each micro-object proceeding vertically on screen 2010, three images are displayed, one for each of the OEP, DAPI and CY5 cubes. Therefore, each image can be associated with a specific parameter, a filter cube in this case. Moreover, each cube can have its own focal plane along the z-axis, or a series of images along the z-axis can be acquired. If multiple images are acquired along the z-axis, the derivative with respect to z (d/dz) of a z-stack of images can be used to identify discontinuities, which can typically correspond to the edge of a micro-object (e.g., a cell, an organelle, or the like). Furthermore, analyzed images can be false colored and layered or combined to generate composite images. This can occur after image pre-processing and alignment.

Referring now to FIG. 21, a display 2100 is illustrated. As illustrated, the computing device can be configured to display on a screen 2110 a plot of micro-objects (e.g., cells) stained with two different fluorescent markers, one of which is represented on the x-axis and the other on the y-axis. The plot also illustrates three distinct groups/types of cells, each of which can be selected either through area selection generally, or through a threshold step as discussed above. In either situation, an area of the plot can be selected, within which are the micro-objects meeting the threshold or of interest. This area selection feature 2120 could be in the form of a circle, square, and any other conceivable shape necessary to define an area of interest. In FIG. 21, cells having high levels of the marker labeled with PE2 have been selected.

Automated Detection of Micro-Objects. Methods are provided for automatically detecting a micro-object of interest in an image. The micro-object of interest may have similar, confounding morphology compared to one or more other features in the image. For example, in some instances, detection of micro-objects disposed within a microfluidic device can be complicated by features of the microfluidic device that have similar morphology to the micro-object of interest. For example, in instances where cells have a diameter of 10 microns, it may be difficult to distinguish the cells from a phototransistor array that has a 10 micron pitch in both dimensions (i.e., each phototransistor has a 10 micron×10 micron size). In addition, micro-objects such as cells can be relatively translucent compared to various features of the microfluidic device. Accordingly, it can be helpful to identify and remove unwanted features of the microfluidic device (e.g. phototransistor arrays, walls or circuit elements of the microfluidic device) prior to identifying micro-objects of interest.

In some embodiments, a single pixel can correspond to an area in the microfluidic device that is substantially smaller than the cross-sectional area of a micro-object of interest. For example, the micro-object may have a cross-sectional area of about 80 microns$^2$, whereas a pixel may correspond to an area of about 2 microns$^2$. In such embodiments, one or more clusters of pixels will be required to cover the cross-sectional area of the micro-object (e.g., in the foregoing example, it would take substantially 40 pixels to cover the cross-section area of the micro-object, or 24 pixels to cover the cross-sectional area of the circumference of the micro-object).

The analysis of a set of pixel clusters can further comprise a number of other features aside from the area and circumference of the pixel clusters. The set of pixel clusters may be analyzed according to global morphology (i.e. the size and shape of the set of one or more pixel clusters), local morphology (i.e. the size and shape of the individual pixel clusters), positive and negative light intensity values $L_i$, and other features based on a combination of these elements (e.g. light intensity as a function of size). Various methods may be used to analyze the set of pixel clusters including traditional machine learning techniques where the above-discussed features are computed for a set of images of micro-objects and used to train a classifier to identify micro-objects of interest in new images based on the same features.

Micro-object identification (discussed in greater detail below) may also be used in conjunction with manipulating or repositioning the micro-objects using force, such as OET or DEP force. In some embodiments, micro-objects that are identified in a specific circuit element (e.g. channel or sequestration pen) or location of the microfluidic circuit may be moved to (i.e. repositioned in) another type of circuit element or location of the microfluidic circuit. For example, micro-objects may be identified in a channel in the microfluidic circuit and repositioned in sequestration pens in the microfluidic circuit (referred to herein as "penning" a micro-object). Conversely, micro-objects identified in sequestration pens in the microfluidic circuit may be moved to in channels in the microfluidic circuit. Alternately, one or more micro-objects may be identified in one sequestration pen and repositioned in an empty sequestration pen (referred to herein as "re-penning" a micro-object). According to the embodiment, the micro-objects may be moved using various mechanisms, including OET and DEP force. Similarly, micro-objects may be repositioned sequentially (i.e. one micro-object at a time), in parallel, or any combination thereof (e.g. sequentially repositioning groups of multiple cells in parallel).

In instances where micro-objects are repositioned from the channel to individual sequestration pens (or re-penning from an individual sequestration pen to another sequestration pen), different algorithms may be used to assign micro-objects to empty sequestration pens. In some embodiments, an algorithm will be used to assign micro-objects to empty sequestration pens such that distance between the micro-objects and the pens (i.e. the trajectory or path that the micro-objects have to travel during repositioning) is minimized. In these embodiments, the use of force (e.g. OET or DEP force) to move the micro-objects is also minimized because the micro-objects are only required to travel a minimum distance to be repositioned in an empty sequestration pen.

In these embodiments, a local micro-object density in a channel (i.e. number of micro-objects within a specific spatial area of the channel) may be used to determine a suitable algorithm to assign specific micro-objects in the channel to empty sequestration pens. Local micro-object density may be computed in a number of ways. In some embodiments, local micro-object density may be computed based on a fixed size area (e.g. 200 microns$^2$, or an area of the channel 100 microns long and extending the width of the channel) or using approaches that use various sizes of areas. In other embodiments, local micro-object density may calculated based on clusters of identified micro-objects or the distance between identified micro-objects. Local micro-object density also may be computed by subdividing the channel into a grid or using a "sliding window" approach to compute density for overlapping areas of the channel.

If the local micro-object density is above a threshold value $T1_{density}$, then micro-objects may be assigned to the nearest empty sequestration pens such that the distance between the micro-objects and sequestration pens is minimized. If the local micro-object density is below a specific threshold value $T1_{density}$, then the empty sequestration pens may be assigned to the micro-objects that are closest to the empty sequestration pens, such that the distance between the micro-objects and the sequestration pens is minimized. In some instances, local $T1_{density}$, may be computed based on the number of empty pens as well as the density of micro-objects within the channel in a predefined neighborhood area.

Different methods of computing the distance between a micro-object and an empty sequestration pen (i.e. the trajectory the micro-object or path needs to be moved during penning) may be used to assign specific micro-objects to empty sequestration pens. In some embodiments, the distance between the micro-object and a potential sequestration pen may be computed based only on the optimal trajectory using OET and/or DEP force. In some instances, the optimal trajectory using OET or DEP force involves a combination of orthogonal motion paths (e.g. combination of distinct movement only along a y-axis and an x-axis) to move the micro-objects. In other instances, the distance may be based on the shortest possible path between the micro-object and the sequestration pen, without constraint (i.e. the micro-objects may travel along any path to reach the sequestration pens). In most embodiments, the micro-objects will be re-positioned (i.e. "penned" or "re-penned") using the same trajectory as determined by the algorithm used to calculate the distance (trajectory).

Similarly, in instances where a large number of micro-objects are assigned to sequestration pens (or vice versa), different algorithms may be used to compute the optimal assignment of micro-objects to pens (or vice versa). These algorithms can use different computational methods of determining a micro-object-to-sequestration pen assignment that minimizes the overall distance (i.e. length of the trajectory) that the micro-objects need to be moved in order to reposition the micro-objects into sequestration pens. For example, the algorithms may use the sum of the lengths of all the trajectories as a heuristic to minimize the distance that the micro-objects need to travel. In some embodiments, constraints such as a maximum distance that a micro-object can be moved during repositioning may be introduced into the computation of the optimal assignment. Various combinatorial algorithms may be used to compute the optimal assignment between micro-objects and sequestration pens. Suitable algorithms include, for example, greedy algorithms, nonlinear optimization, heuristic-based algorithms and constrained search. Other similar algorithms are known in the art.

Once the optimal assignment and trajectory has been computed for the micro-objects, a force, such as OET and/or DEP, may be used to move the micro-objects to their assigned pens. The micro-objects may be repositioned using patterns of light, such as a "light cage", that surround the micro-objects and subject the micro-objects to OET and/or DEP force or by using bars or similar structures to apply OET and/or DEP force to the micro-objects. Typically, a light cage will be a structure that substantially encloses the micro-object (e.g. a square, a circle or a polygon). However, in some instances, a light cage may contain a break or an opening such that the micro-object is not fully enclosed.

As discussed above, in most embodiments, the micro-objects will be moved according to the distance (trajectory) used to compute the optimal assignment of micro-objects to pens. According to the embodiment, micro-objects may be moved sequentially or in parallel any combination thereof (e.g. sequentially moving groups of cells in parallel). In embodiments where the micro-objects are moved in parallel, the algorithm used to compute the optimal assignment or trajectory may compare the trajectories and ensure that the micro-objects do not collide when they are moved in parallel by modifying the trajectory and assignments of the micro-objects to pens. In a specific embodiment, the algorithm may "swap" micro-object assignments to pens when a potential collision is identified. In this embodiment, when the optimal trajectory for a first micro-object intersects with the optimal trajectory for a second micro-object, the optimal trajectory for the first micro-object is assigned to the second micro-object and the optimal trajectory for the second micro-object is assigned to the first micro-object. In another specific embodiment, the algorithm delays the repositioning of the first micro-object until such a time that the first and second micro-objects can move along their respective trajectories without colliding.

In some instances, the micro-object density may be so high that the micro-objects need to be separated from one another prior to assigning the micro-objects to sequestration pens and repositioning (i.e. "penning" or "re-penning") the micro-objects. For example, the micro-object density may be so high that the micro-objects cannot be penned using OET and/or DEP force because the light cage used to reposition objects using OET and/or DEP force cannot be used on a single micro-object without interfering with other micro-objects. This interference is of particular concern in instances where it is important to minimize the amount of OET and/or DEP force applied to the micro-object. For examples, instances where the micro-objects could be harmed by OET and/or DEP force or by-products of OET force (e.g. electrolysis associated with OET and/or DEP force). In these instances, information produced during micro-object identification (e.g. the radius, the centroid, the perimeter and the location of a micro-object) may be used to move the micro-objects such the micro-objects may be penned or re-penned without interfering with other cells (herein referred to as "separating" the micro-objects).

In order to identify instances where the micro-objects need to be separated prior to penning, a local micro-object density may be computed based on a defined spatial region and compared to a second threshold value $T2_{density}$. Alternately, the distance between the micro-objects may be computed (e.g. the distance between centroids of micro-objects, the distance between the perimeters of the micro-objects) and used to determine whether the micro-objects need to be separated. However, as can appreciated, in some instances, the distance between micro-objects may be too small to identify the micro-objects as separate micro-objects and micro-objects. In these instances, the micro-objects may be re-identified after repositioning (i.e. "penning") the micro-objects to ensure that each sequestration pen contains a single micro-object.

In some embodiments, a light box is used to separate the micro-objects prior to, or during, penning (or re-penning). When forming the light boxes (or light cages), a division algorithm can be used to compute a set of vertices that partition each identified micro-object in the spatial region of the microfluidic device (e.g. the portion of the channel or the sequestration pen) from the other micro-objects in the same spatial region. However, as can be appreciated by those skilled in the art, the set of vertices may be drawn such that only a subset of the micro-objects in the spatial region of the microfluidic device are separated from the other micro-objects. For example, the set of vertices may only separate the subset of micro-objects in the spatial region that need to be repositioned due to their close proximity to other micro-objects.

In a specific embodiment, a Delaunay triangulation is computed using the centroids of each micro-object. The Delaunay triangulation produces a set of triangles that connect the centroids of the micro-objects. A Voronoi diagram is then computed based on the circumcircles of the triangles computed using the Delaunay Triangulation. The Voronoi diagram is a set of vertices that divide the spatial area into a set of sub-areas such that the distance between the set of vertices and the centroid of the micro-object is maximized. Other methods of computing a set of vertices that partition each cell from the other cells in the spatial region are known in the art.

Figure 6A:
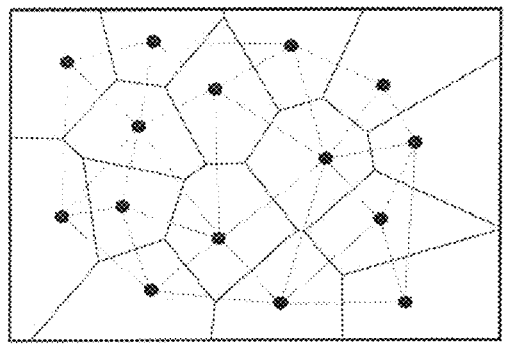
FIGS. 6A-6F illustrate the generation of modified light cages that can be used to separate micro-objects, according to a specific embodiment of the present invention.
Figure 6B:
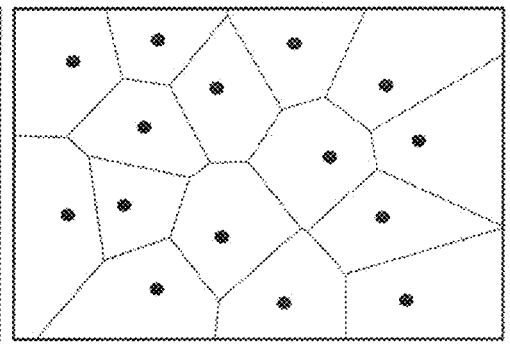
Figure 6C:
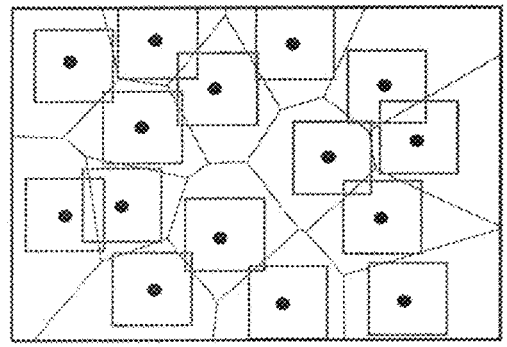
Figure 6D:
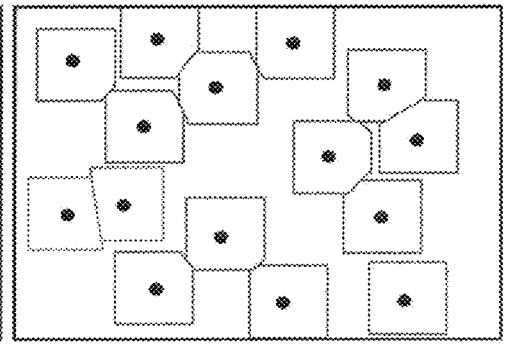
Figure 6E:
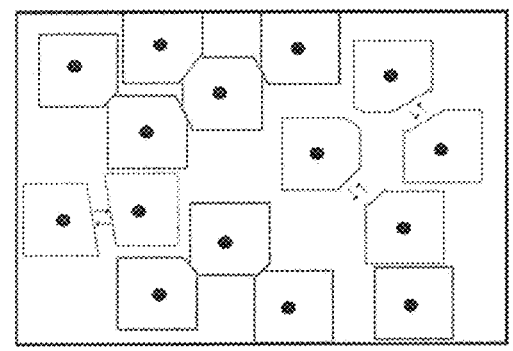
Figure 6F:
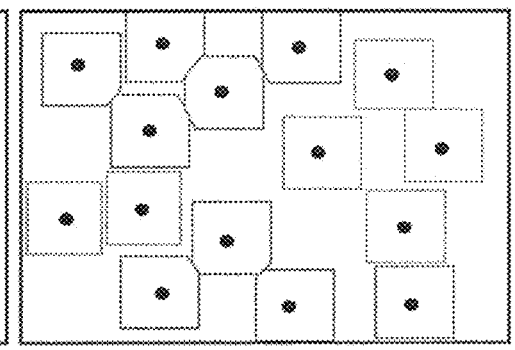

Once the set of vertices has been computed, the set of vertices can be used in combination with OET and/or DEP forces to move the micro-objects. FIGS. 6A-6F illustrate micro-object separation according to various embodiments of the present invention. FIG. 6A illustrates the Delaunay triangulation of a set of micro-objects within a specified spatial region and the corresponding Voronoi diagram. FIG. 6B illustrates the corresponding Voronoi diagram without the Delaunay triangulation. FIG. 6C illustrates light cages typically used to move micro-objects overlaid upon the Voronoi diagram. FIG. 6D illustrates modified light cages generated by computing the intersection between the typical light cages of FIG. 6C and the Voronoi diagram. FIG. 6E illustrates the separation of the micro-objects that are in close proximity with each other using the modified light cages. FIG. 6F illustrates the separated micro-objects.

In one embodiment, one or more light cages are generated by generating a plurality of light bars that link a subset of vertices of the set of vertices, wherein the sub-set of vertices comprises (or consists of) vertices which are most proximal to and surround each micro-object to be moved. For example, any of the polygon shapes shown in FIG. 6B can be used to define a light cage that surrounds a micro-object. In certain embodiments, a light cage formed in this manner can be shrunk to thereby separate the micro-object within the light cage from other micro-objects and/or light cages in the specified spatial region. In other embodiments, a light cage can be defined by superimposing a "standard" light cage design (e.g. a square or circle) upon the polygon shapes (see FIG. 6C) and generating a light cage that results from the intersection of the standard light cage design and the polygon shapes, as illustrated in FIG. 6D. In this example, the intersection of the vertices and the light cages is defined as an area where the light cages do not intersect or overlap, allowing the "standard" light cage to be re-drawn such that it does not interfere with other micro-objects. Regardless of the method of formation, once formed the light cages can be used to separate micro-objects by repositioning the micro-object by moving the micro-objects away from each other. In some instances, modified light cage may be re-drawn as the micro-objects are repositioned such that the original light cages are drawn when the micro-objects are in the final position.

Non-standard (or "modified") light cages may be used to reposition the micro-objects in a variety of embodiments. Depending on the embodiment, the modified light cages for two proximate micro-objects are used to reposition the micro-objects prior to, or after, computing and selecting the trajectory and assignment to a sequestration pen for each micro-object. In some embodiments, modified light cages are used to reposition micro-objects iteratively or sequentially. In addition, modified light cages may be used to pen micro-objects in their assigned sequestration pens. In some embodiments, micro-objects that are closest to the perimeter of the spatial area or closest together in space may be re-positioned or penned prior to repositioning or penning other micro-objects.

Figure 4A:
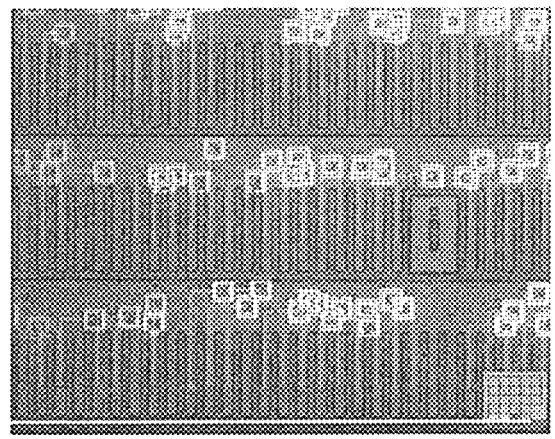
FIGS. 4A, 4B, and 4C depict the penning of micro-objects in parallel, according to one embodiment of the invention.
Figure 4B:
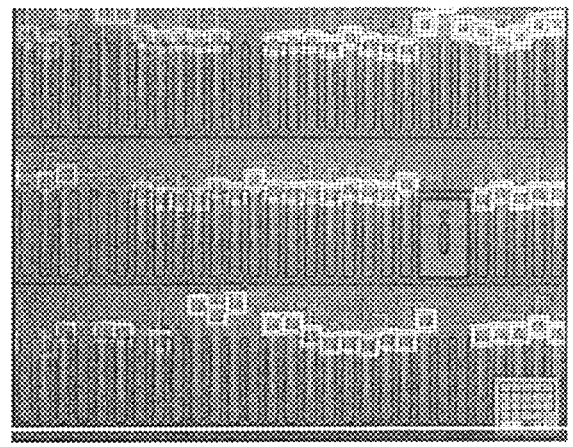
Figure 4C:
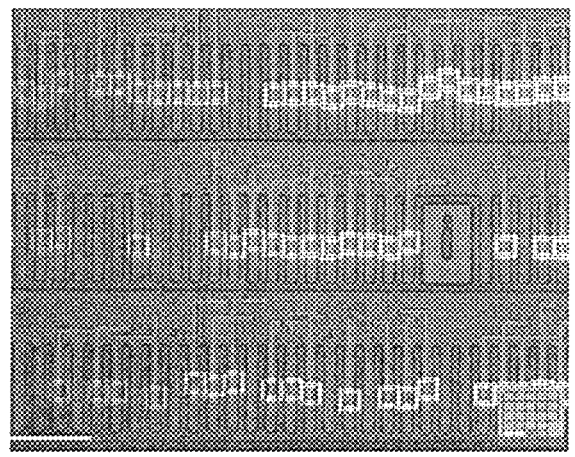

FIGS. 4A, 4B, and 4C illustrate micro-object penning using light boxes. In FIG. 4A, biological cells within the channel of a microfluidic circuit are shown immediately following the identification of the cells and the assignment of cells to pens. The black boxes surrounding the cells illustrate the output of the cell identification algorithm—that is, an identification of cells indicated by a box around the cell. The white boxes surrounding the black boxes are the light cages of OET force used to reposition the cells. Lastly, the black lines that connect the boxes surrounding the cells to the sequestration pens illustrate the optimal trajectory computed in assigning the cells to sequestration pens. FIG. 4B shows the same cells at a later time point in which the light cages have been moved along their selected trajectories. FIG. 4C shows the same cells at a third time point where the light cages have been almost fully moved along their selected trajectories to position the cells in the sequestration pens.

In moving the micro-objects, the speed at which OET and/or DEP is used to move the cells may be gradually accelerated in order to "ramp up" motion of the micro-objects and ensure that the micro-objects are not lost from their light cages. For example, in a specific embodiment, the initial velocity of the micro-objects may be gradually accelerated from a low initial velocity to a higher travelling velocity. This gradual acceleration may be applied both in instances where the micro-objects are automatically repositioned (e.g. penning, re-penning and export) and in instances where the micro-objects are manually repositioned (e.g. manually selecting and moving a cell). Similarly, the high travelling velocity may be "ramped down" to a final velocity of zero when the micro-objects reach the end of their trajectory and are at their final position.

The methods of the invention are useful for the automated detection of micro-objects in all types of microfluidic devices. In certain embodiments, the microfluidic device can include a flow region (or flow channel) and one or more chambers (or sequestration pens). Alternatively, or in addition, the microfluidic device can be an electrokinetic device, such as an optically actuated electrokinetic device, or can include a region configured for electrokinesis. Electrokinetic devices, particularly electrokinetic devices having an array of transistors (e.g., phototransistors), can provide a particularly complicated background if the transistors in the array have an area that is similar to the cross-sectional area of a micro-object that is being detected. The methods described herein can be particularly effective at detecting micro-objects disposed in such a device.

In certain embodiments, the invention further provides machine-readable storage devices for storing non-transitory machine-readable instructions for carrying out any of the methods described herein. The machine-readable instructions can control the imaging device used to obtain the images and/or a processor (e.g., in a computational device) that aligns the images, generates differential images, and/or analyzes the differential images.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 1000 of FIG. 5, whereby processor 1004 would execute the analyses and determinations provided by these engines, subject to instructions provided by any one of, or a combination of, memory components 1006/1008/1010 and user input provided via input device 1014.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical, FLASH memory and non-optical data storage devices. The computer readable medium can also be distributed over a network coupled computer systems so that the computer readable code is stored and executed in a distributed fashion.

EXAMPLES

General Materials and Methods.

System and Microfluidic device: OptoSelect™ chips, manufactured by Berkeley Lights, Inc. and controlled by an optofluidic instrument, also manufactured by Berkeley Lights, Inc., where used in the foregoing experiments. The optofluidic instrument included: a mounting stage for the chip coupled to a temperature controller; a pump and fluid medium conditioning component; and an optical train including a camera and a structured light source suitable for activating phototransistors within the chip. The OptoSelect™ chip included a substrate configured with OptoElectroPositioning (OEP™) technology, which provides a phototransistor-activated OET force. The chip also included a plurality of microfluidic channels, each having a plurality of NanoPen™ chambers (or sequestration pens) fluidically connected thereto. The volume of each sequestration pen was around $1 \times 10^6$ cubic microns. The microfluidic device included conditioned interior surfaces, which were introduced as described in PCT application No. PCT/US2017/034832, filed on May 26, 2017, entitled "Covalently Modified Surfaces, Kits and Methods of Preparation and Use", the contents of which are hereby incorporated by reference in its entirety. Water (250 microliters) was flowed through the microfluidic device at 12 microliters/sec before use.

Preparation for culturing: Culture medium (as below) was then flowed through the microfluidic device at 5 microliters/sec for 5 min.

Perfusion Regime: The Perfusion Method was Either of the Following Two Methods:
1. Perfuse at 0.01 microliters/sec for 2 h; perfuse at 2 microliters/sec for 64 sec; and repeat.
2. Pulse with 4 microliters at 2 microliters/sec every 60 sec; and repeat.

Example 1. Antigen-Specific Cytokine Release Assay

Figure 22:
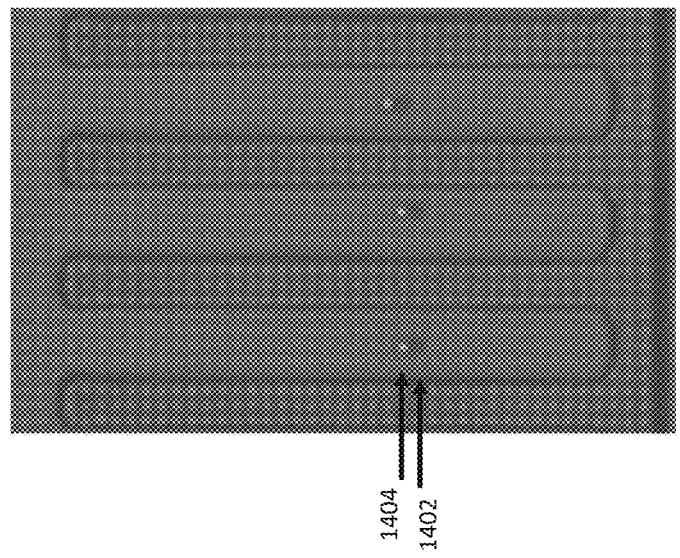
FIG. 22 is a photographic representation of the selective disposition of an antigen-specific T lymphocyte and a micro-object configured to bind a secreted biomolecule of the T lymphocyte within a sequestration pen for use in a method according to one embodiment of the disclosure.

Experimental Design: SLC45A2-specific T cells were tested for activation in presence of tumor cells presenting the SLC45A2 tumor-specific antigen in an Interferon gamma (IFN gamma) release assay on a microfluidic chip. Capture beads for human IFN gamma (Cat. #740352, Biolegend) were flowed into an individual microfluidic chip (Berkeley Lights, Inc.) in T cell media (Adv. RPMI+10% Human AB serum (Cat. #35-060-CI, Corning)+Gln+50 uM 2-mercaptoethanol (BME, Cat. #31350-010, Gibco, ThermoFisher Scientific). The beads exhibited autofluorescence in the range observable in a Cy5 signal channel. Therefore, a brightfield image and an image detecting maximum fluorescence intensity in the Cy5 channel were used in the process of FIG. 12, and further described in the Appendix, to determine the presence of each capture bead, and to resultingly employ the software-implemented method described above to direct single beads to each sequestration pen of the microfluidic chip. After loading of the beads, T cells expanded against the SLC45A2 antigen, as described in PCT Application No. PCT/US2018/043146, filed on Jul. 20, 2018, entitled "Antigen-Presenting Surfaces, Covalently Functionalized Surfaces, Activated T Cells and Uses Thereof", herein incorporated by reference in its entirety, were flowed into the microfluidic chip and loaded into each sequestration pen individually (as single T Cells, but the method is not so limited. More than one T cell may be used within each sequestration pen). The T cells were selectively moved using optically actuated dielectrophoretic (DEP) forces to place one T cell in close proximity to the previously loaded bead in each sequestration pen, as shown in FIG. 22. In FIG. 22, the dark sphere (1402) is the capture bead and the bright sphere (1404) is the T cell, demonstrating that the method of determining the identity of micro-objects and selective resultant delivery as described herein was successful in discriminating between different types of micro-objects and moving only the desired species.

Figure 23B:
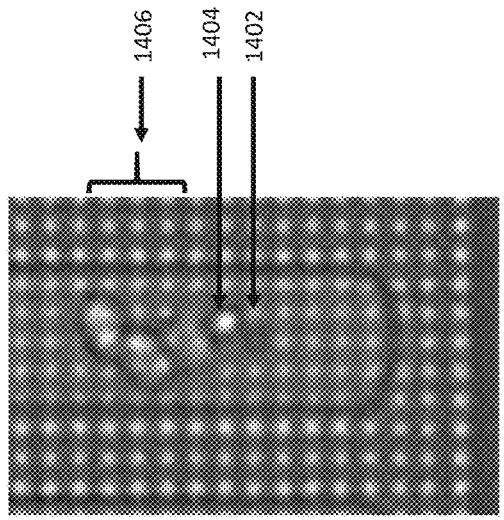
FIG. 23B is a photographic representation showing an enlargement of the area bounded by the box in FIG. 23A, to show the micro-object, T lymphocyte and one (or more) specifically targeted cells in greater detail.
Figure 23A:
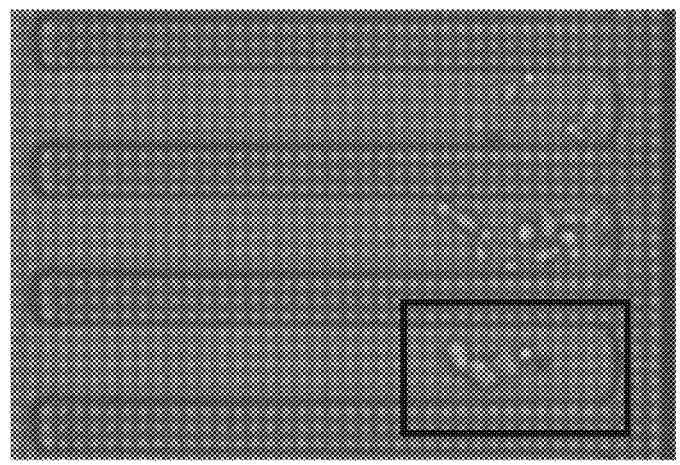
FIG. 23A is a photographic representation of the selective disposition of an antigen specific T lymphocyte and a micro-object configured to bind a secreted biomolecule of the T lymphocyte, after selective disposition of one or more specifically targeted cells for use in a method according to one embodiment of the disclosure.
Figure 24B:
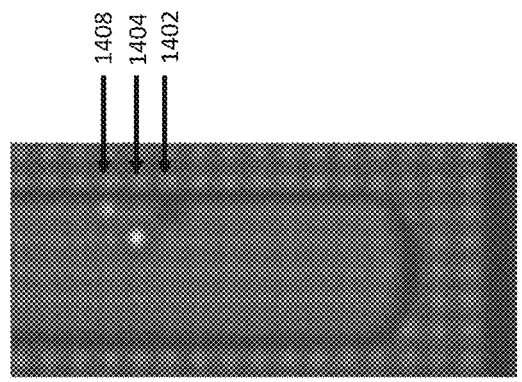
FIG. 24B is a photographic representation showing an enlargement of the area bounded by the box in FIG. 24A to show the micro-object, T lymphocyte and one non-targeted cell in greater detail.
Figure 24A:
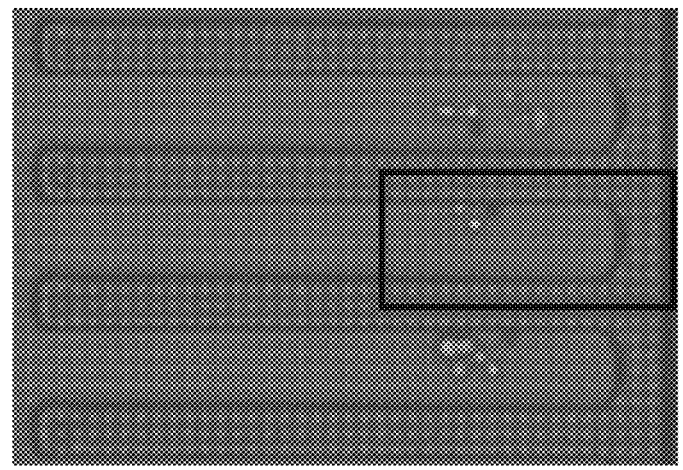
FIG. 24A is a photographic representation of selective disposition of an antigen specific T cell and a micro-object configured to bind a secreted biomolecule of the T lymphocyte, after selective disposition of one or more non-targeted cells for use in a method according to one embodiment of the disclosure.
Figure 25B:
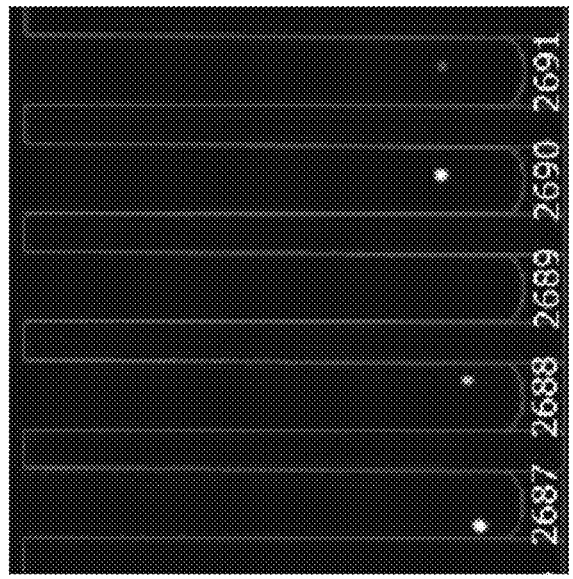
FIG. 25B is a photographic representation showing the same sequestration pens at the same time point, showing fluorescent labelling of secreted biomolecule captured to the micro-object in the Texas Red channel.
Figure 25A:
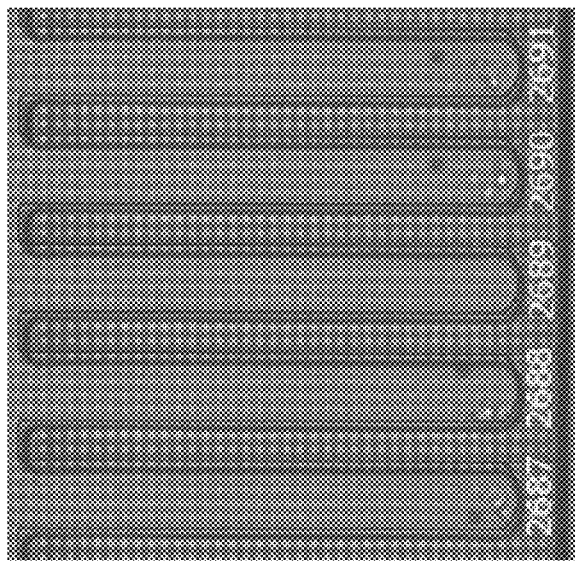
FIG. 25A is a photographic representation of a brightfield image of selected sequestration pens, numbers 2687-2691, each pen showing antigen-specific T lymphocyte, the micro-object configured to bind a secreted biomolecule of the T lymphocyte and specifically targeted cells after a period of incubation.
Figure 26B:
FIG. 26B is a photographic representation of the same sequestration pens at the same time point, showing no fluorescent labelling of secreted biomolecule in the Texas Red channel for the antigen-specific T lymphocyte in the presence of a non-targeted cell.
Figure 26A:
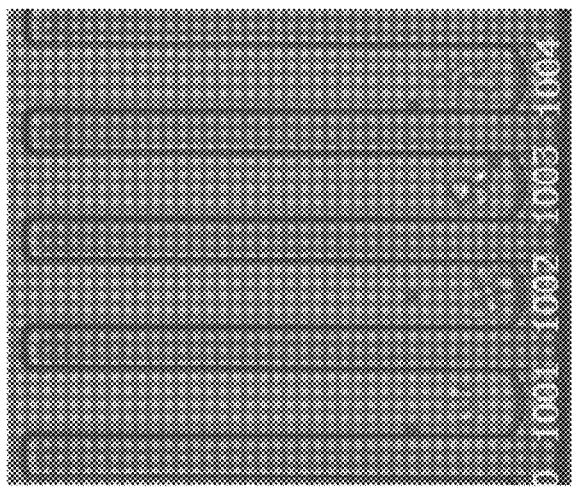
FIG. 26A is a photographic representation of a brightfield image of selected sequestration pens, numbers 1001-1004, each pen showing antigen-specific T lymphocyte, a micro-object configured to bind a secreted biomolecule of the T lymphocyte and non-targeted cells after a period of incubation.

T2 tumor cell lines obtained from lymphoblastoma cells (ATCC® CRL-1992™) were grown in vitro according to standard procedures, then cultured for 4 hours in medium with 3 micrograms/ml Beta 2-microglobulin (Cat #M4890, Sigma-Aldrich) and 40 micrograms/ml SLC45A2 tumor-specific antigenic peptide (Biolegend, Custom Product, SLYSYFQKV (SEQ ID NO. 1)), or TCL1 tumor-specific antigenic peptide (Biolegend, Custom Product, SLLPIMWQL (SEQ ID NO. 2)), to allow presentation of the antigen on the surface of the tumor cells. Each individual population of labeled tumor cells was flowed into a different sector of a microfluidic device (Berkeley Lights, Inc.) in T cell media (Adv. RPMI+10% Human AB serum+Gln+50 uM 2-mercaptoethanol), where the first sector housed the TCL 1 Tumor cells and the second sector housed the SLC45A2 Tumor cells. Groups of tumor cells (~2-5) pulsed with TCL1 tumor-specific antigen or SLC45A2 tumor-specific antigen, respectively were selectively loaded in defined and distinct subsets of sequestration pens, using a sequence of optically induced DEP forces that maximized contact between T cells, tumor cells and beads. The sequence of DEP forces also concentrated the bead and combination of cells to the lower portion of the sequestration pen, within the isolation region of the sequestration pen. Typically, after loading the tumor cells and T cells, each sequestration pen contained 0-5 tumor cells per T cell, as shown in the brightfield images (BF) acquired at the end of the loading process of the microfluidic device containing a first sector containing TCL1-pulsed tumor cells isolated with SLC45A2-specific T cells (FIGS. 23A, 23B) and the second sector containing SLC45A2-pulsed tumor cells isolated with SLC45A2-specific T cells (FIGS. 24A, 24B). As shown in FIG. 23A, the combination of bead, SLC45A2 specific T cell, and multiple TCL 1 pulsed tumor cells is visible in all three sequestration pens shown. FIG. 23B shows an enlargement of the region within the box of the left hand sequestration pen, to clearly show bead 1402, SC45A2 specific T cell 1404, and the groups of TCL 1 pulsed tumor cells 1406. FIG. 24A shows selected pens having a bead, SLC45A2 specific T cell, and SLC45A2 pulsed tumor cells. FIG. 24B shows an enlargement of the region within the box of the central sequestration pen of FIG. 24A to clearly show bead 1402, SLC45A2 specific T cell 1404 and TCL 1 pulsed tumor cell 1408. SLC45A2-specific T cells were expected to secrete IFN gamma in the presence of T2 cells pulsed with the SLC45A2 tumor-associated antigen, whereas SLC45A2-specific T cells were not expected to secrete IFN gamma in the presence of T2 cells presenting the TCL1 tumor-associated antigen. Thus, the latter were used as a negative control for cytokine release. After loading, T cell media (Adv. RPMI+10% Human AB serum+Gln+50 uM BME) supplemented with 50 IU/ml of Interleukin-2 (Cat #8879-IL-050, R&D Systems) and 10 ng/ml of Interleukin-7 (Cat #208-IL-200, R&D Systems) was perfused through the microfluidic channels of the microfluidic device for a period of 6-16 hours. After incubation, an antibody against human IFN gamma fluorescently labeled with Phycoerythrin (PE, Cat. #506507 Biolegend), was flowed into the device, and perfused at 0.02 microliters/sec for 1 hour, to allow diffusion of the fluorescent antibody inside the pens and binding to the capture beads coated with secreted IFN gamma. After perfusion, unbound antibody was removed by perfusing FACS buffer for 30 minutes in the device. Bright field images were obtained for the microfluidic device with T cells and differing tumor cell populations, beads were visualized using the Cy5 fluorescent cube, and presence of IFN gamma on beads was detected using the TXRED fluorescent cube. The three different images were subjected to the method of FIG. 12, additionally as described in the Appendix to assign the identities of the objects seen in the images. FIG. 25A shows the brightfield image of sequestration pens within the second sector of the microfluidic device which contained the SLC45A2 specific T cells, bead, and SLC45A2 pulsed tumor cells. FIG. 25B shows the fluorescent image in the Texas Red channel for the same group of sequestration pens (note superimposed pen numbering in each, the same numbers indicate the same pen), clearly showing captured and IFN gamma (Compare sequestration pens 2687, 2688, 2690 of both images.) In contrast, FIG. 26A shows the brightfield image obtained for a group of sequestration pens in the first sector of the microfluidic device containing the SLC45A2 specific T cell with TCL1 pulsed tumor cells, and FIG. 26B shows the fluorescence observed for the same group of sequestration pens. No fluorescence was observed.

Figure 27:
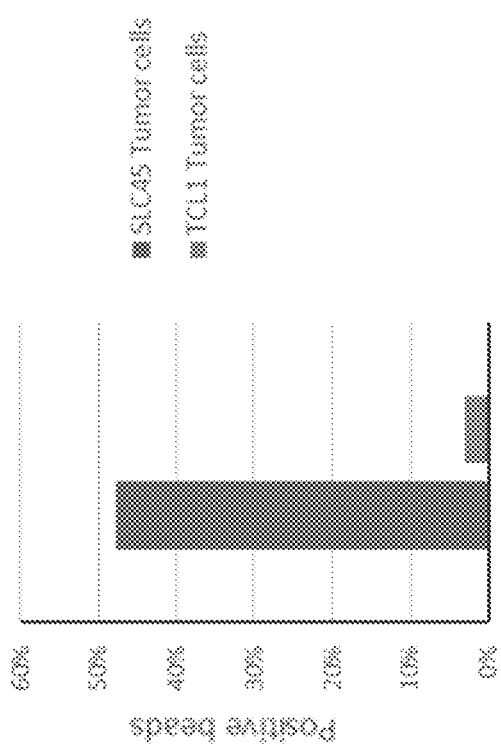
FIG. 27 is a graphical representation of the relative numbers of beads demonstrating activation and capture of a secreted biomolecule selectively by antigen-specific T lymphocytes in the presence of a targeted cell, derived from the methods of detection and characterization according to embodiments of the disclosure.

Results: After incubation in the sequestration pens of T cells, tumor cells and beads, and perfusion of the detection PE-IFN gamma antibody, beads in pens with SLC45A2-pulsed T2 cells and SLC45A2 specific T cells exhibited a fluorescent signal in the TXRED channel (FIG. 25B), but no signal was associated to beads in the presence of TCL1-pulsed 12 cells and SLC45A2 specific T cells (FIG. 26B). The quantification of antigen-specific T cell activation compared to controls shows that more than 50% of the T cells were specifically activated and secreted IFN gamma when coming into contact with tumor cells presenting the SLC45A2 antigenic peptide on their surface, whereas activation of T cells in the present of TCL1-presenting tumor cells was below 5% (FIG. 27). The ability to quantify the number of antigen specific T cells that secrete the cytokine of interest, IFN gamma, is a result of the application of the cell counting methods described herein.

Example 2. Multiplexed Antigen-Specific-Cytokine Release Assay

Figure 28:
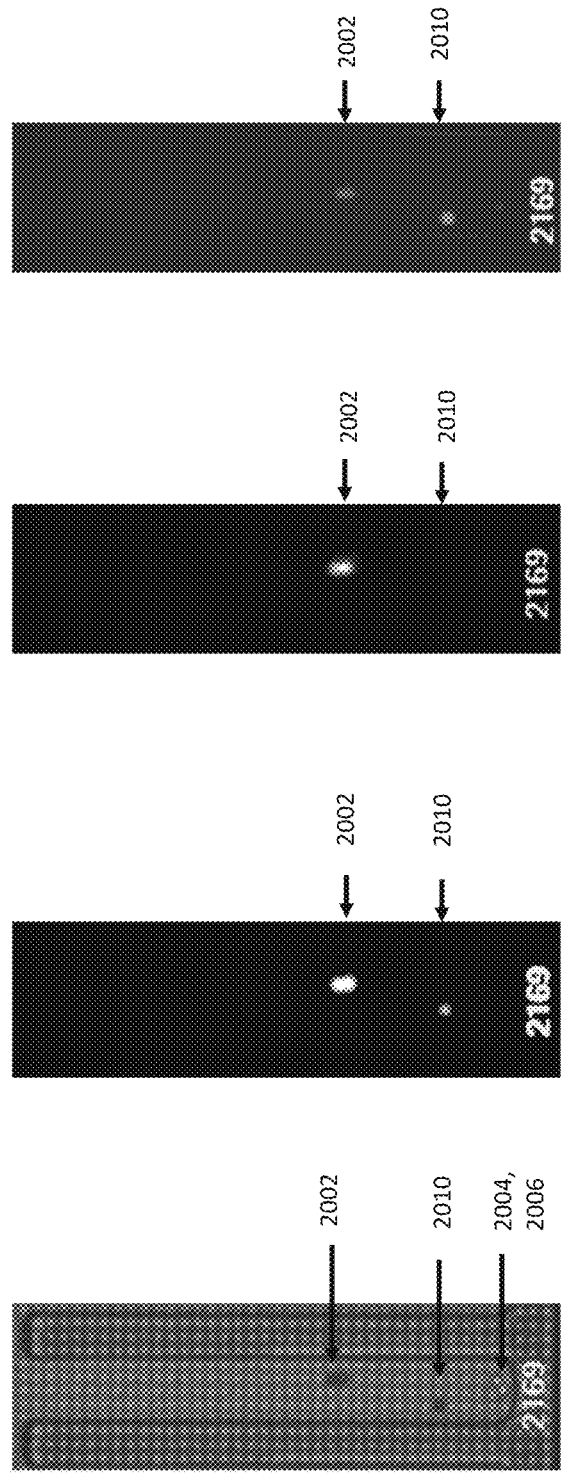
FIGS. 28A-28D are photographic representations of a multiplexed cytokine release assay detecting, moving and characterizing the captures beads and cells according to an embodiment of the disclosure.

Experimental Design: SLC45A2-specific T cells were tested for activation in presence of tumor cells presenting the SLC45A2 tumor-specific antigen in a combined Interferon gamma (IFN gamma) and Tumor Necrosis Factor alpha (TNF alpha) release assay on a microfluidic device as in the general materials section. IFN gamma capture beads, SLC45A2-specific T cells and SLC45A2- or TCL1-presenting tumor cells were loaded on a microfluidic device (Berkeley Lights, Inc.) as described above. In addition, TNF alpha capture beads were flowed into the microfluidic chip and loaded in the same sequestration pens containing IFN gamma capture beads, T cells and tumor cells. The two types of capture beads exhibited different levels of autofluorescence in the range observable in a Cy5 signal channel. Therefore, a brightfield image and an image detecting maximum fluorescence intensity in the Cy5 channel were used to determine and characterize each object using a process as described herein (For some particulars, see FIG. 12, and Appendix), and to selectively move an antigen-specific T cell, one or more tumor cells (target or non-targeted), IFN gamma capture beads and one TNF alpha capture bead in to each sequestration pen. Finally, the optical characterization methods were employed to determine the presence of each capture beads in the sequestration pens. Incubation was performed as described above. After incubation, an antibody against human IFN gamma fluorescently labeled with Phycoerythrin (PE, Cat. #506507 Biolegend) and an antibody against human TNF alpha, fluorescently labeled with Fluorescein isothiocyanate (FITC, Cat #502906 Biolegend) were flowed into the device, and perfused at 0.02 microliters/sec for 1 hour, to allow diffusion of the fluorescent antibodies inside the pens and binding to the capture beads coated with secreted IFN gamma or secreted TNF alpha. After perfusion, unbound antibody was removed by perfusing FACS buffer for 30 minutes in the chip. Bright field images were obtained for the microfluidic device with T cells and differing tumor cell populations, beads were visualized using the Cy5 fluorescent cube, and presence of IFN gamma and TNF alpha on beads was detected using the TXRED or the FITC fluorescent cube, respectively. The four different images were subjected to the method of FIG. 12, additionally as described in the Appendix to assign the identities of the objects seen in the images. As shown in FIG. 28A, the brightfield images shows T cell 2004 and targeted tumor cell 2006 at the base of the sequestration pen. Two micro-objects 2002 and single micro-object 2010 are clearly seen. FIG. 28B (note superimposed pen numbering in each, the same numbers indicate the same pen) shows the fluorescence image in the Cy5 channel, which as described in the preceding sentences, permits clear identification of the two micro-objects 2002 as the IFN gamma capture beads and the dimmer 2010 object as the TNF alpha capture bead. Reference numbers having the same last two numbers represent similar object as in FIGS. 22-26. Only a sequestration pen within the microfluidic device which contained the SLC45A2 specific T cells, bead, and SLC45A2 pulsed tumor cells is shown. FIG. 28C shows the same sequestration pen 2169 visualized in the Texas Red channel, and showed only fluorescence for micro-objects 2002, indicating IFN gamma capture to the bead. Capture bead 2010, which captures TNF alpha, does not fluoresce. FIG. 28D shows the same sequestration pen 2169, with bead 2010 having brighter fluorescence in the FITC channel. While capture beads 2002 demonstrated some bleed through fluorescence into the FITC channel, this bleed through can be resolved by adjusting filter characteristics of the optical system. In any case, the positive signal in the FITC channel for the bead capturing TNF alpha can be clearly distinguished, and multiplex detection of two cytokines released from the antigen specific T cell (in the presence of its specific targeted tumor cell) is achieved.

Example 3. Combined Cytotoxicity and Cytokine Release Assay

Concurrently with assaying IFN gamma release, SLC45A2-specific T cells were tested for killing activity against tumor cells presenting the SLC45A2 tumor-specific antigen on a microfluidic chip. Prior to loading, T2 cells were labeled with 5 uM CellTrace Carboxyfluoroscein succinimidyl ester (CFSE, ThermoFisher, Cat #C34570) in order to differentiate T cells from T2 cells based on fluorescence. Human IFN gamma capture beads, single SLC45A2-specific T cells and pulsed T2 cells were then flowed into an individual microfluidic device (Berkeley Lights, Inc.), as described above. The T2 cells pulsed with SLC45A2 antigen were expected to be targeted and killed by the SLC45A2-specific T cells, while the TCL1-pulsed 12 cells were not expected to be targeted or killed by the SLC45A2-specific T cells, and thus were used as a negative control for T cell cytotoxicity. After loading, T cell media (Adv. RPMI+10% Human AB serum+Gln+50 uM BME) supplemented with 50 IU/ml of Interleukin-2 (Cat #8879-IL-050, R&D Systems), 10 ng/ml of Interleukin-7 (Cat #208-IL-200, R&D Systems), and supplemented with 5 uM fluorogenic Caspase-3 substrate (DEVD) (NucView® 405, Cat. #10405, Biotium) were perfused through the microfluidic channels on each microfluidic chip for a period of 6-16 hours.

Figure 30E:
FIGS. 30A-30E are photographic representations of a cytotoxicity/secreted protein detection co-assay according to one embodiment of the disclosure.
Figure 30D:
Figure 30C:
Figure 30B:
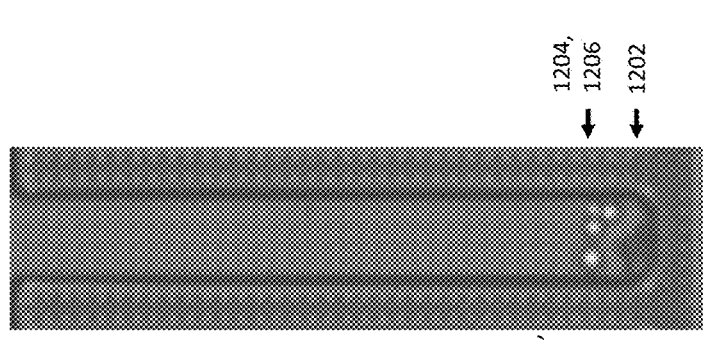
Figure 30A:
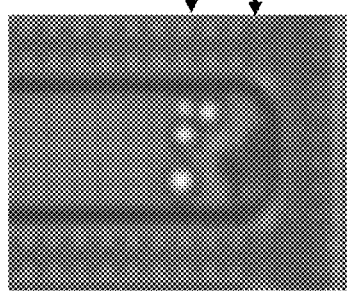

Images of the pens were taken every 60 minutes for the duration of culture. FIGS. 30A and 30B shows brightfield images of same pen, showing a group of IFN gamma capture beads 1202 at the base of the sequestration pen (dark spheres) and a group of SLC45A2-pulsed T2 cells 1206 (specific targets) and a SLC45A2-specific T cell (1204), visible as brighter spheres located just above the capture beads within the pen. 30A is an enlargement of the base of the sequestration pen shown in FIG. 30B. The CellTrace CFSE label and cleaved, now fluorescent Caspase-3 label were visualized using different fluorescent cubes (FITC, DAPI respectively). FIG. 30C shows the CFSE labeled T2 tumor cells 1206 in the FITC channel, indicating their specific location and the intact nature of these cells. FIG. 30D shows fluorescent signal in the DAPI channel at the 3 hour timepoint, which is correlated to one of the targeted T2 tumor cells 1206, indicating caspase 3 activity linked to cell death resulting from the cytotoxic effect of the antigen specific T cell within the sequestration pen (not visible under DAPI fluorescent channel). To link T cell cytotoxicity to cytokine secretion, an antibody against human IFN gamma fluorescently labeled with Phycoerythrin (Cat. #506507 Biolegend), was then flowed into the device and perfused at 0.02 microliters/sec for 1 hour, to allow diffusion of the fluorescent antibody inside the pens and binding to the capture beads coated with secreted IFN gamma. After perfusion, unbound antibody was removed by perfusing FACS buffer for 30 minutes in the chip. Beads were visualized at the 20 hour timepoint using the Cy5 fluorescent cube, and presence of IFN gamma on beads was detected using the TXRED fluorescent cube (FIG. 30E, beads 1202).

Figure 31:
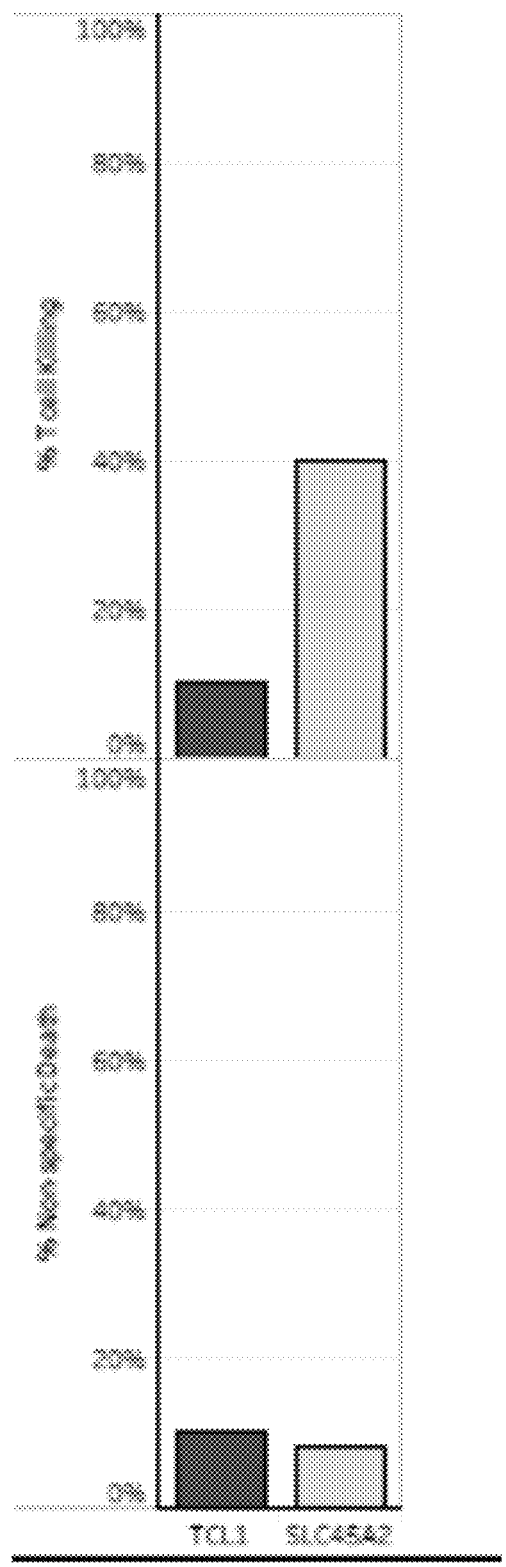
FIG. 31 is a graphical representation of the results of a cytotoxicity assay according to one embodiment of the disclosure.
Figure 32:
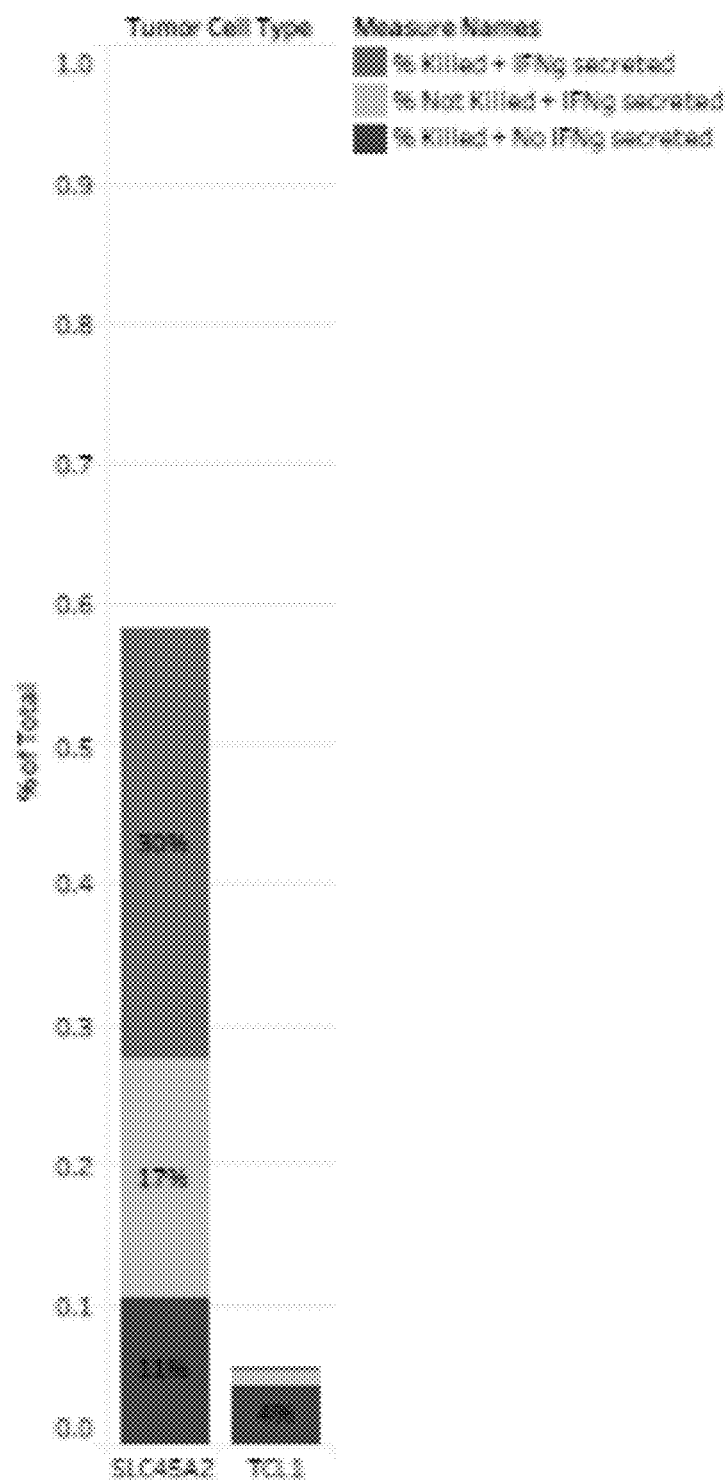
FIG. 32 is a graphical representation of the results of the co-assay of cytotoxicity and secreted protein detection according to one embodiment of the disclosure.

Results: After incubation of T cells, tumor cells and beads in the sequestration pens and perfusion with the Caspase-3 substrate, SLC45A2-pulsed T2 cells in pens with SLC45A2-specific T cells exhibited significantly more cell death than TCL1-pulsed T2 cells incubated with SLC45A2-specific T cells (40% versus 10%, FIG. 31). Both populations of T2 cells showed comparable non-specific death, as measured by death in pens not containing a T cell. Quantification of IFN gamma secretion following cytotoxicity analysis allows for correlations between antigen-specific cytokine secretion and target cell killing. For pens containing SLC45A2-specific T cells and SL45A2-pulsed T2, 30% showed both IFN gamma secretion and T cell-mediated killing (FIG. 32). 17% of pens exhibited IFN gamma secretion in the absence of killing and 11% had killing in the absence of IFN gamma secretion. In control pens containing SLC45A2-specific T cells and TCL1-pulsed T2 cells, 4% exhibited killing in the absence of IFN gamma secretion, 1% had IFN gamma secretion in the absence of killing, while no pens exhibited both IFN gamma secretion and killing.

Example 4. Caspase 8 Cytotoxicity Assay

Assay overview: Caspase-8 is produced and active between early and late stages of apoptosis. The Vybrant™ FAM Caspase-8 Assay Kit is based on a fluorescent inhibitor of caspases (FLICA™) methodology, essentially an affinity label. The reagent associates a fluoromethyl ketone (FMK) moiety, which can react covalently with a cysteine, with a caspase-specific amine acid sequence. For caspase-8, this recognition sequence is leucine-glutamic acid-threonine-aspartic acid (LETD). A fluorescein group is attached as a reporter. The FLICA reagent is thought to interact with the enzymatic reactive center of an activated caspase via the recognition sequence, and then to attach covalently through the FMK moiety. Fluorescence intensity in the FITC channel is directly proportional to the levels of caspase-8 in the cell and is a direct reporter.

Materials: Vybrant™ FAM Caspase-8 Assay Kit-V35119 (Reagents are prepared according to manufacturer's protocol). Anti-fas Ab Human activating clone CH11 (EMD) 0.5 mg/ml (500 ug/ml). MLA Media (RPMI 1640+10% FBS). Jurkat cell line.

Figure 33:
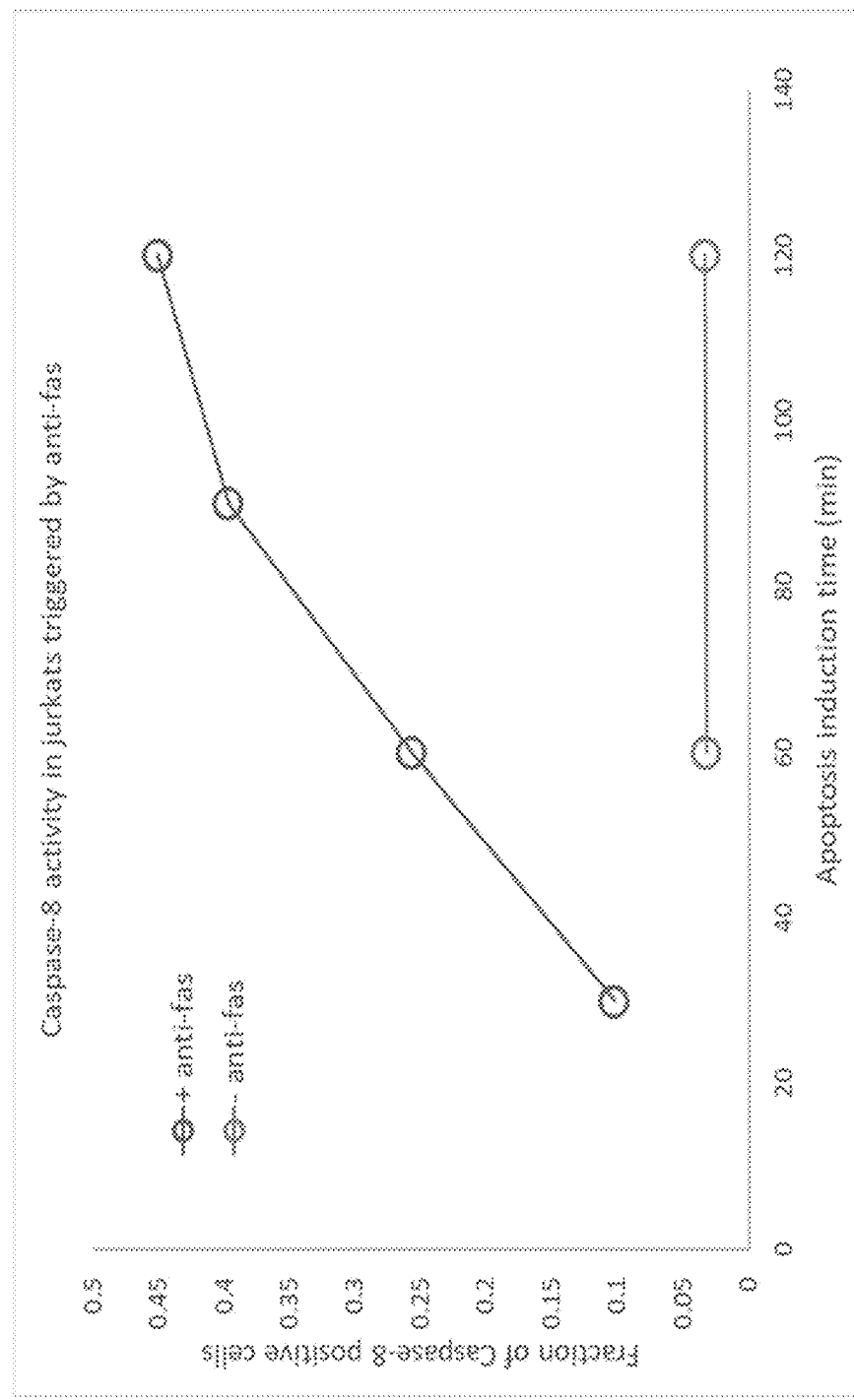
FIG. 33 graphical representation of time course of introduction of Caspase-8 expression as a reporter of apoptosis for a cytotoxicity assay according to one embodiment of the disclosure.
Figures 34A, 34B:
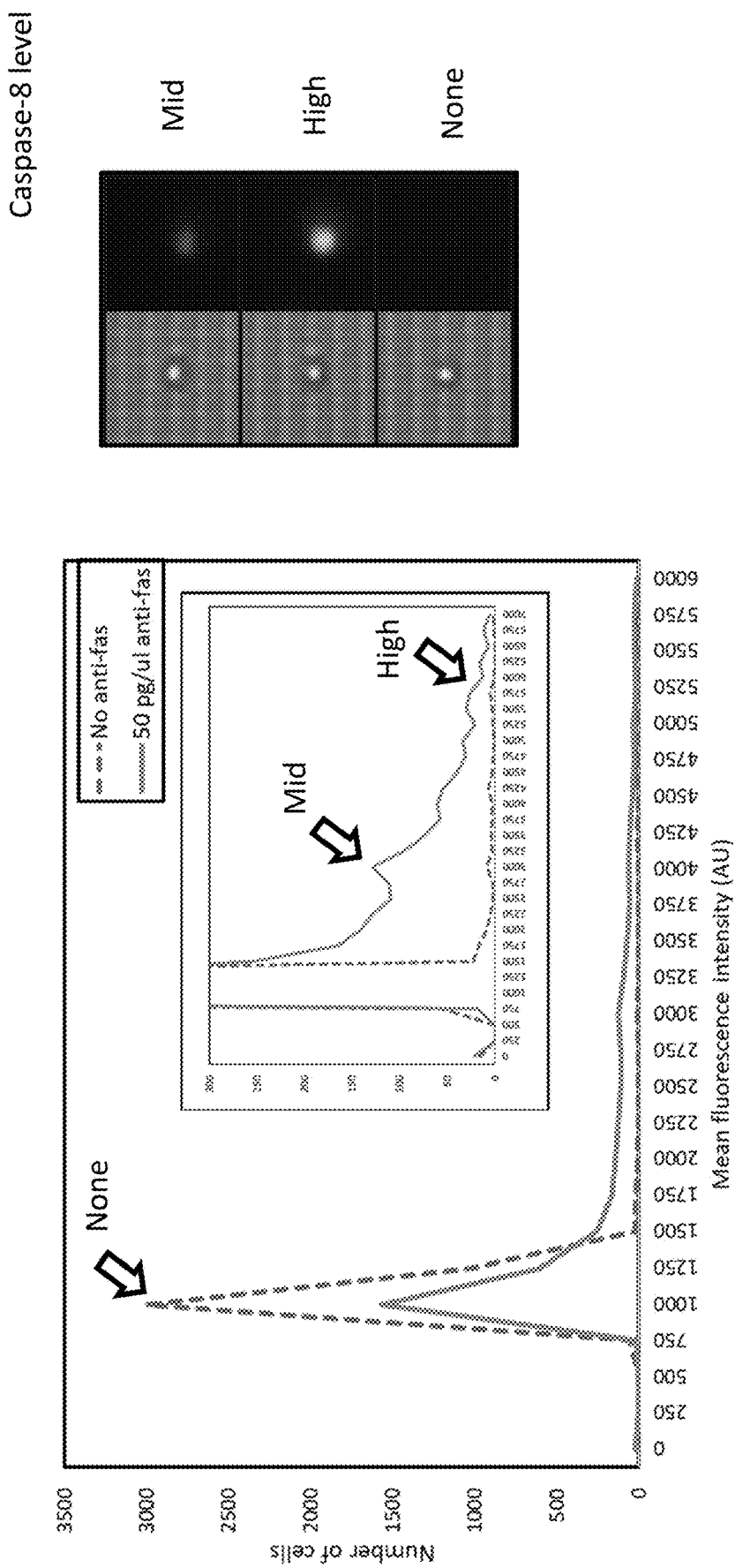
FIG. 34A is a graphical representation of extent of fluorescent signaling in jurkat cells for a cytotoxicity assay according to another embodiment of the disclosure.
FIG. 34B is a photographic representation of brightfield and fluorescent images for individual cells having mid, high and no expression of Caspase-8 activity.

Cells were cultured at 37° C.+5% CO2 to a density of ~5 e5. Cells were pelleted and resuspended in fresh MLA media at a density of 1 e6 just prior to inducing apoptosis; 100 ul of resuspended culture was aliquoted into wells of a 96-well tissue culture plate. Apoptosis was triggered by adding 2 ul of anti-fas that was diluted to 50 ug/ml with PBS. Apoptosis could alternatively be triggered by a number of other substances (eg. Staurosporine, 3,3'-Diindolylmethane, TNF-related apoptosis-inducing ligand (TRAIL), cytotoxic T cells or antibodies secreted by B cells). Background caspase-8 activity was determined by adding 2 ul of PBS (no anti-fas). Cells were incubated at 37° C.+5% CO2 for 90 min. Optimal apoptosis induction time was determined empirically for this cell line as shown in FIG. 33. After 90 min. of incubation, 2 ul of 50× Caspase-8 assay reagent was added to each 100 ul culture and incubated at 37° C.+5% CO2 for an additional 60 min. After 60 min, cells were washed 2× with 100 ul 1× Caspase-8 wash buffer and resuspended a third time in 1× caspase-8 wash buffer. Cells were imported on to a microfluidic device (Berkeley Lights, Inc.), preequilibrated with 1× caspase-8 wash buffer. Cells were detected in brightfield and caspase-8 activity was determined by measuring average FITC fluorescence intensity of the cell. In FIG. 34A, the distribution of Caspase-8 expression in jurkat cells treated for 120 min. with 50 pg/ul anti-fas vs. no antibody control is shown. Inset panel highlights the increase in Caspase-8 positive cells in the anti-fas treated sample. Arrows correspond to the mean fluorescence intensities of representative images shown in FIG. 34B. In FIG. 34B, images in brightfield and FITC channels of representative sequestration pens, each showing jurkat cells with/without Caspase-8 expression at low, high and no caspase-8 expression level. The results show that apoptotic cells having Caspase-8 expression can be definitively and selectively detected within a microfluidic environment.

While the above experiment used initial treatment of the jurkat cells outside of the microfluidic device, the experiment is not so limited. Target cells (e.g. jurkats) are imported on to the microfluidic device and penned, as described above. Apoptosis is induced within the microfluidic environment by either media perfusion containing anti-fas or any other compound capable of diffusing into pens or by co-penning T cells or B cells with the target cell. After the desired apoptosis induction time, 20 ul of 2× Caspase-8 assay reagent is imported and cultured at 37° C. for 60 min. After 60 min. unincorporated Caspase-8 assay reagent is rinsed away flushing the chip 10 times with 20 ul of 1× caspase-8 wash buffer at 0.5 ul/sec with 30 sec. pauses in between each wash. After washing, cells are detected in brightfield and caspase-8 activity is determined by measuring average FITC fluorescence intensity of the cell.

| Informal SEQ ID LISTING. | | |
|---|---|---|
| SEQ ID NO. | Sequence | Type |
| 1 | SLYSYFQKV | Artificial |
| 2 | SLLPIMWQL | Artificial |

Although specific embodiments and applications of the invention have been described in this specification, these embodiments and applications are exemplary only, and many variations are possible.

What is claimed:

1. A method of assaying for antigen-specific cytotoxicity of a T lymphocyte (T cell) in a microfluidic device, the method comprising:
disposing the T cell within the microfluidic device; wherein the microfluidic device comprises a flow region for containing a flow of a first fluidic medium and a chamber opening to the flow region;
disposing a target cell in proximity to the T cell, wherein the target cell is configured to capture a secreted biomolecule from the T cell;
detecting the secreted biomolecule captured by the target cell after a period of exposure in proximity to the T cell by:
receiving a first image and one or more second images of a region of interest;
transforming each of the one or more second images to optically align with the first image;
processing pixel data in the first image using a machine learning algorithm to detect target cells present in the region of interest, the detection comprising identifying a boundary of each target cell; and
detecting a signal located within the boundary of each detected target cell in each of the one or more second images; and
determining the viability of the target cell after a period of exposure in proximity to the T cell.

2. The method of claim 1, wherein the target cell expresses an antigen for which the T cell is specific.

3. The method of claim 1, wherein the target cell is a cancer cell.

4. The method of claim 1, wherein the chamber comprises a sequestration pen and the sequestration pen comprises an isolation region having a single opening and a connection region fluidically connecting the isolation region to the flow region, the isolation region being an unswept region of the microfluidic device.

5. The method of claim 1, wherein the T cell and the target cell are each disposed in the chamber.

6. The method of claim 1, wherein determining the viability of the target cell comprises contacting the target cell with a detectable marker configured to label a non-viable cell.

7. The method of claim 1, further comprising labelling the T cell for the presence of one or more cell surface markers associated with proliferation, activation, metabolic activity, memory, exhaustion, and/or lineage.

8. A kit for assaying antigen-specific cytotoxicity by a T lymphocyte (T cell) in a microfluidic device, the kit comprising:
a microfluidic device comprising a flow region for containing a flow of a first fluidic medium and a chamber opening to the flow region; wherein the chamber comprises an isolation region having a single opening; and a connection region fluidically connecting the isolation region to the flow region; wherein the isolation region is an unswept region of the microfluidic device;
a cytotoxicity detection reagent configured to detect viability of a target cell; and
an image acquisition unit configured to detect a secreted biomolecule captured by the target cell when released from the T cell and:
receive a first image and one or more second images of a region of interest;
transform each of the one or more second images to optically align with the first image;
process pixel data in the first image using a machine learning algorithm to detect target cells present in the region of interest, the detection comprising identifying a boundary of each target cell; and
detect a signal located within the boundary of each detected target cell in each of the one or more second images.

9. The kit of claim 8, wherein the cytotoxicity detection reagent comprises a reagent configured to label an apoptotic cell.

10. The kit of claim 8, wherein the cytotoxicity detection reagent comprises a reagent configured to detect calcium flux or mitochondrial membrane potential.

11. The kit of claim 8, further comprising a first capture object configured to capture a first secreted biomolecule of a T cell.

12. The method of claim 1, wherein:
the first image is an illuminated image, and the second image is a non-illuminated image; or
the first image is a non-illuminated image, and the second image is an illuminated image or a non-illuminated image.

13. The method of claim 12, wherein the non-illuminated image is a fluorescent image, an infrared image, or an ultraviolet image.

14. The method of claim 1, wherein receiving the second image of the region of interest comprises receiving more than one second images, at least one of the more than one second images is a fluorescent image, and wherein each of the one or more second images is a fluorescent image.

15. The method of claim 13, wherein each fluorescent image represents a fluorescent signal from a unique portion of the visible light spectrum, and wherein each fluorescent image represents fluorescent signal from a non-overlapping portion of the visible light spectrum.

16. The method of claim 1, further comprising pre-processing the first image and the second image to reduce anomalies in the image data.

17. The method of claim 16, wherein the pre-processing comprises reducing noise and/or optical distortion introduced during generation of the first image and the at least one second image.

18. The method of claim 1, wherein determining a viability of the target cell further comprises processing pixel data in the first image using a machine learning algorithm and detecting the target cell present in the region of interest thereby identifying the boundary of the target cell.

19. The method of claim 18, wherein processing pixel data in the first image comprises using the machine learning algorithm to generate a plurality of pixel masks from the first image for a corresponding plurality of target cell characteristics, and wherein each pixel mask comprises a set of pixel annotations, each pixel annotation of the set representing a probability that a corresponding pixel in the image represents the corresponding target cell characteristic.

20. The method of claim 19, wherein the plurality of target cell characteristics comprises at least: (i) target cell center; (ii) target cell edge; and (iii) non-target cell.

21. The method of claim 20, wherein detecting the target cell is based upon the pixel mask corresponding to the target cell center characteristic or a combination of pixel masks that includes the pixel mask corresponding to the target cell center characteristic.

22. The method of claim 1, wherein disposing the T cell within the microfluidic device comprising disposing a single T cell into the chamber.

23. The method of claim 22, wherein the microfluidic device further comprises a plurality of chambers and disposing the T cell within the microfluidic device comprises disposing a plurality of T cells within the microfluidic device and disposing a single T cell of the plurality of T cells into corresponding chamber of the plurality of chambers.

* * * * *

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: SLC45A2 tumorspecific antigenic peptide
<220> FEATURE:
<221> NAME/KEY: Artificial Sequence
<222> LOCATION: (1)..(9)
<220> FEATURE:
<221> NAME/KEY: MISC_FEATURE
<222> LOCATION: (1)..(9)
<223> OTHER INFORMATION: SLC45A2 tumorspecific antigenic peptide

<400> SEQUENCE: 1

Ser Leu Tyr Ser Tyr Phe Gln Lys Val
1               5

<210> SEQ ID NO 2
<211> LENGTH: 9
<212> TYPE: PRT
<213> ORGANISM: Artificial Sequence
<220> FEATURE:
<223> OTHER INFORMATION: Artificial Sequence
<220> FEATURE:
<221> NAME/KEY: Artificial Sequence
<222> LOCATION: (1)..(9)
<220> FEATURE:
<221> NAME/KEY: MISC_FEATURE
<222> LOCATION: (1)..(9)

```
<223> OTHER INFORMATION: TCL1 tumor-specific antigenic peptide

<400> SEQUENCE: 2

Ser Leu Leu Pro Ile Met Trp Gln Leu
1               5
```